United States Patent
Gharat et al.

(10) Patent No.: US 7,842,703 B2
(45) Date of Patent: Nov. 30, 2010

(54) SUBSTITUTED BENZOFUSED DERIVATIVES AND THEIR USE AS VANILLOID RECEPTOR LIGANDS

(75) Inventors: Laxmikant Atmaram Gharat, Thane (IN); Uday Mukund Joshi, Thane (IN); Neelima Khairatkar-Joshi, Thane (IN); Suresh Mahadev Kadam, Thane (IN)

(73) Assignee: Glenmark Pharmaceuticals S.A., La Chaux-De-Fonds (CH)

( * ) Notice: Subject to any disclaimer, the term of this patent is extended or adjusted under 35 U.S.C. 154(b) by 11 days.

(21) Appl. No.: 12/067,879

(22) PCT Filed: Oct. 9, 2006

(86) PCT No.: PCT/IB2006/002814

§ 371 (c)(1),
(2), (4) Date: Mar. 24, 2008

(87) PCT Pub. No.: WO2007/042906

PCT Pub. Date: Apr. 19, 2007

(65) Prior Publication Data

US 2008/0269253 A1  Oct. 30, 2008

Related U.S. Application Data

(60) Provisional application No. 60/730,660, filed on Oct. 26, 2006, provisional application No. 60/807,205, filed on Jul. 13, 2006.

(30) Foreign Application Priority Data

Oct. 7, 2005  (IN) .................. 1269/MUM/2005
Jun. 26, 2006  (IN) .................. 996/MUM/2006

(51) Int. Cl.
A61K 31/4725  (2006.01)
C07D 217/02  (2006.01)
C07D 217/08  (2006.01)

(52) U.S. Cl. ............. 514/309; 514/310; 546/141; 546/143

(58) Field of Classification Search ............. 514/314, 514/256, 278, 367; 546/135, 17; 548/147; 544/230

See application file for complete search history.

(56) References Cited

U.S. PATENT DOCUMENTS

| | | | |
|---|---|---|---|
| 5,869,478 | A | 2/1999 | Ding et al. |
| 6,933,311 | B2 | 8/2005 | Lee et al. |
| 6,939,891 | B2 | 9/2005 | Rami et al. |
| 2007/0249614 | A1* | 10/2007 | Brown et al. ............. 514/249 |

FOREIGN PATENT DOCUMENTS

| | | |
|---|---|---|
| EP | 0587180 | 3/1994 |
| EP | 0747374 | 12/1996 |
| FR | 2661676 | 11/1991 |
| WO | WO-98/45542 | 3/1998 |
| WO | WO-00/03681 | 1/2000 |
| WO | WO-02/08221 | 1/2002 |
| WO | WO-02/16317 | 2/2002 |
| WO | WO-02/16318 | 2/2002 |
| WO | WO-02/16319 | 2/2002 |
| WO | WO-03/080578 | 10/2003 |
| WO | WO-2004/035533 | 4/2004 |
| WO | WO-2004/103281 | 12/2004 |
| WO | WO-2004/108133 | 12/2004 |
| WO | WO-2004/111009 | 12/2004 |
| WO | WO-2005/007652 | 1/2005 |
| WO | WO-2005/009977 | 2/2005 |
| WO | WO-2005/075463 | 8/2005 |

OTHER PUBLICATIONS

Vippagunta et al., Crystalline solids, 2001, Advanced Drug Delivery Reviews, 48, pp. 3 and 18.*
Wolff et al., Burger's Medicinal Chemistry and Drug Discovery, 1994, Wiley-Interscience, Fifth Edition, vol. I: Principles and Practice, pp. 975-977.*
Chemical Abstracts Service, Columbus, OH, US; Jul. 3, 2005; XP002414754.
Chemical Abstracts Service, Columbus, OH, US; Jan. 24, 2006; XP002414755.
Accession No. 2036258272 CHEMCATS, Publication Date: Feb. 13, 2008.
Accession No. 2032584823 CHEMCATS, Publication Date: Feb. 13, 2008.

* cited by examiner

*Primary Examiner*—Kamal A Saeed
*Assistant Examiner*—Kristin Bianchi
(74) *Attorney, Agent, or Firm*—Blank Rome LLP

(57) ABSTRACT

The present invention relates to substituted benzofused derivatives, which can be used as vanilloid receptor ligands, method of treating diseases, conditions and/or disorders modulated by vanilloid receptors with them, and processes for preparing them.

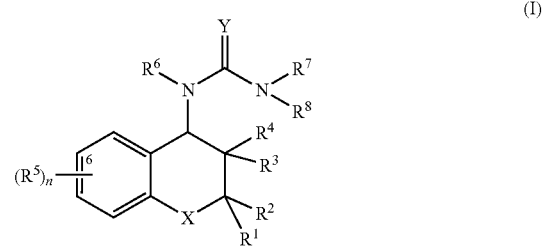

40 Claims, No Drawings

SUBSTITUTED BENZOFUSED DERIVATIVES AND THEIR USE AS VANILLOID RECEPTOR LIGANDS

This application claims the benefit of Indian Provisional Patent Application Nos. 1269/MUM/2005, filed Oct. 7, 2005, and 996/MUM/2006, filed Jun. 26, 2006, and U.S. Provisional Patent Application Nos. 60/730,660, filed Oct. 26, 2005, and 60/807,205, filed Jul. 13, 2006, all of which are incorporated herein by reference in their entirety.

FIELD OF THE INVENTION

The present invention relates to substituted benzofused derivatives, which can be used as vanilloid receptor ligands, methods of treating diseases, conditions and/or disorders modulated by vanilloid receptors with them, and processes for preparing them.

BACKGROUND OF THE INVENTION

Pain is the most common symptom for which patients seek medical advice and treatment Pain can be acute or chronic. While acute pain is usually self-limiting, chronic pain persists for 3 months or longer and can lead to significant changes in a patient's personality, lifestyle, functional ability and overall quality of life (K. M. Foley, Pain, in Cecil Textbook of Medicine 100-107, J. C. Bennett and F. Plum eds., 20th ed., 1996). The sensation of pain can be triggered by any number of physical or chemical stimuli and the sensory neurons which mediate the response to these harmful stimuli are known as "nociceptors". Nociceptors are primary sensory afferent (C and Aδ fibers) neurons that are activated by a wide variety of noxious stimuli including chemical, mechanical, thermal, and proton (pH<6) modalities.

Moreover, chronic pain can be classified as either nociceptive or neuropathic. Nociceptive pain includes tissue injury-induced pain and inflammatory pain such as that associated with arthritis. Neuropathic pain is caused by damage to the sensory nerves of the peripheral or central nervous system and is maintained by aberrant somatosensory processing. There is a large body of evidence relating activity at vanilloid receptors (VR1) (V. Di Marzo et al., Current Opinion in Neurobiology 12: 372-379, 2002) to pain processing.

The lipophillic vanilloid, Capsaicin (8-methyl-N-vanillyl-6-nonenamides; CAP) is known to stimulate pain pathways through the release of a variety of sensory afferent neurotransmitters via a specific cell surface capsaicin receptor, cloned as the first vanilloid receptor (VR1 now known as TRPV1) (Caterina M J, et. al., Science, Apr. 14; 288 (5464): 306-13, 2000). Capsaicin is the main pungent component in hot pepper. Hot pepper has been used historically not only as a spice, but also as a traditional medicine in the treatment of gastric disorders orally, and applied locally for the relief of pain and inflammation. CAP has a wide spectrum of biological actions and not only exhibits effects on the cardiovascular and respiratory systems, but also induces pain and irritancy on local application. CAP, however, after such induction of pain induces desensitization, both to CAP itself and also to other noxious stimuli, thereby stopping the pain. The intradermal administration of capsaicin is characterized by an initial burning or hot sensation followed by a prolonged period of analgesia. The analgesic component of VR1 receptor activation is thought to be mediated by a capsaicin-induced desensitization of the primary sensory afferent terminal. Based on this property, CAP and its analogues such as olvanil, nuvanil, DA-5018, SDZ-249482, and resiniferatoxin are either used or are under development as analgesic agents or therapeutic agents for urinary incontinence or skin disorders (Wriggleworth and Walpore, Drugs of the Future, 23: pp 531-538, 1998).

VR1 is widely expressed in non-neuronal tissues in various organ systems, and the functional roles of VR1 in various systems are not properly understood at this time. An increasing number of animal studies have revealed the possible involvement of VR1 receptors in a number of pathologies. Based on this information VR1 is now being considered as a molecular target for various indications such as migraine, arthralgia, diabetic neuropathy, neurodegeneration, neurotic skin disorder, stroke, cardiac pain arising from an ischemic myocardium, Huntington's disease, memory deficits, restricted brain function, amyotrophic lateral sclerosis (ALS), dementia, urinary bladder hypersensitiveness, urinary incontinence, vulvodynia, pruritic conditions such as uremic pruritus, irritable bowel syndrome including gastro-esophageal reflux disease, enteritis, ileitis, stomach-duodenal ulcer, inflammatory bowel disease including Crohn's disease, celiac disease and inflammatory diseases such as pancreatitis, and in respiratory disorders such as allergic and non-allergic rhinitis, asthma or chronic obstructive pulmonary disease, irritation of skin, eye or mucous membrane, dermatitis, and in non specific disorders such as fervescence, retinopathy, muscle spasms, emesis, dyskinesias and depression. Specifically VR1 antagonists are likely to be useful in multiple sub-types of pain such as acute, chronic, neuropathic pain or post-operative pain, as well as in pain due to neuralgia (e.g., post herpetic neuralgia, trigeminal neuralgia, and in pain due to diabetic neuropathy, dental pain as well as cancer pain. Additionally, VR1 antagonists will also prove useful in the treatment of inflammatory pain conditions such as arthritis or osteoarthritis. VR1 antagonists hold potential benefit in diabetes, obesity, urticaria, actinic keratosis, keratocanthoma, alopecia, Meniere's disease, tinnitus, hyperacusis and anxiety disorders.

One class of natural and synthetic compounds that modulate the function of vanilloid Receptor (VR1) have been characterized by the presence of a vanillyl (4-hydroxy 3-methoxybenzyl) group or a functionally equivalent group and the same have been widely studied and is extensively reviewed by Szallasi and Blumberg (The Am. Soc. for Pharmacology and Experimental Therapeutics, Vol. 51, No. 2, 1999).

Various vanilloid agonists and antagonists have been developed for the treatment of pain; the agonists work through desensitizing the receptor while antagonists block its stimulation by (patho) physiological ligands. The first antagonist Capsazepine was developed by Novartis. There are other VR1 antagonists, which are at the preclinical stage, for example, Amore Pacific's PAC-20030, Neurogen's BCTC, Abbott's A-425619 and Amgen's AMG-9810.

European Publication No. 0 462 761 discloses certain fused compounds having the formula:

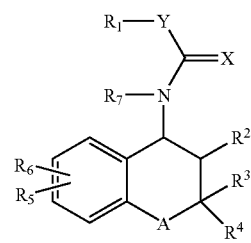

which are potassium channel activators and a method of using them as antiischemic and/or anti-arrhythmic agents. PCT Publication No. WO 2005/075463 describes certain benzopyran derivatives as potassium channel activators. European Patent Publication No. 0 587 180 discloses certain benzofused derivatives for use in the treatment of ischemic conditions and arrythmia. European Patent Publication No. 0 747 374 discloses compounds having the formula:

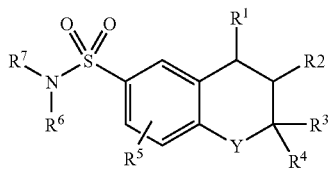

as potassium channel activators. PCT Publication No. WO 98/045542 discloses chroman derivatives for the treatment of cardiac insufficiency.

PCT Publication No. WO 2003/080578 discloses heteroaromatic ureas as vanilloid receptor (VR1) modulators, in particular antagonists, for treating pain and/or inflammation. PCT Publication No. WO 2005/007652 describes substituted quinolin-4-yl-amine analogues useful in the treatment of conditions related to capsaicin receptor activation. PCT Publication No. WO 05/009977 discloses substituted pyrmidinyl-4-yl-amine analogues used to modulate vanilloid receptor activity. Other vanilloid receptor modulating compounds are disclosed in U.S. Pat. Nos. 6,933,311 and 6,939,891; and PCT Publication Nos. WO 02/08221, 02/16317, 02/16318, 02/16319, 04/035533, 04/103281, 04/108133 and 04/111009.

In efforts to discover better analgesics for the treatment of both acute and chronic pain, and to develop treatments for various neuropathic pain states, there still exists a need for a more effective and safe therapeutic treatment of diseases, conditions and/or disorders modulated by vanilloid receptors.

SUMMARY OF THE INVENTION

The present invention provides vanilloid receptor ligands of the formula:

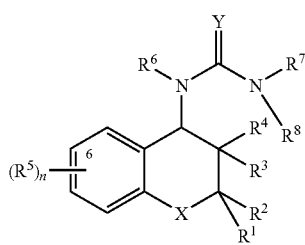

(I)

analogs thereof, pharmaceutically acceptable salts thereof, pharmaceutically acceptable solvates thereof, pharmaceutically acceptable hydrates thereof, N-oxides thereof, tautomers thereof, regioisomers thereof, stereoisomers thereof, prodrugs thereof and polymorphs thereof, wherein:

X and Y are independently O, $S(O)_m$, or $NR^e$;

$R^1$ and $R^2$ are joined together to form an optionally substituted 3 to 7 membered saturated or unsaturated cyclic ring, which may optionally include one or more heteroatoms selected from O, $NR^9$ or $S(O)_m$;

$R^3$ and $R^4$ are independently hydrogen, cyano, halogen, —$OR^9$, substituted or unsubstituted alkyl or —$NR^9R^{10}$, or $R^3$ and $R^4$ together form an oxo group;

(a) $R^5$, $R^6$ and $R^7$ are independently hydrogen, nitro, cyano, halogen, —$OR^9$, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —$NR^9R^{10}$, —C(=L)-$R^9$, —C(O)O—$R^9$, —C(O)$NR^9R^{10}$, —$S(O)_m$—$R^9$, or —$S(O)_m$—$NR^9R^{10}$; and $R^8$ is hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —$NR^9R^{10}$, —C(=L)-$R^9$, —C(O)O—$R^9$, —C(O)$NR^9R^{10}$, —$S(O)_m$—$R^9$, or —$S(O)_m$—$NR^9R^{10}$; or (b) $R^5$ and $R^6$ are as defined above; and $R^7$ and $R^8$ are joined together to form an optionally substituted 3 to 7 membered saturated or unsaturated cyclic ring, which may optionally include up to two heteroatoms selected from O, $NR^e$ or S;

each occurrence of $R^9$ and $R^{10}$ may be the same or different and is independently hydrogen, —$OR^a$, —$SR^a$, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —$NR^aR^b$, —C(=L)-$R^a$, —C(O)O—$R^a$, —C(O)$NR^aR^b$, —$S(O)_m$—$R^a$ or —$S(O)_m$—$NR^aR^b$, or $R^9$ and $R^{10}$ taken together with the nitrogen atom to which they are attached are joined together to form an optionally substituted 3 to 7 membered saturated or unsaturated cyclic ring, which may optionally include at least two heteroatoms selected from O, $NR^e$ or S;

each occurrence of $R^a$ and $R^b$ independently is hydrogen, —$OR^c$, —$SR^c$, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —C(=L)-$R^c$, —C(O)O—$R^c$, —C(O)$NR^cR^d$, —$S(O)$ $R^c$, —$S(O)_m$—$NR^cR^d$, —$NR^cR^d$, or a protecting group, or $R^a$ and $R^b$ taken together with the nitrogen atom to which they are attached are joined together to form an optionally substituted 3 to 7 membered saturated or unsaturated cyclic ring, which may optionally include at least two heteroatoms selected from O, $NR^e$ or S;

each occurrence of $R^c$ and $R^d$ is independently hydrogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heterocyclic group, substituted or unsubstituted heterocyclylalkyl, or a substituted or unsubstituted heteroarylalkyl or a protecting group, or $R^c$ and $R^d$ taken together with the nitrogen atom to which they are attached may be joined to form an optionally substituted 3 to 7 membered saturated or unsaturated cyclic ring, which may optionally include at least two heteroatoms selected from O, $NR^e$ or S;

each occurrence of $R^e$ is independently hydrogen or substituted or unsubstituted alkyl;

each occurrence of L is independently O, S, or $NR^e$;

each occurrence of m is independently 0, 1, or 2; and n is an integer from 0 to 4.

According to one embodiment, the compound meets one or more of criteria (1)-(4) below.

(1) when one of $R^7$ and $R^8$ is hydrogen, the other is not substituted or unsubstituted phenyl, substituted or unsubstituted thienyl or substituted or unsubstituted 2-, 3- or 4-pyridyl;

(2) (a) the bicyclic ring in formula I is not substituted at the 6-position with $—S(O)_2NR^aR^b$ or $—S(O)_2NR^9R^{10}$, or
  (b) when the bicyclic ring in formula I is substituted at the 6-position with $—S(O)_2NR^aR^b$ or $—S(O)_2NR^9R^{10}$, then $R^a$ is hydrogen and $R^b$ is methyl, and $R^9$ is hydrogen and $R^{10}$ is methyl;

(3) (a) $R^3$ and $R^4$ are not $—OR^9$, when $R^9$ is hydrogen, substituted or unsubstituted alkyl, substituted or unsubstituted arylalkyl, substituted or unsubstituted cycloalkyl, substituted or unsubstituted cycloalkylalkyl, or acyl,
  (b) $R^3$ and $R^4$ are not $—OR^9$, or
  (c) when $R^5$ is $—NR^9R^{10}$ and $R^9$ is $C(=L)-R^a$, then $R^a$ is not substituted or unsubstituted phenyl, napthyl, pyridyl, pyrimidyl, pyrrolyl, furyl, thienyl, indolyl, pyrrolidinolinyl, piperidonlyl, azepeneonlyl, or pyridazinone;

(4) $R^1$ and $R^2$ together form an optionally substituted 3 to 7 membered saturated or unsaturated cyclic ring, which may optionally include one or more heteroatoms selected from O, $NR^9$ or $S(O)_m$.

According to one preferred embodiment, the compound meets all of criteria (1)-(4) above. According to another preferred embodiment, the compound meets criteria (4).

According to another embodiment, none of the $R^5$ groups are $—S(O)_2NR^aR^b$ or $—S(O)_2NR^9R^{10}$.

These compounds may include one or more of the following embodiments. For example, X can be O or $S(O)_m$, [wherein m can be 0 or 2]; $R^1$ and $R^2$ together may form an optionally substituted 3 to 7 membered saturated or unsaturated cyclic ring, which may optionally include one or more heteroatom(s) selected from O, $NR^9$ or $S(O)_m$; $R^3$, $R^4$, $R^6$ and $R^7$ can be hydrogen; in each occurrence $R^5$ can be independently hydrogen, halogen, nitro, cyano, substituted or unsubstituted alkyl, $OR^9$, $NR^9R^{10}$ or $S(O)_mR^9$; $R^8$ can be heteroaryl, heteroarylalkyl, heterocyclyl or arylalkyl; further, $R^7$ and $R^8$, together with the nitrogen atom to which they are attached, may form a saturated or unsaturated $C_3-C_7$ cyclic ring which may optionally contain one or more hereroatom(s); and Y can be O or S.

A preferred compound of formula (I) is where X is O.

Another preferred compound of formula (I) is where X is S.

Further preferred is a compound of formula (I) where Y is O.

Further preferred is a compound of formula (I) where $R^1$ and $R^2$ are joined together with the carbon atom to which they are bound to form an optionally substituted 3 to 7 member saturated cyclic ring, which may optionally include a heteroatom selected from O and $NR^9$.

Further preferred is a compound of formula (I) where $R^1$ and $R^2$ are joined together with the carbon atom to which they are bound to form a cyclobutane ring.

Further preferred is a compound of formula (I) where $R^3$ and $R^4$ are independently hydrogen, cyano, halogen, $—OR^9$, substituted or unsubstituted alkyl or $—NR^9R^{10}$.

Further preferred is a compound of formula (I) where $R^3$ and $R^4$ are hydrogen.

Further preferred is a compound of formula (I) where each occurrence of $R^5$ is selected from hydrogen, halogen, unsubstituted alkyl (e.g., methyl) and $—OR^9$ (where $R^9$ is unsubstituted alkyl or alkyl substituted with halogen) (e.g., $—OCH_3$ or $—OCHF_2$).

Further preferred is a compound of formula (I) where $R^5$ is hydrogen.

Further preferred is a compound of formula (I) where $R^6$ is hydrogen.

Further preferred is a compound of formula (I) where $R^7$ is hydrogen.

Further preferred is a compound of formula (I) where $R^3$, $R^4$, $R^5$, $R^6$ and $R^7$ are hydrogen.

Further preferred is a compound of formula (I) where $R^1$ and $R^2$ are joined together to form a cyclobutyl ring, and $R^3$-$R^7$ are hydrogen.

Further preferred is a compound of formula (J) where $R^8$ is substituted or unsubstituted arylalkyl, substituted or unsubstituted heteroaryl, substituted or unsubstituted heteroarylalkyl, or substituted or unsubstituted heterocyclyl.

Further preferred is a compound of formula (I) where $R^8$ is pyrrolidinyl-3-yl.

Further preferred is a compound of formula (I) where $R^8$ is quinolin-5-yl.

Further preferred is a compound of formula (I) where $R^8$ is isoquinolin-8-yl.

Further preferred is a compound of formula (I) where $R^8$ is (pyridin-4-yl)methyl.

Further preferred is a compound of formula (I) where $R^8$ is 4-trifluoromethylbenzyl.

Further preferred is a compound of formula (I) where $R^5$ is substituted with a substituted or unsubstituted heteroaryl, such as 4-trifluoromethylpyridin-2-yl.

Further preferred is a compound of formula (I) where $R^7$ and $R^8$ are joined together with the nitrogen atom to which they are bound to form an optionally substituted 3 to 7 membered saturated or unsaturated cyclic ring, which may optionally include one or more heteroatoms selected from O, $NR^e$ or S;

Further preferred is a compound of formula (I) where $R^7$ and $R^8$ are combined to form piperidine.

According to one embodiment, $R^1$ and $R^2$ together with the carbon atom to which they are bound do not form a cyclopentyl or cyclohexyl ring.

According to one preferred embodiment, the vanilloid receptor ligands have the formula:

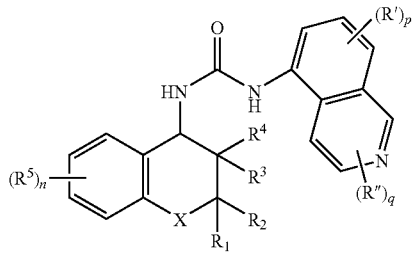

(IIb)

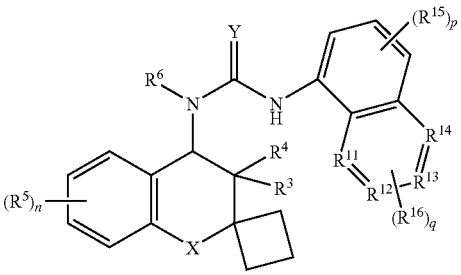

(IV)

wherein:

R$^1$, R$^2$, R$^3$, R$^4$, R$^5$ and n are as defined above;

R' and R" are independently hydrogen, nitro, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —OR$^9$, —NR$^9$R$^{10}$, —C(=L)-R$^9$, —C(O)O—R$^9$, —C(O)NR$^9$R$^{10}$, —S(O), —R$^9$, or —S(O)$_m$—NR$^9$R$^{10}$;

p and q are independently 0, 1, 2, or 3, and pharmaceutically acceptable salts thereof, pharmaceutically acceptable solvates thereof, hydrates thereof, N-oxides thereof, tautomers thereof, stereoisomers thereof, prodrugs thereof and polymorphs thereof. X is preferably O or S. According to one embodiment, X is O.

According to another embodiment, the compound of formula IIb meets the criteria (3) mentioned above.

According to another preferred embodiment, the VR1 receptor ligands of the invention have the formula:

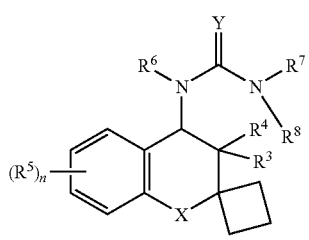

(III)

wherein X, Y, R$^3$-R$^8$, and n are as defined above, and pharmaceutically acceptable salts thereof, pharmaceutically acceptable solvates thereof, hydrates thereof, N-oxides thereof, tautomers thereof, stereoisomers thereof, prodrugs thereof and polymorphs thereof. X and Y are preferably O. R$^8$ is preferably a substituted or unsubstituted quinolinyl or isoquinolinyl. More preferably, the quinolinyl or isoquinolinyl group is attached to the main structure of the compound at a position on the carbon-only cyclic ring. X is preferably O or S. According to one embodiment, X is O. Y is preferably O.

According to one embodiment, the compound of formula III meets the criteria (1), (2) or (3) mentioned above, or any combination thereof.

According to a more preferred embodiment, the VR1 receptor ligands of the invention have the formula:

wherein:

X, Y, R$^3$, R$^4$, R$^6$, R$^9$, R$^{10}$, n, p, and q are as defined above;

one of R$^{11}$-R$^{14}$ is N and the remaining R$^{11}$-R$^{14}$ groups are CH or CR$^a$;

each occurrence of R$^5$ is independently hydrogen, nitro, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —OR$^9$, —NR$^9$R$^{10}$, —C(=L)-R$^9$, —C(O)O—R$^9$, or —C(O)NR$^9$R$^{10}$; and each occurrence of R$^{15}$ and R$^{16}$ is independently hydrogen, nitro, cyano, halogen, substituted or unsubstituted alkyl, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted aryl, substituted or unsubstituted arylalkyl, substituted or unsubstituted heteroaryl, substituted or unsubstituted heteroarylalkyl, substituted or unsubstituted heterocyclic group, substituted or unsubstituted heterocyclylalkyl, —OR$^9$, —NR$^9$R$^{10}$, —C(=L)-R$^9$, —C(O)O—R$^9$, —C(O)NR$^9$R$^{10}$, —S(O)$_m$—R$^9$, or —S(O)$_m$—NR$^9$R$^{10}$;

and pharmaceutically acceptable salts thereof, pharmaceutically acceptable solvates thereof, hydrates thereof, N-oxides thereof, tautomers thereof, stereoisomers thereof, prodrugs thereof and polymorphs thereof. X is preferably O or S. According to one embodiment, X is O. Y is preferably O.

According to one embodiment, the compound of formula IV meets the criteria (3) mentioned above.

Representative compounds of the present invention include those specified below and pharmaceutically acceptable salts, pharmaceutically acceptable solvates, N-oxides, stereoisomers, tautomers, prodrugs or polymorphs thereof. The present invention should not be construed to be limited to them.

(±) 1-{3,4-Dihydro-1'-(methyl)spiro-[2H-1-benzopyran-2,4'-piperidine]-4-yl}-3-(isoquinoline-5-yl)urea (Compound No. 1), (±) 1-(2',3,3',4,5',6'-Hexahydrospiro-[2H-1-benzopyran-2,4'-pyran]-4-yl)-3-(isoquinoline-5-yl)urea (Compound No. 2), (±) 1-(3,4-Dihydro-spiro-[2H-1-benzopyran-2,1'-cyclobutan]-4-yl)-3-(isoquinolin-5-yl)urea (Compound No. 3), (+) 1-(3,4-Dihydro-spiro-[2H-1-benzopyran-2,1'-cyclobutan]-4-yl)-3-(isoquinolin-5-yl)urea (Compound No. 4), (−) 1-(3,4-Dihydro-spiro-[2H-1-benzopyran-2,1'-cyclobutan]-4-yl)-3-(isoquinolin-5-yl)urea (Compound No. 5), (±) 1-(3,4-dihydro-spiro[2H-1-benzopyran-2,1'-cyclobutane]-4-yl)-3-(8-chloroisoquinolin-5-yl)urea (Compound No. 6), (±) 1-(3,4-Dihydro-spiro[2H-1-benzopyran-2,1'-cyclobutane]-4-yl)-3-(3-methylisoquinolin-5-yl)urea (Compound No. 7), (±) 1-(3,4-Dihydro-spiro[2H-1-benzopyran-2,1'-cyclobutane]-4-yl)-3-(1-methylisoquinolin-5-yl)urea (Compound No. 8), (±) 1-(3,4-Dihydro-spiro[2H-1-benzopyran-2,1'-cyclobutane]-4-yl)-3-(2-oxoisoquinolin-5-yl)urea (Compound No. 9), (+) 1-(3,4-Dihydro-spiro[2H-1-benzopyran-2,1'-cyclobutane]-4-yl)-3-(2-oxoisoquinolin-5-yl)urea (Compound No. 10), (−) 1-(3,4-Dihydro-spiro[2H-1-benzopyran-2,1'-cyclobutane]-4-yl)-3-(pyridin-3-ylmethyl)urea (Compound No. 11), (±) 1-(3,4-Dihydro-spiro[2H-1-benzopyran-2,1'-cyclobutane]-4-yl)-3-(pyridin-2-yl methyl)urea (Compound No. 12), (±) 1-(3,4-Dihydro-spiro[2H-1-benzopyran-2,1'-cyclobutane]-4-yl)-3-(6-chloro-1,3-benzothiazol-2-yl)urea (Compound No. 13), (±) 1-(3,4-Dihydro-spiro[2H-1-benzopyran-2,1'-cyclobutane]-4-yl)-3-(6-fluoro-1,3-benzothiazol-2-yl)urea (Compound No. 14), (±) 1-(3,4-Dihydro-spiro[2H-1-benzopyran-2,1'-cyclobutane]-4-yl)-3-(1-methyl-1H-indazol-5-yl)urea (Compound No. 15), (±) 1-(3,4-Dihydro-spiro[2H-1-benzopyran-2,1'-cyclobutane]-4-yl)-3-(6-methoxy-1,3-benzothiazol-2-yl)urea (Compound No. 16), (±) 1-(3,4-Dihydro-spiro[2H-1-benzopyran-2,1'-cyclobutane]-4-yl)-3-(2-methyl-2H-indazol-5-yl)urea (Compound No. 17), (−) 1-(3,4-Dihydro-spiro[2H-1-benzopyran-2,1'-cyclobutane]-4-yl)-3-(5-tert-butyl-1,3,4-thiadiazol-2-yl)urea (Compound No. 18), (±) 1-(3,4-Dihydro-spiro[2H-1-benzopyran-2,1'-cyclobutane]-4-y-bromophenyl)-1,3-thiazol-2-yl])urea (Compound No. 19), (±) 1-(3,4-Dihydro-spiro[2H-1-benzopyran-2,1'-cyclobutane]-4-yl)-3-(6-methyl-1,3-benzothiazol-2-yl)urea (Compound No. 20), (±) 1-(3,4-Dihydro-spiro[2H-1-benzopyran-2,1'-cyclobutane]-4-yl)-3-(1-acetyl-1H-indazol-5-yl)urea (Compound No, 21), (±) 1-(3,4-Dihydro-spiro[2H-1-benzopyran-2,1'-cyclobutane]-4-yl)-3-(thieno[2,3-c]pyridine-3-yl)urea (Compound No. 22), (±) 1-(3,4-Dihydro-spiro[2H-1-benzopyran-2,1'-cyclobutane]-4-yl)-3-([5-(4-bromophenyl)-1,3,4-thiadiazol-2-yl]-)urea (Compound No. 23), (±) 1-(3,4-Dihydro-spiro[2H-1-benzopyran-2,1'-cyclobutane]-4-yl)-3-(4,6-dimethylpyrimidin-2-yl)urea (Compound No. 24), (±) 1-(3,4-Dihydro-spiro[2H-1-benzopyran-2,1'-cyclobutane]-4-yl)-3-(5-chloro-1,3-benzoxazol-2-yl)urea (Compound No. 25), (±) 1-(3,4-Dihydro-spiro[2H-1-benzopyran-2,1'-cyclobutane]-4-yl)-3-(5-(4-nitrophenyl)-1,3,4-thiadiazol-2-yl)urea (Compound No. 26), (±) 1-(3,4-Dihydro-spiro[2H-1-benzopyran-2,1'-cyclobutane]-4-yl)-3-(2-furylmethyl)urea (Compound No. 27), (±) 1-(3,4-Dihydrospiro[2H-1-benzopyran-2,1'-cyclobutan]-4-yl)-3-(quinolin-5-yl)urea (Compound No. 28), (±) 1-(3,4-Dihydrospiro[2H-1-benzopyran-2,1'-cyclobutan]-4-yl)-3-(isoquinolin-8-yl)urea (Compound No. 29), 1-((R)-3,4-Dihydrospiro[2H-1-benzopyran-2,1'-cyclobutan]-4-yl)-3-((S)-1-(4-trifluoromethylpyridin-2-yl)pyrrolidin-3-yl)urea (Compound No. 30), 1-((R)-3,4-Dihydrospiro[2H-1-benzopyran-2,1'-cyclobutan]-4-yl)-3-((R)-1-(4-trifluoromethylpyridin-2-yl)pyrrolidin-3-yl)urea (Compound No. 31), 1-((S)-3,4-Dihydrospiro[2H-1-benzopyran-2,1'-cyclobutan]-4-yl)-3-((R)-1-(4-trifluoromethylpyridin-2-yl)pyrrolidin-3-yl)urea (Compound No. 32), 1-((S)-3,4-Dihydrospiro[2H-1-benzopyran-2,1'-cyclobutan]-4-yl)-3-((S)-1-(4-trifluoromethylpyridin-2-yl)pyrrolidin-3-yl)urea (Compound No. 33), 1-((S)-3,4-Dihydrospiro[2H-1-benzopyran-2,1'-cyclobutan]-4-yl)-3-(pyridin-4-yl)methyl urea (Compound No. 34), 1-((S)-3,4-Dihydrospiro[2H-1-benzopyran-2,1'-cyclobutan]-4-yl)-3-(4-trifluoromethylbenzyl)urea (Compound No. 35), N-3,4-dihydrospiro[chromene-2,1'-cyclobutan]-4-ylpiperidine-1-carboxamide (Compound No. 36), N-2,1,3-benzothiadiazol-4-yl-N'-3,3',4,4'-tetrahydro-2'H-spiro[chromene-2,1'-cyclobutan]-4-ylurea (N-2,1,3-benzothiadiazol-4-yl-N'-3,4-dihydro-2H-spiro[chromene-2,1'-cyclobutan]-4-ylurea) (Compound No. 37), N-2,1,3-benzothiadiazol-4-yl-N'-3,3',4,4'-tetrahydro-2'H-spiro[chromene-2,1'-cyclobutan]-4-ylurea (N-2,1,3-benzothiadiazol-4-yl-N'-3,4-dihydro-2H-spiro[chromene-2,1'-cyclobutan]-4-ylurea) (Compound No. 38), N'-(1-oxo-1,2-dihydroisoquinolin-5-yl)-N-3,3',4,4'-tetrahydro-2'H-spiro[chromene-2,1'-cyclobutan]-4-ylurea (N'-(1-oxo-1,2-dihydroisoquinolin-5-yl)-N-3,4-dihydro-2H-spiro[chromene-2,1'-cyclobutan]-4-ylurea) (Compound No. 39), (±) 1-(3,4-Dihydro-6-methyl-spiro[2H-1-benzopyran-2,1'-cyclobutane]-4-yl)-3-(isoquinolin-5-yl)urea (Compound No. 40), (±) 1-(3,4-Dihydro-7-methyl-spiro[2H-1-benzopyran-2,1'-cyclobutane]-4-yl)-3-(isoquinolin-5-yl)urea (Compound No. 41), (±) 1-(3,4-Dihydro-6-fluoro-spiro[2H-1-benzopyran-2,1'-cyclobutane]-4-yl)-3-(isoquinolin-5-yl)urea (Compound No. 42), (+) 1-(3,4-Dihydro-6-fluoro-spiro[2H-1-benzopyran-2,1'-cyclobutane]-4-yl)-3-(isoquinolin-5-yl)urea (Compound No. 43), (−) 1-(3,4-Dihydro-6-fluorospiro[2H-1-benzopyran-2,1'-cyclobutane]-4-yl)-3-(isoquinolin-5-yl)urea (Compound No. 44), (±) 1-(3,4-Dihydro-6-hydroxy-spiro[2H-1-benzopyran-2,1'-cyclobutane]-4-yl)-3-(isoquinolin-5-yl)urea (Compound No. 45), (±) 1-(3,4-Dihydro-7-hydroxy-spiro[2H-1-benzopyran-2,1'-cyclobutane]-4-yl)-3-(isoquinolin-5-yl)urea (Compound No. 46), (±) 1-(3,4-Dihydro-7-methoxy-spiro[2H-1-benzopyran-2,1'-cyclobutane]-4-yl)-3-(isoquinolin-5-yl)urea (Compound No. 47), 1-(6,8-Difluoro-3,4-dihydro-spiro[2H-1-benzopyran-2,1'-cyclobutane]-4-yl)-3-(isoquinolin-5-yl)urea (Compound No. 48), (±) 1-(8-Chloro-3,4-dihydro-spiro[2H-1-benzopyran-2,1'-cyclobutane]-4-yl)-3-(isoquinolin-5-yl)urea (Compound No. 49), (±) 1-(3,4-Dihydro-6-fluoro-spiro[2H-1-benzopyran-2,1'-cyclobutane]-4-yl)-3-(isoquinolin-5-yl)urea (Compound No. 50), (±) 1-(3,4-Dihydro-6-methoxy-spiro[2H-1-benzopyran-2,1'-cyclobutane]-4-yl)-3-(isoquinolin-5-yl)urea (Compound No. 51), (±) 1-(6-Cyclopentyloxy-3,4-dihydro-spiro[2H-1-benzopyran-2,1'-cyclobutane]-4-yl)-3-(isoquinolin-5-yl)urea (Compound No. 52), (±) 1-(7-Cyclopentyloxy-3,4-dihydro-spiro[2H-1-benzopyran-2,1'-cyclobutane]-4-yl)-3-(isoquinolin-5-yl)urea (Compound No. 53), (±) 1-(7-Difluoromethoxy-3,4-dihydro-spiro[2H-1-benzopyran-2,1'-cyclobutane]-4-yl)-3-(isoquinolin-5-yl)urea. Hydrochloride salt (Compound No. 54), (±) 1-(3,4-Dihydro-6-methylaminosulfonyl-spiro[2H-1-benzopyran-2,1'-cyclobutane]-4-yl)-3-(isoquinolin-5-yl)urea (Compound No. 55), (±) 1-(7-Difluoromethoxy-3,4-dihydro-spiro[2H-1-benzopyran-2,1'-cyclobutane]-4-yl)-3-(3-methylisoquinolin-5-yl)urea (Compound No. 56), (±) 1-(7-Chloro-3,4-dihydro-spiro[2H-1-benzopyran-2,1'-cyclobutane]-4-yl)-3-(3-methylisoquinolin-5-yl)urea (Compound No. 57), (±) 1-(8-Cyano-3,4-dihydro-spiro[2H-1-benzopyran-2,1'-cyclobutane]-4-yl)-3-(isoquinolin-5-yl)urea (Compound No. 58), (+) 1-(6,8-Difluoro-3,4-Dihydro-spiro[2H-1-benzopyran-2,1'-cyclobutane]-4-yl)-3-(isoquinolin-5-yl)urea (Compound No. 59), (−) 1-(6,8-Difluoro-3,4-Dihydro-spiro[2H-1-benzopyran-2,1'-cyclobutane]-4-yl)-3-(isoquinolin-5-yl)urea (Compound No. 60), (±) 1-(3,4-Dihydro-8-hydroxy-spiro[2H-1-benzopyran-2,1'-cyclobutane]-4-yl)-3-(isoquinolin-5-yl)urea (Compound No. 61), (±) 1-(3,4-Dihydro-8-difluoromethoxy-spiro[2H-1-benzopyran-2,1'-cyclobutane]-4-yl)-3-(isoquinolin-5-yl)urea (Compound No. 62), (±) 1-(6-Chloro-3,4-dihydro-spiro[2H-1-benzopyran-2,1'-cyclobutane]-4-yl)-3-(isoquinolin-5-yl)urea (Compound No. 63), (−) 1-(6-Chloro-3,4-dihydro-spiro[2H-1-benzopyran-2,1'-cyclobutane]-4-yl)-3-(isoquinolin-5-yl)urea (Compound No. 64), (±) 1-(6-Bromo-3,4-dihydro-spiro[2H-1-benzopyran-2,1'-cyclobutane]-4-yl)-3-(isoquinolin-5-yl)urea (Compound No. 65), (±) 1-(6,8-Dichloro-3,4-dihydro-spiro[2H-1-benzopyran-2,1'-cyclobutane]-4-yl)-3-(isoquinolin-5-yl)urea (Compound No. 66), (±) 1-(6-Bromo-3,4-dihydro-7-methylspiro[2H-1-benzopyran-2,1'-cyclobutane]-4-yl)-3-(isoquinolin-5-yl)urea (Compound No. 67), (±) 1-(6,7-Dichloro-3,4-dihydro-spiro[2H-1-benzopyran-2,1'-cyclobutane]-4-yl)-3-(isoquinolin-5-yl)urea (Compound No. 68), (±) 1-(6-Chloro-3,4-dihydro-7-methyl-spiro[2H-1-benzopyran-2,1'-cyclobutane]-4-yl)-3-(isoquinolin-5-yl)urea (Compound No. 69), (±) 1-(6-Chloro-3,4-dihydro-spiro[2H-1-benzopyran-2,1'-cyclobutane]-4-yl)-3-(8-chloroisoquinolin-5-yl)urea (Compound No. 70), (±) 1-(6-Fluoro-3,4-dihydro-spiro[2H-1-benzopyran-2,1'-cyclobutane]-4-yl)-3-(8-chloroisoquinolin-5-yl)urea (Compound No. 71), (±) 1-(3,4-Dihydro-6-fluoro-spiro[2H-1-benzopyran-2,1'-cyclobutane]-4-yl)-3-(3-methylisoquinolin-5-yl)urea (Compound No. 72), (±) 1-(6-Chloro-3,4-dihydro-spiro[2H-1-benzopyran-2,1'-cyclobutane]-4-yl)-3-(3-methylisoquinolin-5-yl)urea (Compound No. 73), (±) 1-(6-Chloro-3,4-dihydro-spiro[2H-1-benzopyran-2,1'-cyclobutane]-4-yl)-3-(1-methylisoquinolin-5-yl)urea (Compound No. 74), (±) 1-(3,4-Dihydro-6-fluoro-spiro[2H-1-benzopyran-2,1'-cyclobutane]-4-yl)-3-(1-methylisoquinolin-5-yl)urea (Compound No. 75), (±) 1-(6-Acetamido-3,4-dihydro-spiro[2H-1-benzopyran-2,1'-cyclobutane]-4-yl)-3-(isoquinolin-5-yl)urea (Compound No. 76), (±) 1-(6-Amino-3,4-dihydro-spiro[2H-1-benzopyran-2,1'-cyclobutane]-4-yl)-3-(isoquinolin-5-yl)urea (Compound No. 77), (±) 1-(7-Chloro-3,4-dihydro-spiro[2H-1-benzopyran-2,1'-cyclobutane]-4-yl)-3-(isoquinolin-5-yl)urea (Compound No. 78), (±) 1-(3,4-Dihydro-6-nitro-spiro[2H-1-benzopyran-2,1'-cyclobutane]-4-yl)-3-(isoquinolin-5-yl)urea (Compound No. 79), N'-isoquinolin-5-yl-N-3,3',4,4'-tetrahydro-2'H-spiro[chromene-2,1'-cyclobutan]-4-ylthiourea (N'-isoquinolin-5-yl-N-3,4-dihydro-2H-spiro[chromene-2,1'-cyclobutan]-4-ylthiourea) (Compound No. 80), (±) 1-(3,4-dihydro-spiro[2H-1-benzothiopyran-2,1'-cyclobutan]-4-yl)-3-(isoquinolin-5-yl)urea (Compound No. 81), (±) 1-(1,1-dioxo-3,4-dihydro-spiro[2H-1-benzothiopyran-2,1'cyclobutane]-4-yl)-3-(isoquinolin-5-yl)urea (Compound No. 82), and N'-isoquinolin-8-yl-N-3,3',4,4'-tetrahydro-2'H-spiro[chromene-2,1'-cyclobutan]-4-ylthiourea (N'-isoquinolin-8-yl-N-3,4-dihydro-2H-spiro[chromene-2,1'-cyclobutan]-4-ylthiourea) (Compound No. 83).

Also provided herein is a pharmaceutical composition comprising one or more of the aforementioned compounds together with one or more pharmaceutically acceptable excipients (such as a pharmaceutically acceptable carrier or diluent). Preferably, the pharmaceutical composition comprises a therapeutically effective amount of one or more compounds of the present invention. One or more compounds of the present invention may be diluted with carriers or enclosed within a carrier, which can be in the form of a capsule, sachet, paper or other container.

Also provided herein is a method for preventing, ameliorating or treating a disease, disorder or syndrome mediated by vanilloid receptors (such as VR1) in a subject in need thereof by administering to the subject a therapeutically effective amount of one or more compounds of the present invention or a pharmaceutical composition of the present invention. Non-limiting examples of diseases, disorders and syndromes which can be mediated by vanilloid receptor 1 (VR1) include (1) migraine, (2) arthralgia, (3) diabetic neuropathy, (4) neurodegeneration, (5) neurotic skin disorder, (6) stroke, (7) cardiac pain arising from an ischemic myocardium, (8) Huntington's disease, (9) memory deficits, (10) restricted brain function, (11) amyotrophic lateral sclerosis (ALS), (12) dementia, (13) urinary bladder hypersensitiveness, (14) urinary incontinence, (15) vulvodynia, (16) pruritic conditions such as uremic pruritus, (17) irritable bowel syndrome including gastro-esophageal reflux disease, (18) enteritis, (19) ileitis, (20) stomach-duodenal ulcer, (21) inflammatory bowel disease including Crohn's disease, (22) celiac disease,

(23) inflammatory diseases (such as pancreatitis), (24) respiratory disorders such as allergic and non-allergic rhinitis, asthma or chronic obstructive pulmonary disease (COPD), (25) irritation of skin, eye or mucous membrane, (26) dermatitis, (27) fervescence, (28) retinopathy, (29) muscle spasms, (30) emesis, (31) dyskinesias, (32) depression, (33) pain such as acute, chronic, neuropathic pain or post-operative pain, (34) pain due to neuralgia or trigeminal neuralgia, (35) pain due to diabetic neuropathy, (36) dental pain, (37) cancer pain, (38) arthritis, (39) osteoarthritis, (40) diabetes, (41) obesity, (42) urticaria, (43) actinic keratosis, (44) keratocanthoma, (45) alopecia, (46) Meniere's disease, (47) tinnitus, (48) hyperacusis, (49) anxiety disorders and (50) benign prostate hyperplasia. According to one preferred embodiment, the compounds of the present invention are administered to treat acute or chronic pain or neuropathic pain.

Also provided herein are processes for preparing compounds described herein.

DETAILED DESCRIPTION OF THE INVENTION

The present invention provides substituted benzofused derivatives, which can be used as vanilloid receptor ligands, and processes for the synthesis of these compounds. Pharmaceutically acceptable salts, pharmaceutically acceptable solvates, enantiomers, diastereomers, polymorphs of these compounds having the same type of activity are also provided. Pharmaceutical compositions containing the described compounds together with pharmaceutically acceptable carriers, excipients or diluents, which can be used for the treatment of diseases, condition and/or disorders mediated by vanilloid receptors (such as VR1) are further provided.

DEFINITIONS

The term "alkyl" refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "$C_{1-6}$ alkyl" refers to an alkyl chain having 1 to 6 carbon atoms.

The term "alkenyl" refers to an aliphatic hydrocarbon group containing a carbon-carbon double bond and which may be a straight or branched chain having 2 to about 10 carbon atoms, e.g., ethenyl, 1-propenyl, 2-propenyl (allyl), iso-propenyl, 2-methyl-1-propenyl, 1-butenyl, and 2-butenyl.

The term "alkynyl" refers to a straight or branched chain hydrocarbyl radical having at least one carbon-carbon triple bond, and having 2 to about 12 carbon atoms (with radicals having 2 to about 10 carbon atoms being preferred), e.g., ethynyl, propynyl, and butynyl.

The term "alkoxy" denotes an alkyl group attached via an oxygen linkage to the rest of the molecule. Representative examples of such groups are —$OCH_3$ and —$OC_2H_5$.

The term "cycloalkyl" denotes a non-aromatic mono or multicyclic ring system of 3 to about 12 carbon atoms, such as cyclopropyl, cyclobutyl, cyclopentyl, and cyclohexyl. Examples of multicyclic cycloalkyl groups include, but are not limited to, perhydronapthyl, adamantyl and norbornyl groups, bridged cyclic groups or sprirobicyclic groups, e.g., sprio (4,4) non-2-yl.

The term "cycloalkylalkyl" refers to a cyclic ring-containing radical having 3 to about 8 carbon atoms directly attached to an alkyl group. The cycloalkylalkyl group may be attached to the main structure at any carbon atom in the alkyl group that results in the creation of a stable structure. Non-limiting examples of such groups include cyclopropylmethyl, cyclobutylethyl, and cyclopentylethyl.

The term "cycloalkenyl" refers to a cyclic ring-containing radical having 3 to about 8 carbon atoms with at least one carbon-carbon double bond, such as cyclopropenyl, cyclobutenyl, and cyclopentenyl.

The term "aryl" refers to an aromatic radical having 6 to 14 carbon atoms such as phenyl, naphthyl, tetrahydronapthyl, indanyl, and biphenyl.

The term "arylalkyl" refers to an aryl group as defined above directly bonded to an alkyl group as defined above, e.g., —$CH_2C_6H_5$ and —$C_2H_5C_6H_5$.

The term "heterocyclic ring" refers to a stable 3- to 15-membered ring radical which consists of carbon atoms and from one to five heteroatoms selected from nitrogen, phosphorus, oxygen and sulfur. For purposes of this invention, the heterocyclic ring radical may be a monocyclic, bicyclic or tricyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized; and the ring radical may be partially or fully saturated (i.e., heterocyclic or heteroaryl). Examples of such heterocyclic ring radicals include, but are not limited to, azetidinyl, acridinyl, benzodioxolyl, benzodioxanyl, benzoflurnyl, carbazolyl, cinnolinyl, dioxolanyl, indolizinyl, naphthyridinyl, perhydroazepinyl, phenazinyl, phenothiazinyl, phenoxazinyl, phthalazinyl, pyridyl, pteridinyl, purinyl, quinazolinyl, quinoxalinyl, quinolinyl, isoquinolinyl, tetrazoyl, imidazolyl, tetrahydroisouinolyl, piperidinyl, piperazinyl, 2-oxopiperazinyl, 2-oxopiperidinyl, 2-oxopyrrolidinyl, 2-oxoazepinyl, azepinyl, pyrrolyl, 4-piperidonyl, pyrrolidinyl, pyrazinyl, pyrimidinyl, pyridazinyl, oxazolyl, oxazolinyl, oxasolidinyl, triazolyl, indanyl, isoxazolyl, isoxasolidinyl, morpholinyl, thiazolyl, thiazolinyl, thiazolidinyl, isothiazolyl, quinuclidinyl, isothiazolidinyl, indolyl, isoindolyl, indolinyl, isoindolinyl, octahydroindolyl, octahydroisoindolyl, quinolyl, isoquinolyl, decahydroisoquinolyl, benzimidazolyl, thiadiazolyl, benzopyranyl, benzothiazolyl, benzooxazolyl, furyl, tetrahydrofurtyl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heterocyclic ring radical may be attached to the main structure at any heteroatom or carbon atom that results in the creation of a stable structure.

The term "heterocyclyl" refers to a heterocyclic ring radical as defined above. The heterocyclyl ring radical may be attached to the main structure at any heteroatom or carbon atom that results in the creation of a stable structure.

The term "heterocyclylalkyl" refers to a heterocyclic ring radical directly bonded to an alkyl group. The heterocyclylalkyl radical may be attached to the main structure at any carbon atom in the alkyl group that results in the creation of a stable structure.

The term "heteroaryl" refers to an aromatic heterocyclic ring radical. The heteroaryl ring radical may be attached to the main structure at any heteroatom or carbon atom that results in the creation of a stable structure.

The term "heteroarylalkyl" refers to a heteroaryl ring radical directly bonded to an alkyl group. The heteroarylalkyl radical may be attached to the main structure at any carbon atom in the alkyl group that results in the creation of a stable structure.

Unless otherwise specified, the term "substituted" as used herein refers to substitution with any one or any combination of the following substituents: hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenylalkyl, substituted or unsubstituted cycloalkenyl, substituted or unsubstituted amino, substituted or unsubstituted aryl, substituted or unsubstituted heteroaryl, substituted or unsubstituted heterocyclylalkyl ring, substituted or unsubstituted heteroarylalkyl, substituted or unsubstituted heterocyclic ring, substituted or unsubstituted guanidine, —COOR$^x$, —C(O)R$^x$, —C(S)R$^x$, —C(O)NR$^x$R$^y$, —C(O)ONR$^x$R$^y$, —NR$^x$CONR$^y$R$^z$, —NR$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$, —NR$^x$C(S)R$^y$, —NR$^x$C(S)NR$^y$R$^z$, —SONR$^x$R$^y$, —SO$_2$NR$^x$R$^y$, —OR$^x$, —OR$^x$C(O)NR$^y$R$^z$, —OR$^x$C(O)OR$^y$, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^y$, —R$^x$OC(O)R$^y$, —SR$^x$, —SOR$^x$, —SO$_2$R$^x$, and —ONO$_2$, wherein R$^x$, R$^y$ and R$^z$ are independently selected from hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkenyl, substituted or unsubstituted amino, substituted or unsubstituted aryl, substituted or unsubstituted heteroaryl, substituted heterocyclylalkyl ring, substituted or unsubstituted heteroarylalkyl, or substituted or unsubstituted heterocyclic ring. The substituents in the aforementioned "substituted" groups cannot be further substituted. For example, when the substituent on "substituted alkyl" is "substituted aryl", the substituent on "substituted aryl" cannot be "substituted alkenyl".

The term "protecting group" or "PG" refers to a substituent that is employed to block or protect a particular functionality while other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl, benzyl, tetrahydropyranyl and silyl. A "carboxy-protecting group" refers to a substituent of the carboxy group that blocks or protects the carboxy functionality. Suitable carboxy-protecting groups include, but are not limited to, —CH$_2$CH$_2$SO$_2$Ph, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, and nitroethyl. For a general description of protecting groups and their use, see, T. W. Greene, Protective Groups in Organic Synthesis, John Wiley & Sons, New York, 1991.

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

The term "treating" or "treatment" of a state, disorder or condition includes:

(1) preventing or delaying the appearance of clinical symptoms of the state, disorder or condition developing in a subject that may be afflicted with or predisposed to the state, disorder or condition but does not yet experience or display clinical or subclinical symptoms of the state, disorder or condition;

(2) inhibiting the state, disorder or condition, i.e., arresting or reducing the development of the disease or at least one clinical or subclinical symptom thereof; or (3) relieving the disease, i.e., causing regression of the state, disorder or condition or at least one of its clinical or subclinical symptoms.

The benefit to a subject to be treated is either statistically significant or at least perceptible to the subject or to the physician.

The term "subject" includes mammals (especially humans) and other animals, such as domestic animals (e.g., household pets including cats and dogs) and non-domestic animals (such as wildlife).

A "therapeutically effective amount" means the amount of a compound that, when administered to a subject for treating a state, disorder or condition, is sufficient to effect such treatment. The "therapeutically effective amount" will vary depending on the compound, the disease and its severity and the age, weight, physical condition and responsiveness of the subject to be treated.

Pharmaceutically acceptable salts forming part of this invention include salts derived from inorganic bases (such as Li, Na, K, Ca, Mg, Fe, Cu, Zn, and Mn), salts of organic bases (such as N,N'-diacetylethylenediamine, glucamine, triethylamine, choline, hydroxide, dicyclohexylamine, metformin, benzylamine, trialkylamine, and thiamine), salts of chiral bases (such as alkylphenylamine, glycinol, and phenyl glycinol), salts of natural amino acids (such as glycine, alanine, valine, leucine, isoleucine, norleucine, tyrosine, cystine, cysteine, methionine, proline, hydroxy proline, histidine, ornithine, lysine, arginine, and serine), salts of non-natural amino acids (such as D-isomers or substituted amino acids), salts of guanidine, salts of substituted guanidine (wherein the substituents are selected from nitro, amino, alkyl, alkenyl, or alkynyl), ammonium salts, substituted ammonium salts, and aluminum salts. Other pharmaceutically acceptable salts include acid addition salts (where appropriate) such as sulphates, nitrates, phosphates, perchlorates, borates, hydrohalides, acetates (such as trifluoroacetate), tartrates, maleates, citrates, fumarates, succinates, palmoates, methanesulphonates, benzoates, salicylates, benzenesulfonates, ascorbates, glycerophosphates, and ketoglutarates. Yet other pharmaceutically acceptable salts include, but are not limited to, quaternary ammonium salts of the compounds of invention with alkyl halides or alkyl sulphates (such as MeI or (Me)$_2$SO$_4$).

Pharmaceutically acceptable solvates includes hydrates and other solvents of crystallization (such as alcohols). The compounds of the present invention may form solvates with low molecular weight solvents by methods known in the art.

Certain compounds of present invention are capable of existing in stereoisomeric forms (e.g. diastereomers and enantiomers) and the invention extends to each of these stereoisomeric forms and to mixtures thereof including racemates. The different stereoisomeric forms may be separated one from the other by known methods, or any given isomer may be obtained by stereospecific or asymmetric synthesis. The invention also extends to any tautomeric forms and mixtures thereof. For example, both tautomeric forms of the following moiety are contemplated:

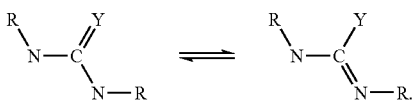

Pharmaceutical Compositions

The pharmaceutical composition of the present invention comprises at least one compound of the present invention and a pharmaceutically acceptable excipient (such as a pharmaceutically acceptable carrier or diluent). Preferably, the pharmaceutical composition comprises a therapeutically effective amount of the compound(s) of the present invention. The compound of the present invention may be associated with a pharmaceutically acceptable excipient (such as a carrier or a diluent) or be diluted by a carrier, or enclosed within a carrier which can be in the form of a capsule, sachet, paper or other container.

Examples of suitable carriers include, but are not limited to, water, salt solutions, alcohols, polyethylene glycols, polyhydroxyethoxylated castor oil, peanut oil, olive oil, gelatin, lactose, terra alba, sucrose, dextrin, magnesium carbonate, sugar, cyclodextrin, amylose, magnesium stearate, talc, gelatin, agar, pectin, acacia, stearic acid or lower alkyl ethers of cellulose, silicic acid, fatty acids, fatty acid amines, fatty acid monoglycerides and diglycerides, pentaerythritol fatty acid esters, polyoxyethylene, hydroxymethylcellulose and polyvinylpyrrolidone.

The carrier or diluent may include a sustained release material, such as glyceryl monostearate or glyceryl distearate, alone or mixed with a wax.

The pharmaceutical composition may also include one or more pharmaceutically acceptable auxiliary agents, wetting agents, emulsifying agents, suspending agents, preserving agents, salts for influencing oxmetic pressure, buffers, sweetening agents, flavoring agents, colorants, or any combination of the foregoing. The pharmaceutical composition of the invention may be formulated so as to provide quick, sustained, or delayed release of the active ingredient after administration to the subject by employing procedures known in the art.

The pharmaceutical compositions of the present invention may be prepared by conventional techniques, e.g., as described in *Remington: The Science and Practice of Pharmacy*, 20$^{th}$ Ed., 2003 (Lippincott Williams & Wilkins). For example, the active compound can be mixed with a carrier, or diluted by a carrier, or enclosed within a carrier, which may be in the form of an ampoule, capsule, sachet, paper, or other container. When the carrier serves as a diluent, it may be a solid, semi-solid, or liquid material that acts as a vehicle, excipient, or medium for the active compound. The active compound can be adsorbed on a granular solid container, for example, in a sachet.

The pharmaceutical compositions may be in conventional forms, for example, capsules, tablets, aerosols, solutions, suspensions or products for topical application.

The route of administration may be any route which effectively transports the active compound of the invention to the appropriate or desired site of action. Suitable routes of administration include, but are not limited to, oral, nasal, pulmonary, buccal, subdermal, intradermal, transdermal, parenteral, rectal, depot, subcutaneous, intravenous, intraurethral, intramuscular, intranasal, ophthalmic (such as with an ophthalmic solution) or topical (such as with a topical ointment). The oral route is preferred.

Solid oral formulations include, but are not limited to, tablets, capsules (soft or hard gelatin), dragees (containing the active ingredient in powder or pellet form), troches and lozenges. Tablets, dragees, or capsules having talc and/or a carbohydrate carrier or binder or the like are particularly suitable for oral application. Preferable carriers for tablets, dragees, or capsules include lactose, cornstarch, and/or potato starch. A syrup or elixir can be used in cases where a sweetened vehicle can be employed.

A typical tablet that may be prepared by conventional tabletting techniques may contain: (1) Core: Active compound (as free compound or salt thereof), 250 mg colloidal silicon dioxide (Aerosil®), 1.5 mg microcrystalline cellulose (Avicel®), 70 mg modified cellulose gum (Ac-Di-Sol®), and 7.5 mg magnesium stearate; (2) Coating: HPMC, approx. 9 mg Mywacett 9-40 T and approx. 0.9 mg acylated monoglyceride Liquid formulations include, but are not limited to, syrups, emulsions, soft gelatin and sterile injectable liquids, such as aqueous or non-aqueous liquid suspensions or solutions.

For parenteral application, particularly suitable are injectable solutions or suspensions, preferably aqueous solutions with the active compound dissolved in polyhydroxylated castor oil.

Methods of Treatment

The present invention provides compounds and pharmaceutical formulations thereof that are useful in the treatment of diseases, conditions and/or disorders modulated by vanilloid VR1 receptor antagonists.

The present invention further provides a method of treating a disease, condition and/or disorder modulated by vanilloid receptor antagonists in a subject in need thereof by administering to the subject a therapeutically effective amount of a compound or a pharmaceutical composition of the present invention. The method is particularly useful for treating diseases, conditions and/or disorders modulated by VR1 receptor antagonists. Diseases, conditions, and/or disorders that are modulated by vanilloid receptor antagonists include, but are not limited to, migraine, arthralgia, diabetic neuropathy, neurodegeneration, neurotic skin disorder, stroke, cardiac pain arising from an ischemic myocardium, Huntington's disease, memory deficits, restricted brain function, amyotrophic lateral sclerosis (ALS), dementia, urinary bladder hypersensitiveness, urinary incontinence, vulvodynia, pruritic conditions such as uremic pruritus, irritable bowel syndrome including gastro-esophageal reflux disease, enteritis, ileitis, stomach-duodenal ulcer, inflammatory bowel disease including Crohn's disease, celiac disease and inflammatory diseases such as pancreatitis, and in respiratory disorders such as allergic and non-allergic rhinitis, asthma or chronic obstructive pulmonary disease, irritation of skin, eye or mucous membrane, dermatitis, and in non specific disorders such as fervescence, retinopathy, muscle spasms, emesis, dyskinesias or depression. Specifically in multiple sub-types of pain such as acute, chronic, neuropathic pain or post-operative pain, as well as in pain due to neuralgia (e.g. post herpetic neuralgia, trigeminal neuralgia; and in pain due to diabetic neuropathy or dental pain as well as in cancer pain. Additionally, VR1 antagonists hold potential benefit in the treatment of inflammatory pain conditions e.g. arthritis, and osteoarthritis, diabetes, obesity, urticaria, actinic keratosis, keratocanthoma, alopecia, Meniere's disease, tinnitus, hyperacusis and anxiety disorders.

The method is also particularly useful for treating pain, urinary incontinence, ulcerative colitis, asthma, and inflammation.

As indicated above, the compounds of the present invention and their pharmaceutically acceptable salts or pharmaceutically acceptable solvates have vanilloid receptor antagonist (VR1) activity and are useful for the treatment or prophylaxis of certain diseases or disorders mediated or associated with the activity of vanilloid receptor, including disorders such as pain, chronic pain, neuropathic pain, postoperative pain, rheumatoid arthritic pain, osteoarthritic pain, back pain, visceral pain, cancer pain, algesia, neuralgia, migraine, neuropathies, diabetic neuropathy, sciatica, HIV-related neuropathy, post-herpetic neuralgia, fibromyalgia, nerve injury, ischaemia, neurodegeneration, stroke, post stroke pain, multiple sclerosis, respiratory diseases, asthma, cough, COPD, inflammatory disorders, oesophagitis, gastroeosophagal reflux disorder (GERD), irritable bowel syndrome, inflammatory bowel disease, pelvic hypersensitivity, urinary incontinence, cystitis, burns, psoriasis, emesis, stomach duodenal ulcer and pruritus.

Thus the invention also provides a compounds or a pharmaceutically acceptable salt thereof, for use as an active therapeutic substance, in particular in the treatment or prophylaxis of diseases or disorders mediated or associated with the activity of vanilloid receptor. In particular the invention provides a compound of formula (I') or a pharmaceutically acceptable salt thereof for use in the treatment or prophylaxis of pain.

The invention further provides a method of treatment or prophylaxis of diseases or disorders mediated or associated with the activity of vanilloid receptor, in mammals including humans, which comprises administering to the sufferer a therapeutically effective amount of a compound of the present invention.

The invention provides for the use of a compound of the present invention or a pharmaceutically acceptable salt thereof or a pharmaceutically acceptable solvate thereof in the manufacture of a medicament for the treatment or prophylaxis of diseases or disorders mediated or associated with the activity of vanilloid receptor.

The compound of the present invention has potent analgesic and antiinflammatory activity, and the pharmaceutical composition of the present invention thus may be employed to alleviate or relieve acute, chronic or inflammatory pains, suppress inflammation, or treat urinary incontinence (including urgent urinary incontinence).

In accordance with another aspect of the present invention, there is also provided a method for alleviating and/or treating migraine, arthralgia, diabetic neuropathy, neurodegeneration, neurotic skin disorder, stroke, cardiac pain arising from an ischemic myocardium, Huntington's disease, memory deficits, restricted brain function, amyotrophic lateral sclerosis (ALS), dementia, urinary bladder hypersensitiveness, urinary incontinence, vulvodynia, pruritic conditions such as uremic pruritus, irritable bowel syndrome including gastroesophageal reflux disease, enteritis, ileitis, stomach-duodenal ulcer, inflammatory bowel disease including Crohn's disease, celiac disease and inflammatory diseases such as pancreatitis, and in respiratory disorders such as allergic and non-allergic rhinitis, asthma or chronic obstructive pulmonary disease, irritation of skin, eye or mucous membrane, dermatitis, and in non specific disorders such as fervescence, retinopathy, muscle spasms, emesis, dyskinesias or depression. Specifically in multiple sub-types of pain such as acute, chronic, neuropathic pain or post-operative pain, as well as in pain due to neuralgia (e.g. post herpetic neuralgia, trigeminal neuralgia; and in pain due to diabetic neuropathy or dental pain as well as in cancer pain. Additionally in the treatment of inflammatory pain conditions e.g. arthritis, and osteoarthritis, diabetes, obesity, urticaria, actinic keratosis, keratocanthoma, alopecia, Meniere's disease, tinnitus, hyperacusis and anxiety disorders.

The compounds of the present invention in pharmaceutical dosage forms may be used in the form of their pharmaceutically acceptable salts, and also may be used alone or in appropriate association, as well as in combination with other pharmaceutically active compounds.

The compounds of the present invention (including the pharmaceutical compositions and processes used therein) may be used alone or in combination with other pharmaceutical agents in the manufacture of a medicament for the therapeutic applications described herein.

Methods of Preparation

The compounds of Formula I can be prepared by schemes 1, 2, 3, 4 and 5 shown below.

Scheme I

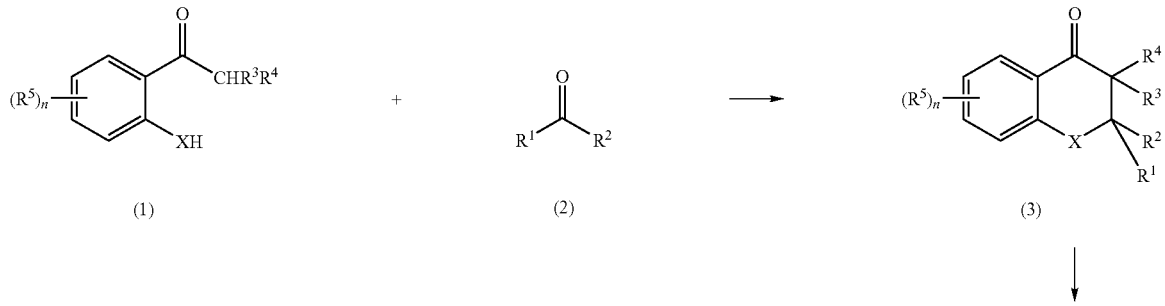

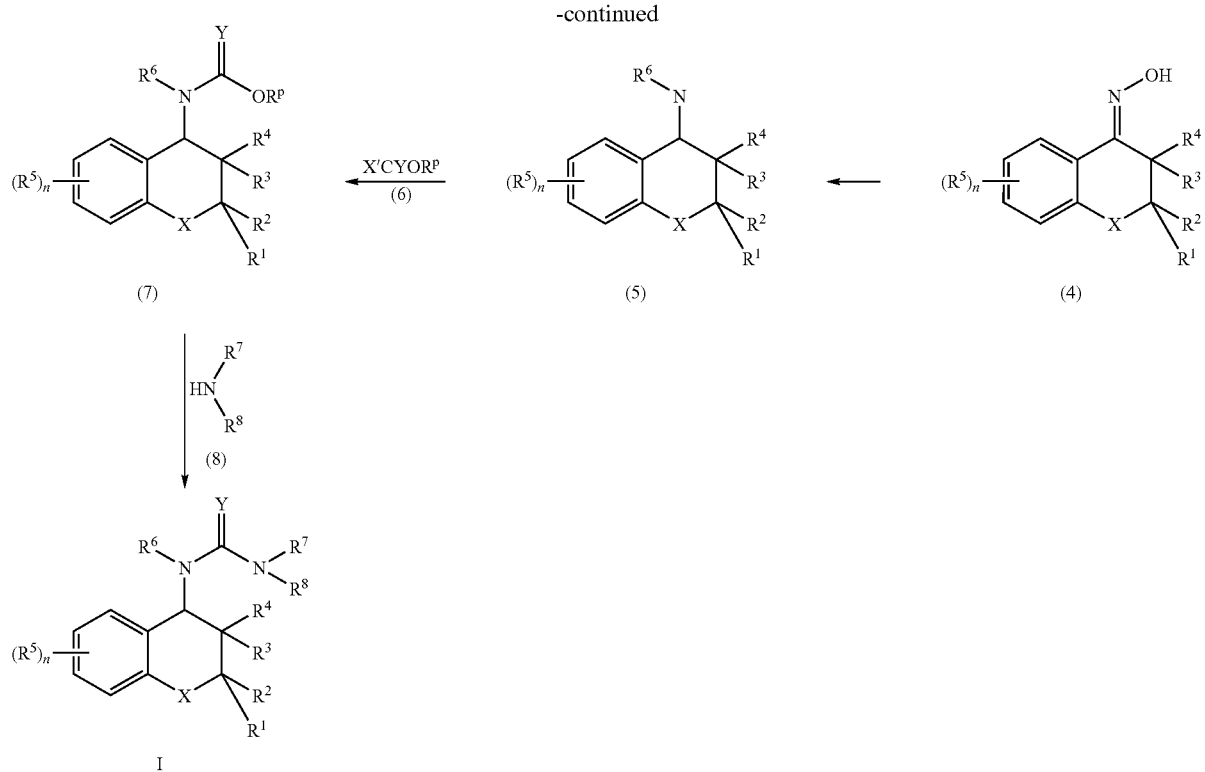

A compound of Formula I can be prepared by the above Scheme I. The compound of Formula (I) is reacted with compound of Formula (2) to form the bicyclic compound of Formula (3). The oxo group of Formula (3) is converted to an oxime group, such as by reaction with hydroxylamine hydrochloride, forming a compound of Formula (4). The oxime group of the compound of Formula (4) is reduced to an amine group, forming the compound of Formula (5).

The compound of Formula (5) is acylated, such as with a formate of the Formula (6) X'CYOR$^p$ where X' is a leaving group (such as a halogen) and R$^p$ is hydrogen, alkyl or aryl (e.g., phenyl) (such as phenylchloroformate), to form the compound of Formula (7). The compound of formula (7) is reacted with an amine of Formula (8) to form a compound of Formula I.

The compound of Formula (I) can be reacted with a compound of Formula (2) in one or more suitable organic base including, but not limited to, pyrrolidine, morpholine, pyridine or mixtures thereof. The compound of Formula (I) can also be reacted in one or more solvents including, but not limited to, polar protic solvents (e.g., methanol, ethanol, isopropylalcohol and mixtures thereof), aprotic polar solvents (e.g., dichloromethane, acetonitrile, dichloroethane, tetrahydrofuran, dibromomethane and mixtures thereof), and mixtures thereof. The compound of Formula (3) can be reacted with hydroxylamine hydrochloride in one or more suitable solvent including, but not limited to, polar protic solvents (e.g., methanol, ethanol, isopropylalcohol and mixtures thereof), aprotic polar solvents (e.g., dichloromethane, dichloroethane, tetrahydrofuran, dibromomethane and mixtures thereof), and mixtures thereof. The compound of Formula (4) can be reduced to form an amine of Formula (5) in the presence of reducing agents including, but not limited to, catalytic reducing agents (e.g., Nickel-Aluminum/hydrogen, palladium-carbon/hydrogen, platinum-carbon/hydrogen, Raney-Nickel/hydrogen or mixtures thereof) and boron reagents (e.g. sodium borohydride, sodium cyanoborohydride, BH$_3$.THF, BH$_3$-dimethylsulfide and mixtures thereof).

The compound of Formula (5) can be reacted with a compound of Formula (6) [wherein R$^p$ can be alkyl or aryl] in one or more suitable solvent including, but not limited to, polar protic solvents (e.g., methanol, ethanol, isopropylalcohol and mixtures thereof), aprotic polar solvents (e.g., dichloromethane, dichloroethane, tetrahydrofuran, dibromomethane and mixtures thereof), and mixtures thereof.

The compound of Formula (6) can be reacted with a compound of Formula (8) in the presence of a base including, but not limited to, potassium bicarbonate, potassium carbonate, sodium carbonate, sodium bicarbonate, triethylamine, ammonium hydroxide, pyridine, alkylamines and mixtures thereof, in one or more suitable solvents, not limited to, polar protic solvents (e.g., methanol, ethanol, isopropylalcohol and mixtures thereof), aprotic polar solvents (e.g., dichloromethane, dichloroethane, tetrahydrofuran, dibromomethane dimethylsulfoxide, dimethylformamide and mixtures thereof), and mixtures thereof.

Scheme (II)

Step 1

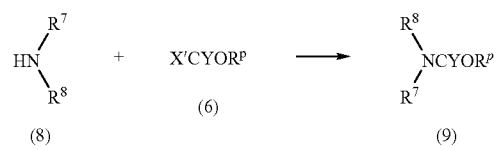

-continued

Step 2

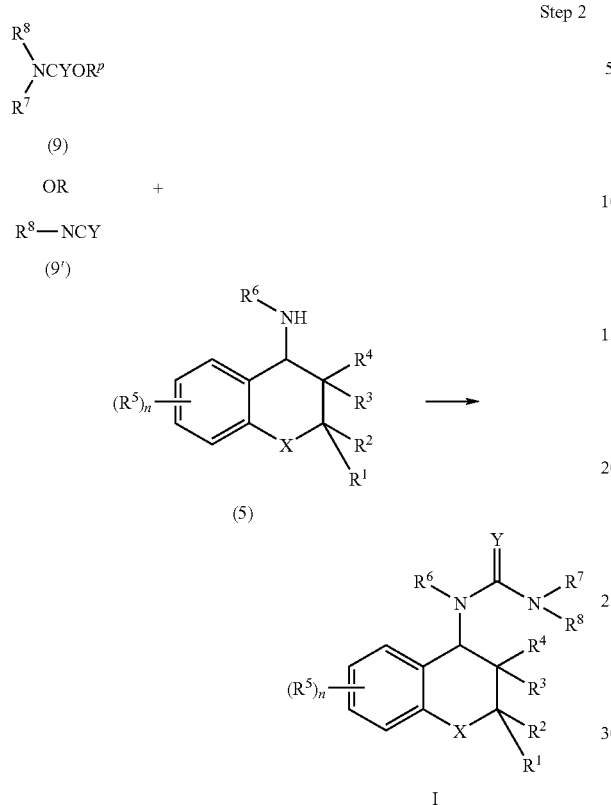

The compound of Formula I can be prepared by the above Scheme II. The compound of Formula (8) is reacted with compound of Formula (6), where X' is a leaving group and R$^p$ is as defined in Scheme I, (such as phenylchloroformate) to form compound of Formula (9). The compound of Formula (9) is reacted with a compound of Formula (5) to yield a compound of Formula I. Alternatively, a compound of Formula (9') can be reacted with a compound of Formula (5) to yield a compound of Formula I.

The compound of Formula (8) can be reacted with a compound of Formula (6) (wherein X' can be a leaving group, for example, halogen; R$^p$ can be, for example, hydrogen or alkyl) in one or more suitable organic bases including, but not limited to, pyrrolidine, morpholine, pyridine or mixtures thereof. The compound of Formula (8) can also be reacted in one or more solvents including, but not limited to, polar protic solvents (e.g., methanol, ethanol, isopropylalcohol and mixtures thereof), aprotic polar solvents (e.g., dichloromethane, acetonitrile, dichloroethane, tetrahydrofuran, dibromomethane, ether and mixtures thereof), and mixtures thereof. The compound of Formula (9) or Formula (9') can be reacted with compound of Formula (5) in one or more suitable solvent including, but not limited to, in one or more suitable solvent, such as, polar protic solvents (e.g., methanol, ethanol, isopropylalcohol and mixtures thereof), aprotic polar solvents (e.g., dichloromethane, dichloroethane, tetrahydrofuran, dibromomethane, dimethysulfoxide and mixtures thereof), and mixtures thereof in the presence of one or more suitable organic bases, including, but not limited to, triethylamine, pyridine, pyrrolidine, morpholine or mixtures thereof.

Scheme III

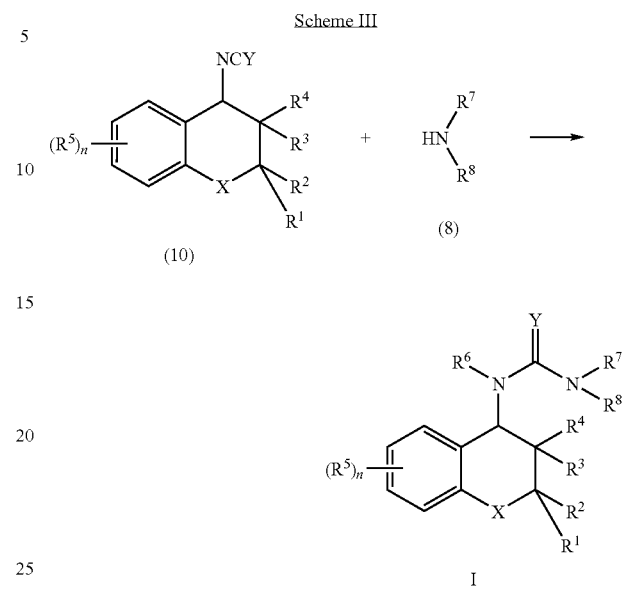

The compound of Formula I can be prepared by the above Scheme III. In this scheme, the compound of Formula (10) is reacted with an amine of Formula (8) to form the compound of Formula I.

This reaction can be performed in one or more suitable solvents, not limited to, in one or more suitable solvents including, but not limited to, polar protic solvents (e.g., methanol, ethanol, isopropylalcohol and mixtures thereof), aprotic polar solvents (e.g., dichloromethane, dichloroethane, tetrahydrofuran, dibromomethane and mixtures thereof), and mixtures thereof.

Scheme IV

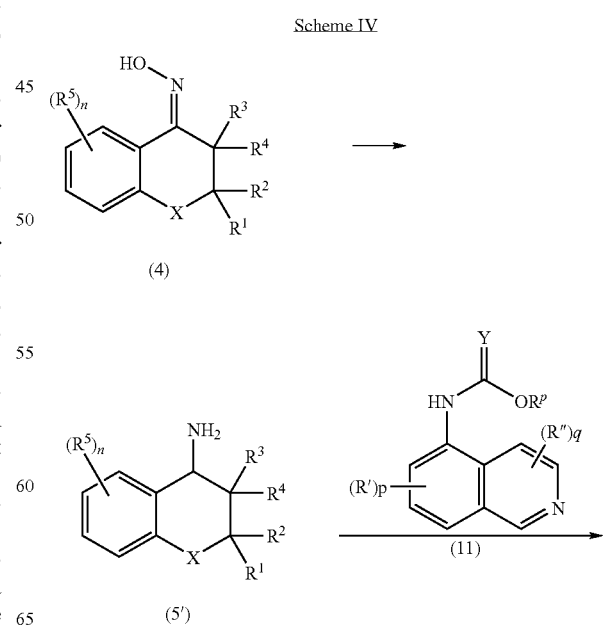

-continued

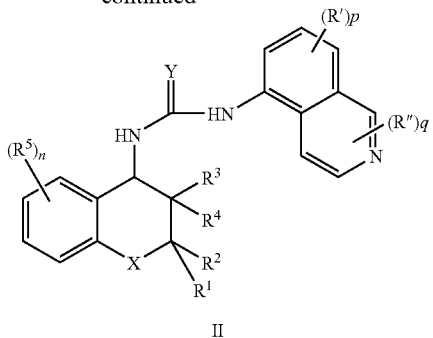

II

The compound of Formula II, where R', R", p, and q are as defined for Formula IIb above, can be prepared by the above Scheme IV. The compound of Formula (4) is reduced to form a compound of Formula (5'). The compound of formula (4) can be prepared by the procedure described in Scheme I. The compound of Formula (5') is then reacted with a compound of Formula (11), where $R^p$ is as defined in Scheme I, to form a compound of Formula II.

The compound of Formula (4) can be reduced to form an amine of Formula (5') in the presence of one or more reducing agents including, but not limited to, catalytic reducing agents (e.g., Nickel-Aluminum/hydrogen, palladium-carbon/hydrogen, platinum-carbon/hydrogen, Raney-Nickel/hydrogen or mixtures thereof) and boron reagents (e.g. sodium borohydride, sodium cyanoborohydride, $BH_3$. THF, $BH_3$-dimethylsulfide and mixtures thereof).

The compound of Formula (5') can be reacted with the compound of Formula (11) [wherein $R^p$ can be alkyl or aryl] in one or more suitable solvents including, but not limited to, polar protic solvents (e.g., methanol, ethanol, isopropylalcohol and mixtures thereof), aprotic polar solvents (e.g., dichloromethane, dichloroethane, tetrahydrofuran, dibromomethane, dimethylsulfoxide, dimethylformamide and mixtures thereof), and mixtures thereof to form a compound of Formula II.

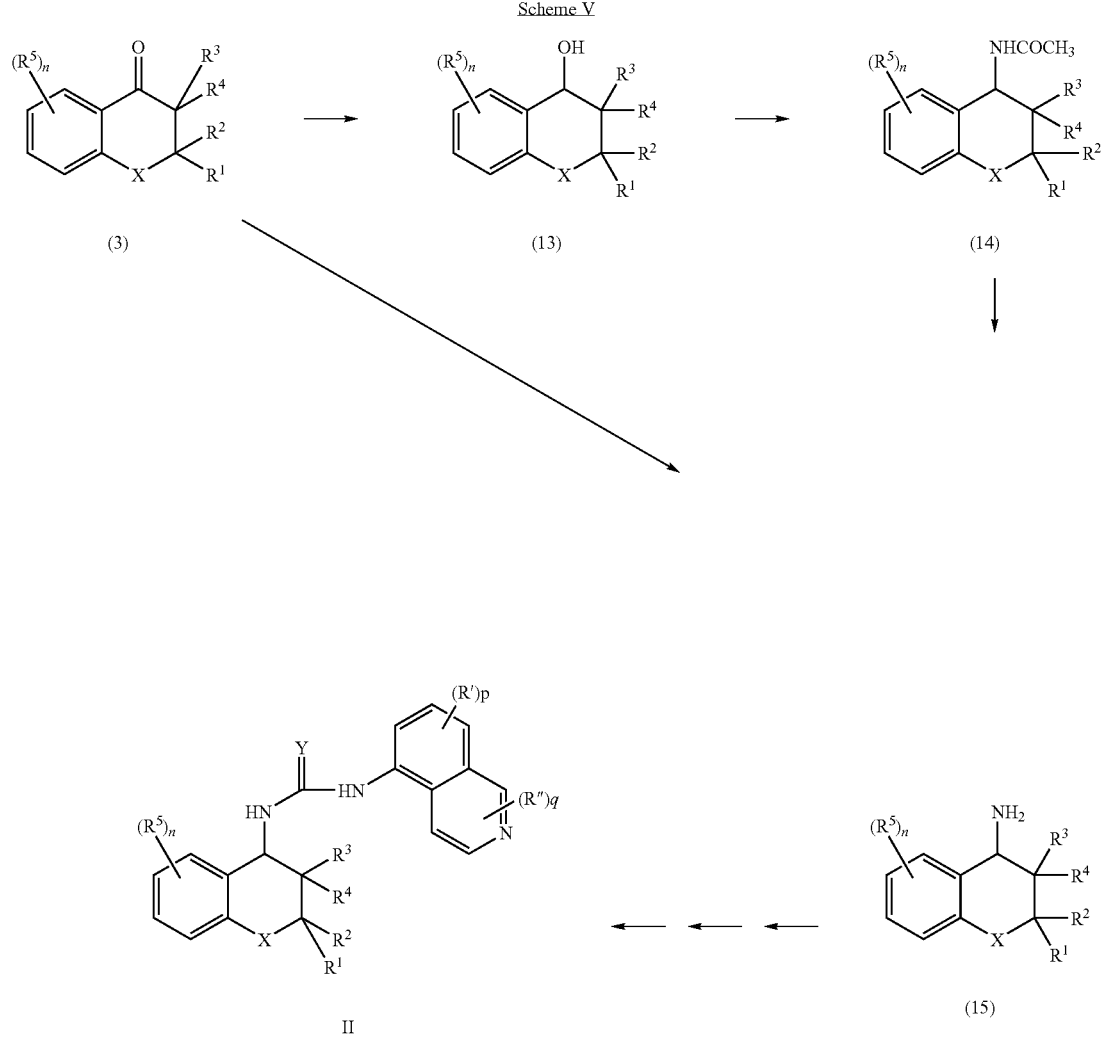

Scheme V

The compound of Formula II, where R', R", p, and q are as defined for Formula IIb above, can be prepared by the above Scheme V. The oxo group in the compound of Formula (3) is reduced to form a compound of Formula (13), which is converted to a compound of Formula (14) (for example, with acetamide). The compound of formula (14) is hydrolyzed to form a compound of Formula (15). The compound of Formula (15) is then reacted with a compound of Formula (11) (shown in Scheme IV) to form a compound of Formula II.

The compound of Formula (3) can be reduced to form a compound of Formula (13) in the presence of one or more reducing agents including, but not limited to, catalytic reducing agents (e.g. Nickel-Aluminum/hydrogen, palladium-carbon/hydrogen, platinum-carbon/hydrogen, Raney-Nickel/hydrogen or mixtures thereof) and boron reagents (e.g. sodium borohydride, sodium cyanoborohydride, $BH_3$-tetrahydrofuran, $BH_3$-dimethylsulfide and mixtures thereof). The reduction can be performed, for example, in one or more aprotic polar solvents, e.g., dichloromethane, dichloroethane, tetrahydrofuran, dibromomethane or mixtures thereof. The compound of Formula (13) can be reacted with acetamide to form a compound of Formula (14), for example, in the presence of acetonitrile and sulfuric acid. The compound of Formula (14) can be hydrolysed in the presence of a base (including, but not limited to, potassium bicarbonate, potassium carbonate, sodium carbonate, sodium bicarbonate, triethylamine, ammonium hydroxide, pyridine, alkylamines and mixtures thereof) or an acid (including, but not limited to, hydrochloric acid, trifluoroacetic acid and mixtures thereof).

Alternatively, the compound of Formula (3) can be directly converted to the compound of Formula (15), for example, by subjecting the compound of Formula (3) to reductive amination. The reductive amination may be performed in the presence of one or more reducing agents including, but not limited to, sodium borohydride, sodium cyanoborohydride, sodium triacetoxyborohydride, boranes and mixtures thereof. The reductive amination may be performed in the presence of ammonia, ammonium acetate, ammonium chloride, liquor ammonia or any mixture thereof.

The compound of Formula (15) can be reacted with the compound of Formula (11) [wherein $R^p$ can be alkyl or aryl] in one or more suitable solvents including, but not limited to, polar protic solvents (e.g., methanol, ethanol, isopropylalcohol and mixtures thereof), aprotic polar solvents (e.g., dichloromethane, dichloroethane, tetrahydrofuran, dibromomethane, dimethylsulfoxide, dimethylformamide and mixtures thereof), and mixtures thereof to form a compound of Formula II.

Scheme VI

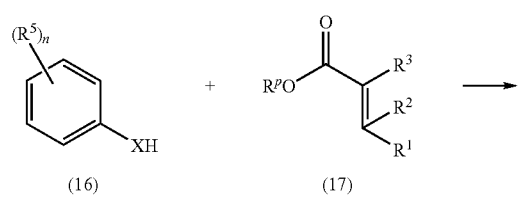

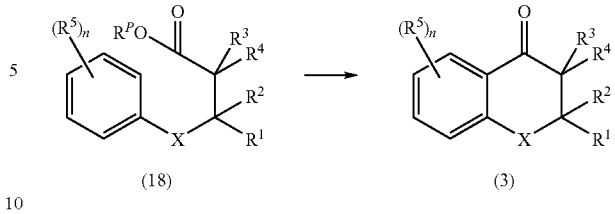

The compound of Formula (3) can be prepared by the above Scheme VI. This scheme for preparing the compound of Formula (3) can be used in combination with Scheme V, or in lieu of the method of preparing the compound of Formula (3) provided in Scheme I.

The compound of Formula (16) is reacted with a compound of Formula (17) (which can be an acrylic acid or ester), where $R^p$ is as defined in Scheme I above, to form compound of Formula (18). The compound of Formula (18) is cyclized to form a compound of Formula (19).

The compound of Formula (16) can be reacted with the compound of Formula (17) in the presence of a base including, but not limited to, potassium bicarbonate, potassium carbonate, sodium carbonate, sodium bicarbonate, triethylamine, ammonium hydroxide, pyridine, alkylamines and mixtures thereof. The reaction can be performed in one or more suitable solvents including, but not limited to, polar protic solvents (e.g., methanol, ethanol, isopropylalcohol and mixtures thereof), aprotic polar solvents (e.g., dichloromethane, dichloroethane, tetrahydrofuran, dibromomethane dimethylsulfoxide, dimethylformamide and mixtures thereof), and mixtures thereof.

Acid addition salts of the compounds described herein can be prepared following procedures known in the art.

EXAMPLES

Intermediate 1

Cyclobutylidene Acetic Acid

Step 1: Methyl cyclobutylidene acetate

To a solution of methoxycarbonyltriphenylphosphonium ylide (18 mmol, 6.1 gm) in benzene (45 ml) was added cyclobutanone (36 mmol) and refluxed for 2 days. Reaction was cooled and on addition of pentane (20-40 ml) the product precipitated as white solid after refrigeration.

Step 2: Cyclobutylidene acetic acid

Methyl cyclobutylidene acetate was hydrolyzed in methanol: 2N NaOH (1:1). After neutralization with 6N HCl and extraction with ethyl acetate the desired acid was obtained as a white solid.

Intermediate 2

Phenyl 1-methyl-1H-indazol-4ylcarbamate

Step 1: 4-nitro-1H-indazol

A solution of 2-methyl-3-nitro aniline (1 mmol) in acetic acid was stirred at room temperature and sodium nitrite (1.1 mmol) was added to the reaction mixture. Reaction mixture was stirred at room temperature for 5 hours. Reaction mixture was poured into water and neutralized with ammonia. Product precipitated out, was filtered and washed with water. It was then purified by column chromatography to afford the desired compound as a pale yellow solid.

$^1$H NMR (DMSO-d$_6$): δ 7.57-7.68 (1H, t, J=8.1 Hz); 8.06-8.12 (1H, d, J=8.4 Hz); 8.13-8.22 (1H, d, J=7.8 Hz); 8.51-8.57 (1H, s); 13.80-14.04 (1H, s)

Step 2: 1-methyl-4-nitro-1H-indazol and 2-methyl-4-nitro-1H-indazol

A solution of 4-nitro-1H-indazole (1 mmol) in DMF was cooled to 0° C. and potassium carbonate (1.2 mmol) was added to the reaction mixture. Methyl iodide was added dropwise to the reaction mixture at 0° C. Reaction mixture was stirred at 0° C. for 1 hour and then stirred at room temperature for 15 hours. Reaction mixture was filtered, diluted with water and extracted with ethyl acetate. Ethyl acetate layer was washed with saturated brine solution and water. Ethyl layer was dried over anhydrous sodium sulfate and evaporated under vacuum. Crude product was column purified to get both the isomers.

$^1$H NMR (DMSO-d$_6$) for 1-methyl isomer: δ 4.16-4.23 (3H, s); 7.61-7.72 (1H, t, J=8.1 Hz); 8.14-8.21 (1H, d, J=7.2 Hz); 8.22-8.31 (1H, d, J=8.4 Hz); 8.46-8.55 (1H, s)

$^1$H NMR (DMSO-d$_6$) for 2-methyl isomer: δ 4.29 (3H, s); 7.47-7.52 (1H, t, J=8.1 Hz); 8.17-8.18 (1H, d, J=7.2 Hz); 8.20-8.11 (1H, d, J=8.4 Hz); 8.87 (1H, s).

Step 3: 1-methyl-1H-indazol-4-amine

A solution of 1-methyl nitro-1H-indazole in ethanol was hydrogenated in the presence of 10% Pd/C at 60 psi for 20 hours. Reaction mixture was filtered through celite. Filtrate was concentrated under vacuum and the residue was column purified.

$^1$H NMR (DMSO-d$_6$): δ 3.90 (3H, s); 5.76 (2H, s); 6.13 (1H, d, J=7.5 Hz); 6.63 (1H, d, J=8.4 Hz); 7.02 (1H, t, J=7.6 Hz); 8.03 (1H, s).

Step 4: Phenyl 1-methyl-1H-indazol-4-ylcarbamate

A solution of phenyl chloroformate (1.1 mmol) in chloroform was cooled to 0° C. 1-methyl-1H-indazole-4-amine in dry THF was added to the reaction mixture dropwise at 0° C. Pyridine (1 mmol) was added to the reaction mixture. Reaction mixture was stirred at 0° C. for 30 minutes and was then stirred at room temperature for 15 hours.

Reaction mixture was concentrated under vacuum to remove the excess solvent Residue was column purified to obtain the pure carbamate.

$^1$H NMR (DMSO-d$_6$): δ 4.02 (3H, s); 6.75 (1H, d), 7.14 (1H, t), 7.25-7.55 (6H, m); 8.39 (1H, s); 10.48 (1H, s).

Intermediate 3

(±) 4-Amino-3,4-Dihydrospiro-2H-1-benzopyran-2,1'cyclobutane.HCl

Step I: 3,4-Dihydrospiro-[2H]-1-benzopyran-2,1'-cyclobutane-4-one

A solution of 2'-hydroxy acetophenone (10 mmol), Cyclobutanone (10 mmol) and pyrrolidine (20 mmol) was refluxed for 15 h in methanol. The reaction mixture was then cooled to room temperature and concentrated in vacuum. The residue was dissolved in ethyl acetate and washed with sat. NaHCO$_3$ followed by 6N HCl. The HCl layer was separated and basified to pH 9. The product was extracted in ethyl acetate. The organic layer was then separated, dried over anhydrous Na$_2$SO$_4$, and concentrated in vacuum to afford the desired product in quantitative yield.

Step II: 3,4-Dihydro-4-(hydroxyimino)-spiro-[2H]-1-benzopyran-2,1'-cyclobutane: A solution of 3,4-Dihydrospiro-[2H]-1-benzopyran-2,1'-cyclobutane-4-one: (10 mmol) and hydroxylamine. HCl (15 mmol) in ethanol (20 ml) was refluxed for 5 h in the presence of sodium hydroxide (50 mmol in 5 ml water). The reaction mixture was then cooled to room temperature and treated with sat. NH$_4$Cl. 3,4-Dihydro-4-(hydroxyimino)-spiro-[2H]-1-benzopyran-2,1'-cyclobutane was separated in the form of a precipitate. It was then filtered and washed with water.

Step III: (±) 4-Amino-3,4-Dihydrospiro-2H-1-benzopyran-2,1'-cyclobutane trifluoroacetic acid To a solution of 3,4-Dihydro-4-(hydroxyimino)-spiro-[2H]-1-benzopyran-2,1'-cyclobutane (0.5 g) in ethanol (10 ml) and aq. NaOH (2N, 10 ml), Ni—Al alloy (0.75 g) was added. The suspension was then stirred at room temperature for 15 h. The reaction mixture was then filtered through a bed of celite and washed with ethanol. Ethanol was evaporated and the residue was dissolved in THF and treated with BOC anhydride (1.5 eq.). The desired compound was then extracted in ethyl acetate. The organic layer was separated, dried over anhydrous Na$_2$SO$_4$, and concentrated in vacuum to afford a residue. The residue was dissolved in dichloromethane and treated with trifluoroacetic acid at room temperature for 24 h. The solvent and trifluoroacetic acid were evaporated under vacuum to afford the desired (±) 4-Amino-3,4-Dihydrospiro-2H-1-benzopyran-2,1'cyclobutane TFA in quantitative yield. $^1$H NMR (DMSO-d$_6$): δ 1.67-1.2.36 (8H, m); 4.57 (1H, m); 6.85 (1H, d, J=8.1 Hz); 6.98 (1H, t, J=8.1 Hz); 7.26 (1H, d, J=8.4 Hz); 7.59 (1H, d, J=7.5 Hz); 8.73 (3H, b).

Intermediate 4

8-chloroisoquinolin-5-amine

Step 1: 8-Chloroisoquinoline

To a solution of 8-aminoisoquinoline (*J. Med. Chem.*, 2005, 48, 744-52) (1 mmol) in concentrated hydrochloric acid was added a solution of sodium nitrite (1.2 mmol) in water. The diazotization was carried out at 0° C. The cold diazonium salt solution was added to a solution of cuprous chloride in concentrated hydrochloric acid at 0° C. The cold solution was warmed to room temperature and stirred at room temperature for 3 hours. After 3 hours, the solution was heated at 60° C. for 30 min. Reaction mixture was basified and extracted with diethyl ether. Ether was washed with cold concentrated sulfuric acid, brine. Ether was dried over anhydrous sodium sulfate and evaporated under vacuum. Crude residue was column purified to afford a pale yellow liquid.

$^1$H NMR (DMSO-d$_6$): δ ☐7.73-7.85 (2H, m); 7.93-7.95 (1H, d, J=5.7 Hz); 7.98-8.01 (1H, d, J=7.8 Hz); 8.64-8.66 (1H, d, J=5.4 Hz); 9.55 (1H, s)

Step 2: 8-chloro-5-nitroisoquinoline

To a solution of 8-chloroisoquinoline (1 mmol) in concentrated sulfuric acid at 0° C. was added potassium nitrate (1.1 mmol). The reaction mixture was warmed to room temperature and stirred at room temperature for 5 hours. The reaction mixture was basified Solid precipitated was column purified to afford a pale yellow solid.

$^1$H NMR (DMSO-d$_6$): δ □7.76-7.79 (1H, d, J=8.4 Hz); 8.48-8.51 (1H, d, J=8.4 Hz); 8.53-8.55 (1H, d, J=6 Hz); 8.86-8.88 (1H, d, J=6.3 Hz); 9.84 (1H, s)

Step 3: 8-chloroisoquinolin-5-amine

To a solution of 8-chloro-5-nitroisoquinoline (1 mmol) in acetic acid, zinc dust (10 mmol) was added. Reaction mixture was refluxed for 5 hours. Reaction mixture was cooled to room temperature and filtered through celite bed. Filtrate was concentrated under vacuum to afford the desired compound.

$^1$H NMR (DMSO-d$_6$): δ 6.22 (2H, bs); 6.81-6.84 (1H, d, J=8.1 Hz); 7.45-7.48 (1H, d, J=8.1 Hz); 8.01-8.03 (1H, d, J=5.7 Hz); 8.49-8.51 (1H, d, J=6 Hz); 9.36 (1H, s)

Intermediate 5 1-methylisoquinolin-5-amine

Step 1: 1-methyl-5-nitroisoquinoline

To a solution of 1-methyl isoquinoline (Aldrich) in concentrated sulfuric acid at 0° C. was added potassium nitrate (1.1 mmol). Reaction mixture was warmed to room temperature and stirred at room temperature for 5 hours. Reaction mixture was basified. Solid precipitated was column purified.

$^1$H NMR (DMSO-d$_6$): δ 2.98 (3H, s); 7.84-7.89 (1H, t, J=7.9 Hz); 8.08-8.10 (1H, d, J=5.4 Hz); 8.57-8.60 (2H, m); 8.66-8.69 (1H, d, J=8.4 Hz)

Step 2: 1-methylisoquinolin-5-amine

A solution of 1-methyl-5-nitroisoquinoline in ethanol was hydrogenated in the presence of 10% palladium carbon at 60 psi for 4 hours. Reaction mixture was filtered through celite bed. Filtrate was concentrated under vacuum to afford the desired compound as pale white solid.

$^1$H NMR (DMSO-d$_6$): δ2.78 (3H, S); 5.91 (2H, bs); 6.85 (1H, m); 7.30 (2H, m); 7.79 (1H, d); 8.18-8.19 (1H, d, J=3.9 Hz)

Intermediate 6

Thieno[2,3-c]pyridin-3-amine

Thieno[2,3-c]pyridin-3-amine was prepared as described in WO 2006/063178

Example 1

(±) 1-{3,4-Dihydro-1'-(methyl)spiro-[2H-1-benzopyran-2,4'-piperidine]-4-yl}-3-(isoquinoline-5-yl)urea

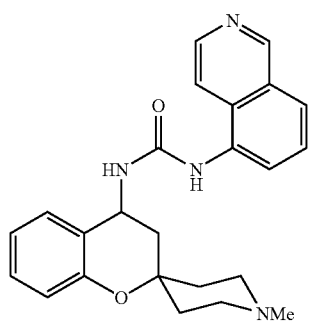

Step I: 3,4-Dihydro-spiro-1'-methyl-2H-1-benzopyran-2, 4'-piperidine-4-one: A solution of 2'-hydroxy acetophenone (10 mmol), N-methylpiperidone (10 mmol) and pyrrolidine (20 mmol) in methanol was refluxed for 15 h. The reaction mixture was then cooled to room temperature and concentrated in vacuum. The residue was dissolved in ethyl acetate and washed with sat. NaHCO$_3$ followed by 6N HCl. The HCl layer was separated and basified to pH 9. Product was extracted in ethyl acetate. Organic layer was separated, dried over anhydrous Na$_2$SO$_4$ and concentrated in vacuum to afford the desired product in quantitative yield.

$^1$H NMR (CDCl$_3$): δ 1.76 (2H, m, CH$_2$); 2.04 (2H, m, CH$_2$); 2.33 (3H, s, CH$_3$); 2.43 (2H, t, J=11.1); 2.60 (2H, m, CH$_2$); 2.72 (2H, s, CH$_2$); 7.22 (2H, m, 2×ArH); 7.50 (1H, m, ArH); 7.86 (1H, dd, J=2.1 & 8.4 Hz).

Step II: 3,4-Dihydro-4-(hydroxyimino)-1'-methyl-spiro-[2H]-1-benzopyran-2,4'-piperidine: A solution of 3,4-Dihydro-spiro-1'-methyl-2H-1-benzopyran-2,4'-piperidine-4-one (10 mmol) and Hydroxylamine.HCl (15 mmol) in ethanol (20 ml) was refluxed for 5 h in the presence of Sodium hydroxide (50 mmol in 5 ml water). The reaction mixture was cooled to room temperature and treated with sat. NH$_4$Cl. 3,4-Dihydro-4-(hydroxyimino)-1'-methyl-spiro-[2H]-1-benzopyran-2,4'-piperidine separated in the form of a precipitate. It was then filtered and washed with water.

$^1$H NMR (DMSO-d$_6$): δ 1.57-1.77 (4H, m, 2×CH$_2$); 2.19 (3H, s, CH$_3$); 2.28 (2H, t, J=9.9); 2.46 (2H, m, CH$_2$); 2.76 (2H, s, CH$_2$); 6.91 (2H, m, 2×ArH); 7.26 (1H, m, ArH); 7.74 (1H, d, J=7.8 Hz); 11.29 (1H, s, OH).

Step III: (±) 4-Amino-3,4-Dihydro-spiro-1'-methyl-2H-1-benzopyran-2,4'-piperidine.ditrifluoroacteate (2TFA): To a solution of 3,4-Dihydro-4-(hydroxyimino)-1'-methyl-spiro-[2H]-1-benzopyran-2,4'-piperidine (0.5 g) in ethanol (10 ml) and aq. NaOH (2N, 10 ml), was added Ni—Al alloy (0.75 g). The suspension was then stirred at room temperature for 15 h. Reaction mixture was then filtered through a bed of celite and washed with ethanol. Ethanol was evaporated and the residue was taken in THF and treated with Boc anhydride (1.5 eq.). The desired compound was then extracted in ethyl acetate. Organic layer was separated, dried over anhydrous Na$_2$SO$_4$ and concentrated in vacuum to afford a residue. The residue was dissolved in dichloromethane and treated with trifluoroacetic acid at room temperature for 24 h. The solvent and trifluoroacetic acid was evaporated under vacuum to afford the desired 4-Amino-3,4-Dihydro-spiro-1'-methyl-2H-1-benzopyran-2,4'-piperidine.2TFA in quantitative yield.

$^1$H NMR (MeOH-d$_4$): δ 1.81-2.15 (5H, m, 2×CH$_2$ & CH); 2.30 (1H, dd, J=13.2 & 6.6 Hz, CH); 2.84 (3H, s, CH$_3$); 3.07 (1H, m, CH); 3.25 (1H, m, CH); 3.41 (2H, m, CH$_2$); 4.61 (1H, dd, J=6.9 & 11.1 Hz, CH); 6.96 (2H, m, 2×ArH); 7.24 (1H, t, J=7.5 Hz, ArH); 7.37 (1H, d, J=8.1 Hz).

Step IV: (±) 1-(3,4-Dihydro-1'-(methyl)spiro-[2H-1-benzopyran-2,4'-piperidine]-4-yl)-3-(isoquinoline-5-yl)urea: A solution of phenyl N-(5-isoquinolinyl)carbamate (1 mmol) and 4-Amino-3,4-Dihydro-spiro-1'-methyl-2H-1-benzopyran-2,4'-piperidine-2TFA (1 mmol) in DMSO was stirred in the presence of a base such as triethylamine (2 mmol). Few drops of water were added in the reaction mixture. The desired urea precipitated, filtered and washed with water.

$^1$H NMR (MeOH-d$_4$): δ 1.62-1.87 (5H, m, 2×CH$_2$ & CH); 2.12-2.34 (5H, m, 2×CH & CH$_3$); 2.56 (3H, m, CH & CH$_2$); 5.08 (1H, dd, J=6.6 & 10.8 Hz); 6.73 (1H, d, J=8.4 Hz, ArH); 6.84 (1H, t, J-7.8 Hz, ArH); 7.08 (1H, t, J=7.5 Hz, ArH); 7.29 (1H, d, J=7.8 Hz, ArH); 7.59 (1H, t, J=7.8 Hz, ArH); 7.78 (1H, d, J=7.5 Hz, ArH); 7.84 (1H, d, J=6.3 Hz,

ArH); 8.09 (1H, d, J=7.5 Hz, ArH); 8.36 (1H, d, J=6.0 Hz, ArH); 9.13 (1H, s, ArH). Melting point: 130° C.; IR (KBr): 3341, 1698, 1551, 1234, 757.

The compounds in Examples 2 were prepared according to the method described in Example 3 using substrates appropriately substituted at $R^1$-$R^2$.

Example 2

(±) 1-(2',3,3',4,5',6'-Hexahydrospiro-[2H]-1-benzopyran-2,4'-pyran-4-yl)-3-(isoquinoline-5-yl)urea

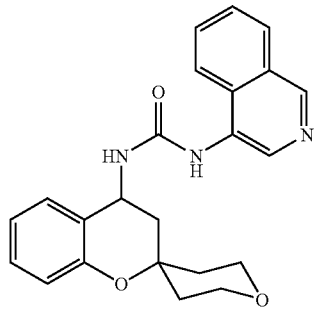

Step I: 2',3,3',4,5',6'-Hexahydrospiro-[2H]-1-benzopyran-2,4'-[4H]pyran-4-one

Step II: 2',3,3',4,5',6'-Hexahydro-4-(hydroxyimino)-spiro-[2H]-1-benzopyran-2,4'-[4H]pyran Step III: (±) 4-Amino-2',3,3',4,5',6'-hexahydrospiro-[2H]-1-benzopyran-2,4'-[4H]-pyran. $^1$H NMR (CDCl$_3$): δ 1.68-1.90 (7H, m); 2.17 (1H, dd, J=6.3 & 13.2 Hz); 3.76-3.88 (3H, m); 3.98-4.14 (2H, m); 6.91 (1H, d, J=8.1 Hz); 6.99 (1H, t, J=6.0 Hz); 7.21 (1H, t, J=6.9 Hz); 7.48 (1H, d, 7.8 Hz).

Step IV: (±) 1-(2',3,3',4,5',6'-Hexahydrospiro-[2H-1-benzopyran-2,4'-pyran]-4-yl)-3-(isoquinoline-5-yl)urea $^1$H NMR (CDCl$_3$): δ 1.72-1.85 (5H, m); 2.28 (1H, dd, J=–6.6 & 13.5 Hz); 3.61-3.79 (4H, m); 5.05 (1H, m); 6.87 (1H, d, J=8.1 Hz); 6.94 (1H, t, J=–7.2 Hz); 7.01 (1H, d, J=8.4 Hz); 7.19 (1H, t, J=7.5 Hz); 7.35 (1H, d, J=7.8 Hz); 7.63 (1H, t, J=7.5 Hz); 7.77 (1H, d, J=8.1 Hz); 7.93 (1H, d, J=6.3 Hz); 8.36 (1H, d, J=–7.5 Hz); 8.55 (1H, d, J=5.7 Hz); 8.73 (1H, s); 9.29 (1H, s); Melting point: 220° C.; IR (KBr): 3323, 1635, 1560, 1483, 1236, 753.

Example 3

(±) 1-(3,4-Dihydro-spiro-[2H-1-benzopyran-2,1'-cyclobutan]-4-yl)-3-(isoquinolin-5-ylurea

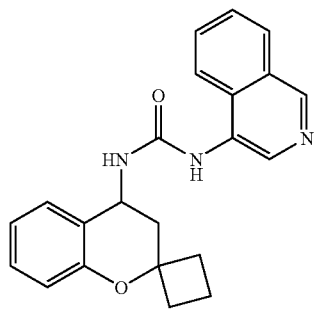

Step I: 3,4-Dihydro-spiro[2H-1-benzopyran-2,1'-cyclobutane-4-one]: A solution of 2'-hydroxy acetophenone (10 mmol), cyclobutanone (10-20 mmol) and pyrrolidine (20 mmol) in methanol was stirred at room temperature for 15 h. The solvent was removed under vacuum. The residue was dissolved in ethyl acetate and washed with 6N HCl. Organic layer was separated, dried over anhydrous Na$_2$SO$_4$ and concentrated in vacuum to afford the crude product which, on purification by column chromatography afforded the desired product as yellow oil.

$^1$H NMR (CDCl$_3$): δ 1.66-1.79 (1H, m); 1.86-1.99 (1H, m); 2.13-2.21 (2H, m); 2.28-2.39 (2H, m); 2.90 (2H, s); 6.96-7.02 (2H, m); 7.48 (1H, t, J=–7.5 Hz); 7.85 (1H, d, J=7.8 Hz).

Step II: 3,4-Dihydro-4-(hydroxyimino)-spiro[2H-1-benzopyran-2,1'-cyclobutane]: was synthesized using the process described in Step-II of Example 1

$^1$H NMR (CDCl$_3$): δ 1.70-1.79 (1H, m); 1.82-1.97 (1H, m); 2.07-2.15 (2H, m); 2.22-2.37 (2H, m); 3.07 (2H, s); 6.89-6.95 (2H, m); 7.25-7.30 (2H, m); 7.77 (1H, d, J=8.1 Hz).

Step III: (±) 4-Amino-3,4-dihydro-spiro[2H-1-benzopyran-2,1'cyclobutane]hydrochloride: was synthesizes using the process as described in Step-III of Example 1

$^1$H NMR DMSO-d$_6$): δ 1.67-2.36 (8H, m); 4.57 (1H, m); 6.85 (1H, d, J=8.1 Hz); 6.98 (1H, t, J=8.1 Hz); 7.26 (1H, d, J=8.4 Hz); 7.59 (1H, d, J=7.5 Hz); 8.73 (3H, b).

This amine was resolved using R and S-mandelic acid in acetonitrile to give (–) 4-Amino-3,4-dihydro-spiro-2H-1-benzopyran-2,1'cyclobutane and (+) 4-Amino-3,4-dihydro-spiro-2H-1-benzopyran-2,1'cyclobutane respectively.

$^1$H NMR (DMSO-d$_6$) for (–) amine: δ 1.56-1.82 (3H, m); 1.93-2.14 (3H, m); 2.24-2.36 (2H, m); 3.83-3.89 (1H, m); 6.70 (1H, d, J=8.1 Hz); 6.84 (1H, t, J=8.1 Hz); 7.06 (1H, t, J=8.4 Hz); 7.50 (1H, d, J=7.5 Hz). This compound has R-configuration [Ref. Tetrahedron 55 (1999) 7555-7562]

$^1$H NMR (DMSO-d$_6$) for (+) amine: δ 1.58-1.82 (3H, m); 1.97-2.16 (3H, m); 2.24-2.36 (2H, m); 3.89-3.94 (1H, m); 6.70 (1H, d, J=8.1 Hz); 6.85 (1H, t, J=8.1 Hz); 7.07 (1H, t, J=8.4 Hz); 7.50 (1H, d, J=7.5 Hz). This compound has S-configuration [Ref. Tetrahedron 55 (1999) 7555-7562]

Step IV: (±) 1-(3,4-Dihydro-spiro[2H-1-benzopyran-2,1'-cyclobutan]-4-yl)-3-(isoquinolin-5-yl)urea: was synthesizes using the process as described in Step-IV of Example 1.

$^1$H NMR (DMSO-d$_6$): δ 1.73-1.97 (3H, m); 2.15-2.32 (4H, m); 2.42 (1H, m); 5.02 (1H, m); 6.82 (1H, d, J=7.8 Hz); 6.93 (1H, t, J=6.9 Hz); 7.04 (1H, d, J=8.1 Hz); 7.18 (1H, t, J=7.2 Hz); 7.31 (1H, d, J=7.2 Hz); 7.62 (1H, t, J=7.5 Hz); 7.77 (1H, d, J=8.1 Hz); 7.94 (1H, d, J=6.0 Hz); 8.39 (1H, d, J=7.5 Hz); 8.56 (1H, d, J=6.0 Hz); 8.74 (1H, s); 9.29 (1H, s); Melting Point: 246° C.; IR (KBr): 3326, 3277, 1627, 1563, 1239, 753.

(±) 4-Amino-3,4-dihydro-spiro[2H-1-benzopyran-2,1'cyclobutane]hydrochloride were resolved as described in Step III of Example 3, and were reacted with the appropriate carbamate to form the compounds described in Example 4 and Example 5

Example 4

(+) 1-(3,4-Dihydro-spiro-[2H-1-benzopyran-2,1'-cyclobutan]-4-yl)-3-(isoquinolin-5-yl)urea $^1$H NMR (DMSO-d$_6$) for hydrochloride salt: δ 1.72-1.98 (3H, m); 2.08-2.50 (5H, m); 5.03 (1H, m); 6.80 (1H, d, J=8.1 Hz); 6.91 (1H, t, J=7.2 Hz); 7.14 (1H, t, J=7.5 Hz); 7.29 (1H, d, J=7.5 Hz); 7.59 (1H, bm); 7.93 (1H, d, J=8.1 Hz); 8.10 (1H, d, J=7.8 Hz); 8.72 (3H, bm), 9.60 (1H, s); 9.80 (1H, s)

$^1$H NMR (DMSO-d$_6$) for sulfate salt: δ 1.72-2.00 (3H, m); 2.08-2.50 (5H, m); 5.02 (1H, m); 6.81 (1H, d, J=8.1 Hz); 6.93

(1H, t, J=7.2 Hz); 7.10-7.18 (2H, m); 7.30 (1H, d, J=6.8 Hz); 7.96 (1H, t, J=8.1 Hz); 8.15 (1H, d, J=7.8 Hz); 8.44 (1H, d, J=6.3 Hz); 8.66 (1H, d, J=7.8 Hz); 8.73 (1H, d, J=6.3 Hz); 9.10 (1H, s); 9.83 (1H, s)
IR (KBr): 3275, 3072, 2926, 1643, 1556, 1315, 1276, 1179, 1037, 866, 805, 755.
$[\alpha]^{25}$=+54 to +57°(c=1, methanol)

Example 5

(−) 1-(3,4-Dihydro-spiro-[2H-1-benzopyran-2,1'-cyclobutan]-4-yl)-3-(isoquinolin-5-yl)urea $^1$H NMR (DMSO-d$_6$) for hydrochloride salt: δ 1.72-1.98 (3H, m); 2.08-2.50 (5H, m); 5.03 (1H, m); 6.80 (1H, d, J=8.1 Hz); 6.91 (1H, t, J=7.2 Hz); 7.14 (1H, t, J=7.5 Hz); 7.29 (1H, d, J=7.5 Hz); 7.59 (1H, bm); 7.93 (1H, t, J=8.1 Hz); 8.10 (1H, d, J=7.8 Hz); 8.72 (3H, bm), 9.60 (1H, s); 9.80 (1H, s)
$^1$H NMR (DMSO-d$_6$) for sulfate salt: δ 1.72-2.00 (3H, m); 2.08-2.50 (5H, m); 5.02 (1H, m); 6.81 (1H, d, J=8.1 Hz); 6.93 (1H, t, J=7.2 Hz); 7.10-7.18 (2H, m); 7.30 (1H, d, J=6.8 Hz); 7.96 (1H, t, J=8.1 Hz); 8.15 (1H, d, J=7.8 Hz); 8.44 (1H, d, J=6.3 Hz); 8.66 (1H, d, J=7.8 Hz); 8.73 (1H, d, J=6.3 Hz); 9.10 (1H, s); 9.83 (1H, s)
IR (KBr): 3275, 3072, 2926, 1643, 1556, 1315, 1276, 1179, 1037, 866, 805, 755.
$[\alpha]^{25}$=+54 to +57° (c=1, methanol)

Examples 6 to 30 were prepared according to the method described in Example 3, using an appropriately substituted carbamate.

Example 6

(±) 1-(3,4-dihydro-spiro[2H-1-benzopyran-2,1'-cyclobutane]-4-yl)-3-(8-chloroisoquinolin-5-yl)urea $^1$H NMR (DMSO-d$_6$): δ 1.71-1.98 (3H, m); 2.10-2.45 (5H, m); 5.02 (1H, m); 6.82 (1H, d, J=8.4 Hz); 6.92 (1H, t, J=6.9 Hz); 7.07 (1H, d, J=8.1 Hz); 7.17 (1H, t, J=7.2 Hz); 7.31 (1H, d, J=7.5 Hz); 7.77 (1H, d, J=7.5 Hz); 8.02 (1H, d, J=6.0 Hz); 8.38 (1H, d, J=8.4 Hz); 8.72 (1H, d, J=6.0 Hz); 8.85 (1H, s); 9.53 (1H, s); IR (KBr) (cm$^{-1}$): 3308, 2987, 2942, 1633, 1570, 1483, 1373, 1311, 1269, 1243, 830, 752; MS (M$^+$+1): 394.1

Example 7

(±) 1-(3,4-Dihydro-spiro[2H-1-benzopyran-2,1'-cyclobutane]-4-yl)-3-(3-methylisoquinolin-5-yl)urea $^1$H NMR (DMSO-d$_6$): δ 1.69-1.96 (3H, m); 2.12-2.45 (5H, m); 2.64 (3H, s); 5.01 (1H, m); 6.81 (1H, d, J=8.1 Hz); 6.92 (1H, t, J=7.5 Hz); 7.03 (1H, d, J=8.1 Hz); 7.18 (1H, t, J=8.4 Hz); 7.30 (1H, d, J=7.8 Hz); 7.53 (1H, t, J=8.1 Hz); 7.70 (1H, d, J=8.1 Hz); 8.33 (1H, d, J=7.8 Hz); 8.64 (1H, s); 9.18 (1H, s); IR (KBr) (cm$^{-1}$): 3309, 1627, 1565, 1238; MS (M$^+$+1): 374.1

Example 8

(±) 1-(3,4-Dihydro-spiro[2H-1-benzopyran-2,1'-cyclobutane]-4-yl)-3-(1-methylisoquinolin-5-yl)urea $^1$H NMR (DMSO-d$_6$): δ 1.72-1.96 (3H, m); 2.15-2.43 (5H, m); 2.89 (3H, s); 5.02 (1H, m); 6.81 (1H, d, J=7.5 Hz); 6.92 (1H, t, J=7.2 Hz); 7.04 (1H, d, J=8.1 Hz); 7.18 (1H, t, J=5.7 Hz); 7.30 (1H, d, J=7.2 Hz); 7.61 (1H, t, J=7.5 Hz); 7.79 (1H, d, J=6.3 Hz); 7.86 (1H, d, J=8.1 Hz); 8.36 (1H, d, J=8.4 Hz); 8.39 (1H, d, J=5.7 Hz); 8.69 (1H, s); IR (KBr) (cm$^{-1}$): 3308, 1631, 1560, 1233; MS (M$^+$+1): 374.2

Example 9

(±) 1-(3,4-Dihydro-spiro[2H-1-benzopyran-2,1'-cyclobutane]-4-yl)-3-(2-oxoisoquinolin-5-yl)urea This compound was synthesized by oxidizing (±) 1-(3,4-Dihydro-spiro[2H-1-benzopyran-2,1'-cyclobutan]-4-yl)-3-(isoquinolin-5-yl)urea (example 3) using metachloroperbenzoic acid (3.0 eq) in chloroform or dichloromethane at room temperature.
$^1$H NMR (DMSO-d$_6$): δ 1.73-1.97 (3H, m); 2.15-2.42 (5H, m); 5.02 (1H, m); 6.78 (1H, d, J=7.8 Hz); 6.93 (1H, t, J=6.9 Hz); 7.18 (1H, t, J=7.2 Hz); 7.24 (1H, d, J=8.1 Hz); 7.39-7.63 (3H, m); 7.78 (1H, m); 8.00-8.21 (4H, m); 8.94 (1H, s).

Example 10

(+) 1-(3,4-Dihydro-spiro[2H-1-benzopyran-2,1'-cyclobutane]-4-yl)-3-(2-oxoisoquinolin-5-yl)urea This compound was synthesized by oxidizing (−) 1-(3,4-Dihydro-spiro[2H-1-benzopyran-2,1'-cyclobutan]-4-yl)-3-(isoquinolin-5-yl)urea (example 4) using metachloroperbenzoic acid (3.0 eq) in chloroform or dichloromethane at room temperature.
$^1$H NMR (DMSO-d$_6$): δ 1.73-1.97 (3H, m); 2.15-2.42 (5H, m); 5.02 (1H, m); 6.78 (1H, d, J=7.8 Hz); 6.93 (1H, t, J=6.9 Hz); 7.18 (1H, t, J=7.2 Hz); 7.24 (1H, d, J=8.1 Hz); 7.39-7.63 (3H, m); 7.78 (1H, m); 8.00-8.21 (4H, m); 8.94 (1H, s).

Example 11

(±) 1-(3,4-Dihydro-spiro[2H-1-benzopyran-2,1'-cyclobutane]-4-yl)-3-(6-chloro-1,3-benzothiazol-2-yl)urea $^1$H NMR (DMSO-d$_6$): δ 1.70-1.98 (3H, m); 2.13-2.39 (5H, m); 5.01 (1H, m); 6.80 (1H, d, J=7.5 Hz); 6.90 (1H, t, J=7.2 Hz); 7.19 (2H, dd, J=7.5. Hz); 7.39 (1H, d, J=8.4 Hz); 7.62 (1H Hd, J=8.4 Hz); 8.04 (1H, s); 10.73 (1H, s); IR (KBr) (cm$^{-1}$): 3310, 3272, 1634, 1563, 1233; MS (M$^+$+1): 399.20

Example 12

(±) 1-(3,4-Dihydro-spiro[2H-1-benzopyran-2,1'-cyclobutane]-4-yl)-3-(6-fluoro-1,3-benzothiazol-2-yl)urea $^1$H NMR (DMSO-d$_6$): δ 1.75-1.98 (3H, m); 2.06-2.34 (5H, m); 3.82-4.17 (3H, s); 4.99 (1H, m); 6.65-6.96 (3H, m); 7.10-7.34 (4H, m); 7.68-7.79 (1H, m); 7.97-8.07 (1H, s); 8.66-8.78 (1H, s); IR (KBr) (cm$^{-1}$): 3359, 3278, 1640, 1551, 1234; MS (M$^+$+1): 363.24

Example 13

(±) 1-(3,4-Dihydro-spiro[2H-1-benzopyran-2,1'-cyclobutane]-4-yl)-3-(1-methyl-1H-indazol-5-yl)urea $^1$H NMR (DMSO-d$_6$): δ 1.75-1.98 (3H, m); 2.06-2.34 (5H, m); 3.82-4.17 (3H, s); 4.99 (1H, m); 6.65-6.96 (3H, m); 7.10-7.34 (4H, m); 7.68-7.79 (1H, m); 7.97-8.07 (1H, s); 8.66-8.78 (1H, s);

IR (KBr) (cm$^{-1}$): 3359, 3278, 1640, 1551, 1234; MS (M$^+$+1): 363.24

Example 14

(±) 1-(3,4-Dihydro-spiro[2H-1-benzopyran-2,1'-cyclobutane]-4-yl)-3-(6-methoxy-1,3-benzothiazol-2-yl)urea $^1$H NMR (DMSO-d$_6$): δ 1.65-2.03 (3H, m); 2.04-2.47 (5H, m); 3.79 (3H, s); 5.02 (1H, m); 6.76-6.86 (1H, d, J=7.2 Hz); 6.87-7.05 (2H, t, J=10.3 Hz); 7.06-7.38 (3H, m); 7.44-7.65 (2H, m); 10.32-10.73 (1H, bs); IR (KBr) (cm$^{-1}$): 3354, 1677, 1577, 1470, 1239
MS (M$^+$+1): 396.18

Example 15

(±) 1-(3,4-Dihydro-spiro[2H-1-benzopyran-2,1'-cyclobutane]-4-yl)-3-(2-methyl-2H-indazol-5-yl)urea $^1$H NMR (DMSO-d$_6$): δ1.65-1.98 (3H, m); 2.05-2.47 (5H, m); 4.09-4.25 (3H, s); 4.93-5.07 (1H, m); 6.61-6.76 (1H, d, J=8.1 Hz); 6.77-6.81 (1H, d, J=8.1 Hz); 6.86-6.98 (1H, t, J=7.5 Hz); 7.08-7.23 (2H, m); 7.24-7.36 (2H, d, J=7.5 Hz); 7.48-7.56 (2H, d, J=6.6 Hz); 8.18-8.26 (1H, s); 8.52-8.64 (1H, s); IR (KBr) (cm$^{-1}$): 3317, 1628, 1566, 1239; MS (M$^+$+1): 363.39

Example 16

(±) 1-(3,4-Dihydro-spiro[2H-1-benzopyran-2,1'-cyclobutane]-4-yl)-3-(5-tert-butyl-1,3,4-thiadiazol-2-yl)urea $^1$H NMR (DMSO-d$_6$): δ 1.23-1.44 (9H, s); 1.65-1.98 (3H, m); 2.03-2.47 (5H, m); 4.90-5.05 (1H, m); 6.74-6.83 (1H, d, J=7.8 Hz); 6.84-6.93 (1H, t, J=7.3 Hz); 6.94-7.04 (1H, m); 7.11-7.23 (1H, m); 10.59-10.98 (1H, bs); IR (KBr) (cm$^{-1}$): 3385, 1697, 1521, 1453, 1238; MS (M$^+$+1): 373.14

Example 17

(±) 1-(3,4-Dihydro-spiro[2H-1-benzopyran-2,1'-cyclobutane]-4-yl)-3-[5-(4-bromophenyl)-1,3-thiazol-2-yl])urea $^1$H NMR (DMSO-d$_6$): δ1.64-2.02 (3H, m); 2.04-2.35 (5H, m); 4.94-5.09 (1H, m); 6.75-6.84 (1H, d, J=7.5 Hz); 6.86-7.01 (2H, m); 7.12-7.28 (2H, m); 7.53-7.68 (3H, d, J=9.9 Hz); 7.74-7.89 (2H, m); 10.52-10.68 (1H, bs); IR (KBr) (cm$^{-1}$): 3339, 1641, 1555, 1233; MS (M$^+$+1): 468.16

Example 18

(±) 1-(3,4-Dihydro-spiro[2H-1-benzopyran-2,1'-cyclobutane]-4-yl)-3-(6-methyl-1,3-benzothiazol-2-yl)urea $^1$H NMR (DMSO-d$_6$): δ 1.68-2.03 (3H, m); 2.04-2.32 (4H, m); 2.34-2.44 (4H, m); 4.92-5.09 (1H, m); 6.72-6.86 (1H, d, J=7.8 Hz); 6.88-6.97 (1H, m); 7.08-7.30 (4H, m); 7.43-7.58 (1H, m); 7.61-7.76 (1H, s); 10.48-10.63 (1H, bs); IR (KBr) (cm$^{-1}$): 3331, 1673, 1527, 1237; MS (M$^+$+1): 380.12

Example 19

(±) 1-(3,4-Dihydro-spiro[2H-1-benzopyran-2,1'-cyclobutane]-4-yl)-3-(1-acetyl-1H-indazol-5-yl)urea $^1$H NMR (DMSO-d$_6$): δ 1.66-2.04 (3H, m); 2.06-2.43 (5H, m); 2.66-2.78 (3H, s) 4.93-5.09 (1H, m); 6.75-6.86 (2H, d, J=7.8 Hz); 6.88-6.98 (1H, t, J=6.9 Hz); 7.13-7.22 (1H, m); 7.25-7.34 (1H, d, J=6.9 Hz); 7.45-7.60 (1H, t, J=7.8 Hz); 7.82-0.97 (2H, t, J=9.1 Hz); 8.39-8.47 (1H, s); 8.95-9.07 (1H, s); IR (KBr) (cm$^{-1}$): 3328, 1734, 1633, 1562, 1239; MS (M$^+$+1): 391.16

Example 20

(±) 1-(3,4-Dihydro-spiro[2H-1-benzopyran-2,1'-cyclobutane]-4-yl)-3-(thieno[2,3-c]pyridine-3-ylurea $^1$H NMR (DMSO-d$_6$): δ 1.50-2.02 (3H, m); 2.03-2.39 (5H, m); 4.86-5.09 (1H, m); 6.60-7.05 (3H, m); 7.08-7.45 (2H, m); 7.65-7.89 (1H, s); 7.90-8.15 (1H, s); 8.44-8.68 (1H, s); 8.90-9.39 (2H, d); IR (KBr) (cm$^{-1}$): 3335, 1686, 1543, 1233; MS (M$^+$+1): 366.35

Example 21

(±) 1-(3,4-Dihydro-spiro[2H-1-benzopyran-2,1'-cyclobutane]-4-yl)-3-([5-(4-bromophenyl)-1,3,4-thiadiazol-2-yl]-)urea $^1$H NMR (DMSO-d$_6$): δ 1.60-2.05 (3H, m); 2.07-2.38 (5H, m); 4.92-5.13 (1H, m); 6.71-6.86 (1H, d, J=7.2 Hz); 6.87-6.98 (1H, t, J=8.4 Hz); 7.02-7.27 (3H, m); 7.64-7.78 (2H, d, J=8.4 Hz); 7.79-7.96 (2H, d, J=7.8 Hz); 10.94-11.12 (1H, bs); IR (Br) (cm$^{-1}$): 3390, 1701, 1448, 1240; MS (M$^+$+1): 471.27

Example 22

(±) 1-(3,4-Dihydro-spiro[2H-1-benzopyran-2,1'-cyclobutane]-4-yl)-3-(4,6-dimethylpyrimidin-2-yl)urea $^1$H NMR (DMSO-d$_6$): δ 1.62-2.03 (3H, m); 2.05-2.37 (1H, m); 4.98-5.15 (1H, m); 6.66-6.97 (3H, m); 7.05-7.36 (2H, m); 9.55-9.86 (2H, bs); IR (KBr) (cm$^{-1}$): 3223, 1681, 1533, 1235; MS (M$^+$+1): 339.20

Example 23

(±) 1-(3,4-Dihydro-spiro[2H-1-benzopyran-2,1'-cyclobutane]-4-yl)-3-(5-chloro-1,3-benzoxazol-2-yl)urea $^1$H NMR (DMSO-d$_6$): δ 1.63-1.91 (3H, m); 1.92-2.39 (5H, m); 5.03-5.21 (1H, m) 6.73-6.87 (1H, d, J=7.8 Hz); 6.88-6.97 (1H, m); 7.09-7.33 (3H, m); 7.46-7.68 (2H, m); 8.52-8.67 (1H, d, J=8.4 Hz); 11.28-11.52 (1H, bs); IR (KBr) (cm$^{-1}$): 3235, 1686, 1557, 1250; MS (M$^+$+1): 384.25

Example 24

(±) 1-(3,4-Dihydro-spiro[2H-1-benzopyran-2,1'-cyclobutane]-4-yl)-3-(5-(4-nitrophenyl)-1,3,4-thiadiazol-2-yl)urea ¹H NMR (DMSO-d$_6$): δ 1.62-2.03 (3H, m); 2.05-2.34 (5H, m); 4.92-5.18 (1H, m); 6.64-7.01 (2H, m); 7.03-7.37 (3H, m); 8.06-8.52 (4H, m); 11.08-11.37 (1H, bs)
IR (KBr) (cm$^{-1}$): 3389, 1701, 1586, 1231; MS (M$^+$+1): 436.12

Example 25

(±) 1-(3,4-Dihydro-spiro[2H-1-benzopyran-2,1'-cyclobutan]-4-yl)-3-(2-furylmethyl)urea ¹H NMR (DMSO-d$_6$): δ 1.60-1.91 (3H, m); 1.95-2.37 (5H, m); 4.13-4.38 (2H, s); 4.81-4.99 (1H, m); 6.18-6.27 (1H, s); 6.28-0.49 (3H, m); 6.69-6.78 (1H, d, J=7.2 Hz); 6.70-6.94 (1H, t, J=6.9 Hz); 7.16-7.23 (2H, m); 7.54-7.65 (1H, s); IR (KBr) (cm$^{-1}$): 3339, 1621, 1483, 1241;
MS (M$^+$+1): 313.24

Example 26

(±) 1-(3,4-Dihydrospiro[2H-1-benzopyran-2,1'-cyclobutan]-4-yl)-3-(quinolin-5-yl)urea

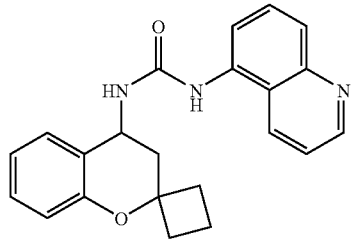

¹H NMR (DMSO-d$_6$): δ 1.70-1.97 (3H, m); 2.12-2.57 (5H, m); 5.02 (1H, m); 6.81 (1H, d, J=8.1 Hz); 6.90-6.99 (2H, m); 7.18 (1H, t, J=7.5 Hz); 7.31 (1H, d, J=7.2 Hz); 7.58 (1H, dd, J=3.9 & 8.4 Hz); 7.71 (2H, m); 8.14 (1H, m); 8.50 (1H, d, J=8.7 Hz); 8.75 (1H, s); 8.91 (1H, m). IR (KBr) (cm$^{-1}$): 3327, 1629, 1560, 1234.MS (M+1): 360.24.

Example 27

(±) 1-(3,4-Dihydrospiro[2H-1-benzopyran-2,1'-cyclobutan]-4-yl)-3-(isoquinolin-8-yl)urea

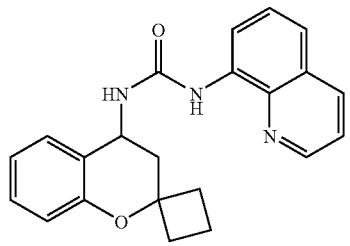

¹H NMR (DMSO-d$_6$): δ 1.70-1.98 (3H, m); 2.12-2.57 (5H, m); 5.03 (1H, m); 6.82 (1H, d, J=8.1 Hz); 6.93 (1H, t, J=7.8 Hz); 7.04 (1H, d, J=8.7 Hz); 7.18 (1H, t, J=7.5 Hz); 7.32 (1H, d, J=7.2 Hz); 7.60 (1H, d, J=8.1 Hz); 7.72 (1H, t, J=8.1 Hz); 7.80 (1H, d, J=6.0 Hz); 8.23 (1H, d, J=7.5 Hz); 8.51 (1H, d, J=5.7 Hz); 9.00 (1H, s); 9.52 (1H, s).IR (KBr) (cm$^{-1}$): 3310, 3272, 1634, 1563, 1233.MS (M$^+$+1): 360.20.

Example 28

N-2,1,3-benzothiadiazol-4-yl-N'-3,3',4,4'-tetrahydro-2'H-spiro[chromene-2,1'-cyclobutan]-4-ylurea (N-2, 1,3-benzothiadiazol-4-yl-N'-3,4-dihydro-2H-spiro[chromene-2,1'-cyclobutan]-4-ylurea)

¹H NMR (DMSO-d$_6$): δ 1.70-1.97 (3H, m); 2.10-2.57 (5H, m); 5.00 (1H, m); 6.80 (1H, d, J=7.8 Hz); 6.90 (1H, t, J=6.9 Hz); 7.17 (1H, t, J=6.9 Hz); 7.26 (1H, d, J=7.2 Hz); 7.32 (1H, d, J=8.1 Hz); 7.50-7.60 (2H, m); 8.07 (1H, d, J=6.0 Hz); 9.35 (1H, s).
IR (KBr) (cm$^{-1}$): 3377, 3312, 3288, 1665, 1555, 1239; MS (M$^+$−1): 349.11.

Example 29

N-2,1,3-benzothiadiazol-4-yl-N'-3,3',4,4'-tetrahydro-2'H-spiro[chromene-2,1'-cyclobutan]-4-ylurea (N-2, 1,3-benzothiadiazol-4-yl-N'-3,4-dihydro-2H-spiro[chromene-2,1'-cyclobutan]-4-ylurea)

This compound was prepared by the same method as described in the example I from 4-amino-3,4-dihydrospiro[2H-1-benzopyran-2,1'-cyclobutane] and phenyl 2,1,3-benzothiadiazol-4-ylcarbamate, M.P. 241-242° C.
¹H NMR (DMSO-d$_6$): δ 1.70-1.96 (3H, m); 2.12-2.57 (5H, m); 5.03 (1H, m); 6.80 (1H, d, J=7.8 Hz); 6.90 (1H, t, J=6.9 Hz); 7.16 (1H, t, J=6.6 Hz); 7.27 (1H, d, J=6.9 Hz); 7.32 (1H, d, J=8.1 Hz); 7.54-7.70 (3H, m); 8.31 (1H, d, J=6.9 Hz); 9.22 (1H, s). IR (KBr) (cm$^{-1}$): 3320, 1568, 1238, 750; MS (M+1): 367.07.

Example 30

N'-(1-oxo-1,2-dihydroisoquinolin-5-yl)-N-3,3',4,4'-tetrahydro-2'H-spiro[chromene-2,1'-cyclobutan]-4-ylurea (N'-(1-oxo-1,2-dihydroisoquinolin-5-yl)-N-3,4-dihydro-2H-spiro[chromene-2,1'-cyclobutan]-4-ylurea)

This compound was prepared by the same method as described in the example I from 4-amino-3,4-dihydrospiro[2H-1-benzopyran-2,1'-cyclobutane] and phenyl 1-oxo-1,2-dihydroisoquinolin-5-ylcarbamate, m.p.>250° C.; ¹H NMR (DMSO-d$_6$): δ 1.70-1.96 (3H, m); 2.04-2.60 (5H, m); 4.98 (1H, m); 6.67 (1H, m); 6.74-6.82 (1H, m); 6.92-6.96 (1H, m); 6.97-7.03 (1H, m); 7.06-7.36 (3H, m); 7.38-7.50 (1H, m); 7.88 (1H, d, J=8.1 Hz); 8.25 (1H, d, J=7.8 Hz); 8.43 (1H, brs) 11.34 (1H, brs); IR (KBr) (cm$^{-1}$): 3436, 1666, 1629, 1238; MS (M$^+$−1): 374.35.

Example 31

(±) 1-(3,4-Dihydro-spiro[2H-1-benzopyran-2,1'-cyclobutan]-4-yl)-3-(pyridin-3-ylmethyl)urea A solution of phenyl 3,4-dihydro-spiro[2H-1-benzopyran-2,1'-cyclobutan]-4-ylcarbamate (1 mmol) and 2-(amino methyl)pyridine (1 mmol) in dimethylsulfoxide was stirred at room temperature in the presence of a base such as triethylamine (2 mmol). Few drops of water were added in the reaction mixture. Product precipitated out, was filtered and washed with water. It was then purified by column chromatography to afford the desired urea as a white solid.

$^1$H NMR (DMSO-$d_6$): (1.70-1.97 (3H, m); 2.12-2.29 (5H, m); 4.30 (2H, d); 4.90 (1H, m); 6.47 (2H; t); 6.74 (1H, d, J=7.2 Hz); 6.85 (1H, d, J=7.5 Hz); 7.12 (2H, m); 7.37 (1H, m); 7.70 (1H, d, J=7.8 Hz); 7.46 (1H, d, J=1.2 Hz); 8.52 (1H, s); IR (KBr) (cm$^{-1}$): 3327, 1625, 1555, 1254; MS (M$^+$+1): 324.26.

The Examples 32 to 39 were prepared according to the method described in Example 31 using appropriately substituted R$^8$.

Example 32

(±) 1-(3,4-Dihydro-spiro[2H-1-benzopyran-2,1'-cyclobutane]-4-yl)-3-(pyridin-2-yl methyl)urea $^1$H NMR (DMSO-$d_6$): δ 1.69-1.90 (3H, m); 2.00-2.36 (5H, m); 4.38 (2H, d, J=5.1 Hz); 4.90 (1H, m); 6.55 (2H, m); 6.75 (1H, d, J=8.1 Hz); 6.85 (1H, t, J=6.9 Hz); 7.14 (2H, m); 7.31 (2H, m); 7.78 (1H, t, J=6.3 Hz); 8.50 (1H, d); IR (KBr) (cm$^{-1}$): 3308, 1626, 1127, 1037, 751; MS (M$^+$+1): 324.21

Example 33

1-((R)-3,4-Dihydrospiro[2H-1-benzopyran-2,1'-cyclobutan]-4-yl)-3-((S)-1-(4-trifluoromethylpyridin-2-yl)pyrrolidin-3-yl)urea

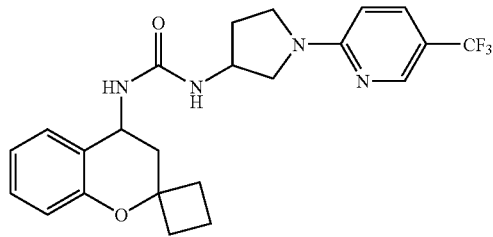

$^1$H NMR (CDCl$_3$): δ1.65-2.00 (5H, m); 2.08-2.44 (5H, m); 3.36 (1H, m); 3.52 (2H, t, J=7.2 Hz); 3.73 (1H, dd, J=6.0 & 10.8 Hz); 4.47 (1H, m); 4.78 (1H, d, J=9.0 Hz); 4.90 (1H, d, J=6.9 Hz); 5.08 (1H, m); 6.33 (1H, d, J=8.7 Hz); 6.78 (1H, d, J=8.4 Hz); 6.83 (1H, t, J=7.8 Hz); 7.11 (1H, t, J=7.5 Hz); 7.20 (1H, d, J=7.2 Hz); 7.58 (1H, d, J=8.4 Hz); 8.35 (1H, s). IR (KBr) (cm$^{-1}$): 3400, 1633, 1613, 1328.MS (M$^+$+1): 447.

Example 34

1-((R)-3,4-Dihydrospiro[2H-1-benzopyran-2,1'-cyclobutan]-4-yl)-3-((R)-1-(4-trifluoromethylpyridin-2-yl)pyrrolidin-3-yl)urea

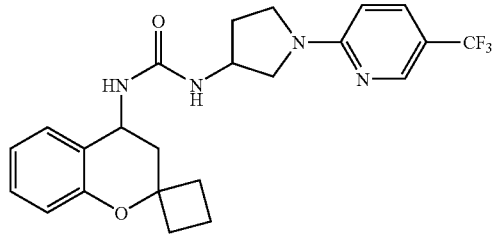

$^1$H NMR (DMSO-$d_6$): δ 1.66-2.00 (5H, m); 2.08-2.32 (5H, m); 3.53 (2H, b); 3.67 (1H, m); 4.33 (1H, m); 4.90 (1H, m); 6.17 (1H, d, J=9.0 Hz); 6.34 (1H, d, J=7.2 Hz); 6.60 (1H, d, J=9.3 Hz); 6.75 (1H, d, J=8.1 Hz); 6.87 (1H, t, J=7.2 Hz); 7.11 (1H, d, J=7.5 Hz); 7.17 (1H, d, J=8.1 Hz); 7.76 (1H, d, J=8.4 Hz); 8.40 (1H, s).IR (KBr)

(cm$^{-1}$): 3367, 1630, 1613, 1560, 1328, 1305, 1111.MS (M$^+$+1): 447.1.

Example 35

1-((S)-3,4-Dihydrospiro[2H-1-benzopyran-2,1'-cyclobutan]-4-yl)-3-((R)-1-(4-trifluoromethylpyridin-2-yl)pyrrolidin-3-yl)urea

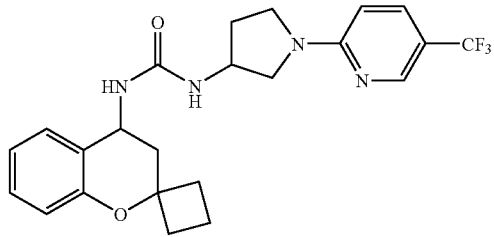

$^1$H NMR (CDCl$_3$): δ 1.65-2.26 (7H, m); 2.33-2.49 (3H, m); 3.41 (1H, m); 3.60 (2H, t, J=7.8 Hz); 3.82 (1H, dd, J=5.7 & 11.1 Hz); 4.43-4.60 (3H, m); 5.12 (1H, m); 6.39 (1H, d, J=8.7 Hz); 6.80 (1H, d, J=8.1 Hz); 6.86 (1H, t, J=7.5 Hz); 7.12-7.25 (2H, m); 7.62 (1H, dd, J=2.7 & 8.7 Hz); 8.39 (1H, s).IR (KBr) (cm$^{-1}$): 3349, 1631, 1613, 1562, 1521, 1328, 1110, 1079.MS (M$^+$+1): 447.

Example 36

1-((S)-3,4-Dihydrospiro[2H-1-benzopyran-2,1'-cyclobutan]-4-yl)-3-((S)-1-(4-trifluoromethylpyridin-2-yl)pyrrolidin-3-yl)urea

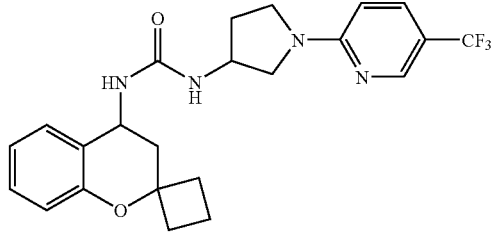

$^1$H NMR (CDCl$_3$): δ1.65-2.26 (7H, m); 2.33-2.49 (3H, m); 3.41 (1H, m); 3.61 (2H, t, J=7.8 Hz); 3.82 (1H, dd, J=5.7 & 10.8 Hz); 4.44-4.60 (3H, m); 5.13 (1H, m); 6.38 (1H, d, J=9.0 Hz); 6.80 (1H, d, J=8.4 Hz); 6.88 (1H, t, J=7.2 Hz); 7.12-7.25 (2H, m); 7.60 (1H, m); 8.38 (1H, s).IR (KBr) (cm$^{-1}$): 3369, 1631, 1613, 1304, 1110, 1079.MS (M$^+$+1): 447.

Example 37

1-(S)-3,4-Dihydro spiro[2H-1-benzopyran-2,1'-cyclobutan]-4-yl)-3-(pyridin-4-yl)methyl urea

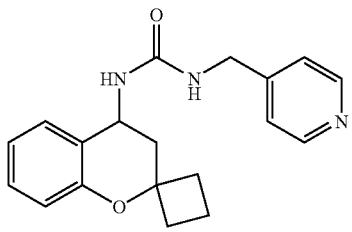

$^1$H NMR (DMSO-d$_6$): δ 1.69-1.90 (3H, m); 2.00-2.36 (5H, m); 4.31 (2H, d, J=4.8 Hz); 4.90 (1H, m); 6.54 (2H, m); 6.76 (1H, d, J=8.1 Hz); 6.87 (1H, t, J=6.9 Hz); 7.12 (1H, d, J=7.5 Hz); 7.17 (1H, d, J=8.4 Hz); 7.28 (2H, m); 7.52 (2H, m).IR (KBr) (cm$^{-1}$): 3370, 1630, 1115, 1063.MS (M$^+$+1): 324.21.

Example 38

1-((S)-3,4-Dihydrospiro[2H-1-benzopyran-2,1'-cyclobutan]-4-yl)-3-(4-trifluoromethylbenzyl)urea

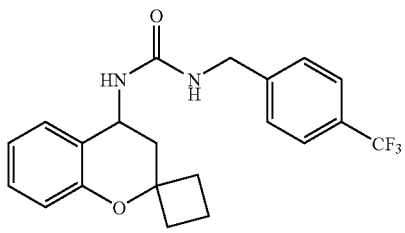

$^1$H NMR (DMSO-d$_6$): δ 1.30 (2H, m); 2.08 (2H, m); 2.28 (2H, m); 4.36 (2H, dd); 4.89 (1H, m); 6.49 (2H, dd, J=7.2 Hz); 6.74 (1H, dd, J=6.9 Hz); 6.86 (1H, t); 7.13 (2H, m); 7.15 (2H, d, J=7.2 Hz); 7.71 (2H, d, J=7.8 Hz).IR (KBr) (cm$^{-1}$): 3351, 3306, 2943, 1627, 1574, 1455, 1421, 1236, 1120.MS (M$^+$+1): 391.07.

Example 39

N-3,4-dihydrospiro[chromene-2,1'-cyclobutan]-4-ylpiperidine-1-carboxamide

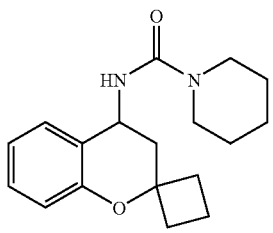

$^1$H NMR (DMSO-d$_6$): δ 1.39-1.60 (m, 7H), 1.65-1.90 (m, 4H), 2.01-2.18 (m, 4H), 2.20-2.36 (m, 4H), 4.98 (1H, m); 6.73 (2H, dd, J=6.3 Hz); 6.86 (1H, t); 7.10 (1H, m).IR (KBr) (cm$^{-1}$): 3318, 1618, 1528, 1235, 760.

The first step of Examples 40 to 62 were carried out using the procedure described in step 1 of Example 3 with an appropriately substituted acetophenone. Step II to IV were carried out by following the procedure as described in step II to IV in Example 1.

Example 40

(±)-1-(3,4-Dihydro-6-methyl-spiro[2H-1-benzopyran-2,1'-cyclobutane]-4-yl)-3-(isoquinolin-5-yl)urea Step I: 3,4-Dihydro-6-methyl-4-oxo-spiro[2H-1-benzopyran-2,1'-cyclobutane]

$^1$H NMR (CDCl$_3$): δ1.24-1.46 (2H, m); 1.60-1.79 (4H, m); 1.82 (3H, s); 2.92 (2H, s); 6.52 (1H, d, J=8.4 Hz); 6.94 (1H, m); 7.08 (1H, s).

Step II: 3,4-Dihydro-4-hydroxyimino-6-methyl-spiro[2H-1-benzopyran-2,1'-cyclobutane]

$^1$H NMR (DMSO-d$_6$): δ 1.63-1.84 (2H, m); 1.93-2.14 (4H, m); 2.21 (3H, s), 2.5 (2H, s), 6.77 (1H, d, J=8.1 Hz); 7.04 (1H, d, J=8.1 Hz); 7.52 (1H, s); 11.23 (1H, s).

Step III: (±) 4-Amino-3,4-dihydro-6-methyl-spiro[2H-1-benzopyran-2,1'-cyclobutane]hydrochloride $^1$H NMR (DMSO-d$_6$): δ 1.67-2.36 (11H, m); 4.50 (1H, m); 6.72 (1H, d, J=8.1 Hz); 7.03 (1H, d, J=8.1 Hz); 7.46 (1H, s); 8.80 (3H, b).

Step IV: (±) 1-(3,4-Dihydro-6-methyl-spiro[2H-1-benzopyran-2,1'-cyclobutane]-4-yl)-3-(isoquinolin-5-yl)urea $^1$H NMR (DMSO-d$_6$): δ 1.71-1.94 (3H, m); 2.08-2.44 (5H, m); 2.22 (1H, s); 4.98 (1H, m); 6.71 (1H, d, J=7.8 Hz); 7.00 (1H, t, J=10.5 Hz); 7.10 (1H, s); 7.63 (1H, t, J=8.1 Hz); 7.76 (1H, d, J=8.1 Hz); 7.93 (1H, d, J=6.3 Hz); 8.39 (1H, d, J=7.2 Hz); 8.55 (1H, d, J=6.0 Hz); 8.71 (1H, s); 9.29 (1H, s); IR (KBr) (cm$^{-1}$): 3341, 3276, 2935, 1668, 1576, 1566, 1495, 1220; MS (M$^+$+1): 375.1

Example 41

(±) 1-(3,4-Dihydro-7-methyl-spiro[2H-1-benzopyran-2,1'-cyclobutane]-4-yl-3-(isoquinolin-5-yl)urea Step I: 3,4-Dihydro-7-methyl-4-oxo-spiro[2H-1-benzopyran-2,1'-cyclobutane]

Step II: 3,4-Dihydro-4-hydroxyimino-7-methyl-spiro[2H-1-benzopyran-2,1'-cyclobutane]

$^1$H NMR (DMSO-d$_6$): δ 1.69-1.76 (2H, m); 1.93-2.14 (4H, m); 2.22 (3H, s), 2.88 (2H, s), 6.70 (2H, m); 7.57 (1H, d, J=8.1 Hz); 11.14 (1H, s).

Step III: (±) 4-Amino-3,4-dihydro-7-methyl-spiro[2H-1-benzopyran-2,1'-cyclobutane].HCl $^1$H NMR (DMSO-d$_6$): δ 1.65-2.30 (1H, m); 4.51 (1H, m); 6.67 (1H, s), 6.78 (1H, d, J=8.5 Hz); 7.44 (1H, t, J=8.1 Hz); 8.69 (3H, b).

Step IV: (±) 1-(3,4-Dihydro-7-methyl-spiro[2H-1-benzopyran-2,1'-cyclobutane]-4-yl)-3-(isoquinolin-5-yl)urea $^1$H NMR (DMSO-$d_6$): δ 1.76-1.94 (3H, m); 2.13-2.44 (5H, m); 2.24 (3H, s); 4.97 (1H, m); 6.64 (1H, s); 6.75 (1H, d, J=7.8 Hz); 6.99 (1H, d, J=8.1 Hz); 7.18 (1H, d, J=7.8 Hz); 7.64 (1H, t, J=8.1 Hz); 7.77 (1H, d, J=8.1 Hz); 7.94 (1H, d, J=6.0 Hz); 8.39 (1H, d, J=7.2 Hz); 8.56 (1H, d, J=6.0 Hz); 8.73 (1H, s); 9.29 (1H, s); IR (KBr) (cm$^{-1}$): 3324, 1625, 1560, 1233; MS (M$^+$+1): 374.2

Example 42

(±) 1-(3,4-Dihydro-6-fluoro-spiro[2H-1-benzopyran-2,1'-cyclobutane]-4-yl)-3-(isoquinolin-5-yl)urea

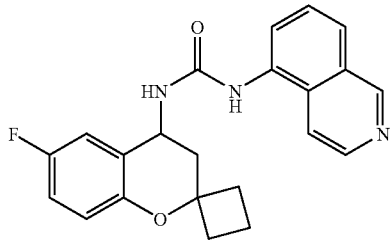

Step I: 3,4-Dihydro-6-fluoro-4-oxo-spiro[2H-1-benzopyran-2,1'-cyclobutane]

$^1$H NMR (CDCl$_3$): δ 1.66-1.80 (1H, m); 1.86-1.99 (1H, m); 2.13-2.21 (2H, m); 2.24-2.39 (2H, m); 2.90 (2H, s); 6.96 (1H, dd, J=4.5 & 9.0 Hz); 7.20 (1H, 8 lines); 7.50 (1H, dd, J=3.3 & 8.4 Hz).

Step II: 3,4-Dihydro-6-fluoro-4-hydroxyimino-spiro[2H-1-benzopyran-2,1'-cyclobutane]

Step III: (±) 4-Amino-3,4-dihydro-6-fluoro-spiro[2H-1-benzopyran-2,1'-cyclobutane]

$^1$H NMR (DMSO-$d_6$): δ 1.62-2.56 (8H, m); 4.50 (1H, m); 6.85 (1H, m); 7.07 (1H, t, J=9.0 Hz); 7.46 (1H, dd, J=9.0 Hz); 8.29 (2H, b).

Resolution of the Racemate:

To a solution of (±) 4-Amino-3,4-dihydro-6-fluorospiro[2H-1-benzopyran-2,1'-cyclobutane] (2.42 mmol, 500 mg), in isopropyl alcohol (12 ml) was added a solution of R (−) mandelic acid (2.18 mmol, 333 mg) and stirred for 12-24 h at room temperature. The precipitated solid was filtered, dried and neutralized with 2N NaOH to obtain (−) 4-amino-3,4-dihydro-6-fluoro-spiro[2H-1-benzopyran-2,1'-cyclobutane] amine as yellow oil (60 mg). HPLC purity: >98%, chiral purity>98%. To obtain (+) 4-Amino-3,4-dihydro-6-fluorospiro[2H-1-benzopyran-2,1'-cyclobutane], the same process as above was followed using S (+) mandelic acid instead of R (−) mandelic acid as the resolving agent.

Step IV: (±) 1-(3,4-Dihydro-6-fluoro-spiro[2H-1-benzopyran-2,1'-cyclobutane]-4-yl)-3-(isoquinolin-5-yl)urea $^1$H NMR (DMSO-$d_6$): δ 1.70-1.96 (3H, m); 2.08-2.46 (5H, m); 5.00 (1H, m); 6.84 (1H, dd, J=5.1 & 9.0 Hz); 7.00-7.10 (3H, m); 7.64 (1H, t, J=7.8 Hz); 7.78 (1H, d, J=8.1 Hz); 7.94 (1H, d, J=6.0 Hz); 8.36 (1H, d, J=7.5 Hz); 8.56 (1H, d, J=6.3 Hz); 8.77 (1H, s); 9.29 (1H, s); IR (KBr) (cm$^{-1}$): 3315, 2937, 1633, 1567, 1487, 1212; MS (M$^+$+1): 379.2; $^1$H NMR (DMSO-$d_6$) for hydrochloride salt: δ 1.69-1.94 (3H, m); 2.09-2.48 (5H, m); 5.01 (1H, m); 6.83 (1H, dd, J=4.8 & 8.7 Hz); 6.99-7.10 (2H, m); 7.62 (1H, m); 7.93 (1H, t, J=8.1 Hz); 8.10 (1H, d, J=8.1 Hz); 8.65-8.72 (3H, m); 9.54-9.59 (1H, m); 9.78 (1H, d, J=2.4 Hz); IR (KBr) (cm$^{-1}$): 3280, 2934, 2679, 1698, 1544, 1486, 1211, 813.

Example 43

(+) 1-(3,4-Dihydro-6-fluoro-spiro[2H-1-benzopyran-2,1'-cyclobutane]-4-yl)-3-(isoquinolin-5-yl)urea (−) 4-Amino-3,4-dihydro-6-fluoro-spiro[2H-1-benzopyran-2,1'-cyclobutane] was reacted with phenyl N-(5-isoquinolinyl)carbamate to form compound of Formula 43.

$^1$H NMR (DMSO-$d_6$): δ 1.73-1.95 (3H, m); 2.08-2.46 (5H, m); 4.66 (1H, m); 5.00 (1H, m); 6.84 (1H, dd, J=5.1 & 9.0 Hz); 7.00-7.10 (3H, m); 7.64 (1H, t, J=7.8 Hz); 7.78 (1H, d, J=8.1 Hz); 7.94 (1H, d, J=6.0 Hz); 8.36 (1H, d, J=7.5 Hz); 8.56 (1H, d, J=6.3 Hz); 8.77 (1H, s); 9.29 (1H, s); IR (KBr) (cm$^{-1}$): 3367, 2934, 1642, 1552, 1489, 1211, 1169, 815; MS (M$^+$+1): 379.2

Example 44

(−) 1-(3,4-Dihydro-6-fluorospiro[2H-1-benzopyran-2,1'-cyclobutane]-4-yl)-3-(isoquinolin-5-yl)urea (+) 4-Amino-3,4-dihydro-6-fluoro-spiro[2H-1-benzopyran-2,1'-cyclobutane] was reacted with phenyl N-(5-isoquinolinyl)carbamate to form compound of Formula 44.

$^1$H NMR (DMSO-$d_6$): δ 1.73-1.95 (3H, m); 2.08-2.46 (5H, m); 4.66 (1H, m); 5.01 (1H, m); 6.84 (1H, dd, J=5.1 & 9.0 Hz); 7.00-7.10 (3H, m); 7.64 (1H, t, J=7.8 Hz); 7.78 (1H, d, J=8.1 Hz); 7.94 (1H, d, J=6.0 Hz); 8.36 (1H, d, J=7.5 Hz); 8.56 (1H, d, J=6.3 Hz); 8.77 (1H, s); 9.29 (1H, s); IR (KBr) (cm$^{-1}$): 3350, 2933, 1644, 1552, 1488, 1256, 1212, 1034, 815; MS (M$^+$+1): 379.2

Example 45

(±) 1-(3,4-Dihydro-6-hydroxy-spiro[2H-1-benzopyran-2,1'-cyclobutane]-4-yl)-3-(isoquinolin-5-yl)urea

Step I: 3,4-Dihydro-6-hydroxy-4-oxo-spiro[2H-1-benzopyran-2,1'-cyclobutane]

$^1$H NMR (DMSO-$d_6$): δ 1.71-1.82 (2H, m); 2.04-2.21 (4H, m); 2.90 (2H, s); 6.90 (1H, d, J=9.0 Hz); 6.99-7.05 (2H, m); 9.40 (1H, s).

Step II: 3,4-Dihydro-6-hydroxy-4-hydroxyimino-spiro[2H-1-benzopyran-2,1'-cyclobutane]

Step III: (±) 4-Amino-3,4-dihydro-6-hydroxy-spiro[2H-1-benzopyran-2,1'-cyclobutane]

$^1$H NMR (DMSO-$d_6$): δ 1.63-2.56 (8H, m); 4.44 (1H, m); 6.62 (1H, d, J=8.1 Hz); 6.72 (1H, d, J=8.1 Hz); 6.97 (1H, d, J=8.4 Hz); 8.82 (3H, b); 9.22 (1H, s).

47

Step IV: (±) 1-(3,4-Dihydro-6-hydroxy-spiro[2H-1-benzopyran-2,1'-cyclobutane]-4-yl)-3-(isoquinolin-5-yl)urea $^1$H NMR (DMSO-d$_6$): δ 1.71-1.93 (3H, m); 2.08-2.44 (5H, m); 4.66 (1H, m); 4.97 (1H, m); 6.54-6.64 (2H, m); 7.76 (1H, d, J=8.1 Hz); 7.94 (1H, d, J=6.3 Hz); 8.39 (1H, d, J=6.9 Hz); 8.55 (1H, d, J=6.3 Hz); 8.73 (1H, s); 8.92 (1H, s); 9.29 (1H, s).

Example 46

(±) 1-(3,4-Dihydro-7-hydroxy-spiro[2H-1-benzopyran-2,1'-cyclobutane]-4-yl)-3-(isoquinolin-5-yl)urea

Step I: 7-Benzyloxy-3,4-dihydro-4-oxo-spiro[2H-1-benzopyran-2,1'-cyclobutane]

$^1$H NMR (CDCl$_3$): δ 1.66-1.79 (2H, m); 2.05-2.30 (4H, m); 2.88 (2H, s); 3.34 (3H, s); 5.17 (2H, s); 6.64 (1H, d, J=2.1 Hz); 6.69 (1H, dd, J=2.7 & 9.0 Hz); 7.30-7.48 (5H, m); 7.65 (1H, d, J=8.7 Hz).

Step II: 7-Benzyloxy-3,4-dihydro-4-hydroxyimino-spiro[2H-1-benzopyran-2,1'-cyclobutane]

Step III: (±) 4-Amino-3,4-dihydro-7-hydroxy-spiro[2H-1-benzopyran-2,1'-cyclobutane]

This compound was prepared by hydrogenation of 7-Benzyloxy-3,4-Dihydro-4-hydroxyimino-spiro[2H-1-benzopyran-2,1'-cyclobutane] in presence of 10% Pd/C in methanol. The amine was isolated as hydrochloride salt.

$^1$H NMR (DMSO-d$_6$): δ 1.65-2.36 (8H, m); 4.45 (1H, m); 6.40 (1H, d, J=−8.4 Hz); 7.31-7.42 (2H, m); 8.50 (3H, b); 9.67 (1H, s).

Step V: (±) 1-(3,4-Dihydro-7-hydroxy-spiro[2H-1-benzopyran-2,1'-cyclobutane]-4-yl)-3-(isoquinolin-5-yl)urea $^1$H NMR (DMSO-d$_6$): δ 1.72-1.92 (3H, m); 2.08-2.38 (5H, m); 4.66 (1H, m); 4.90 (1H, m); 6.19 (1H, s); 6.36 (1H, d, J=8.1 Hz); 6.92 (1H, d, J=8.1 Hz); 7.07 (1H, d, J=8.4 Hz); 7.62 (1H, d, J=7.8 Hz); 7.75 (1H, d, J=7.8 Hz); 7.93 (1H, d, J=6.3 Hz); 8.39 (1H, d, J=7.8 Hz); 8.55 (1H, d, J=6.0 Hz); 8.68 (1H, s); 9.28 (1H, s); 9.38 (1H, s).

IR (KBr) (cm$^{-1}$): 3304, 1622, 1563, 1109; MS (M$^+$+1): 376.2

Example 47

(±) 1-(3,4-Dihydro-7-methoxy-spiro[2H-1-benzopyran-2,1'-cyclobutane]-4-yl)-3-(isoquinolin-5-yl)urea

Step I: 3,4-Dihydro-7-methoxy-4-oxo-spiro[2H-1-benzopyran-2,1'-cyclobutane]

$^1$H NMR (CDCl$_3$): δ 1.66-1.76 (1H, m); 1.86-1.99 (1H, m); 2.12-2.21 (2H, m); 2.27-2.38 (2H, m); 2.85 (2H, s); 3.84 (3H, s); 6.42 (1H, d, J=2.4 Hz); 6.56 (1H, dd, J=2.4 & 9.0 Hz); 7.80 (1H, d, J=9.0 Hz).

48

Step II: 3,4-Dihydro-4-hydroxyimino-7-methoxy-spiro[2H-1-benzopyran-2,1'-cyclobutane]

Step III: (±) 4-Amino-3,4-dihydro-7-methoxy-spiro[2H-1-benzopyran-2,1'-cyclobutane]

$^1$H NMR (DMSO-d$_6$): δ 1.67-2.36 (8H, m); 4.57 (1H, m); 6.85 (1H, d, J=8.1 Hz); 6.98 (1H, t, J=8.1 Hz); 7.26 (1H, d, J=8.4 Hz); 7.59 (1H, d, J=7.5 Hz); 8.73 (3H, b).

Step IV: (±) 1-(3,4-Dihydro-7-methoxy-spiro[2H-1-benzopyran-2,1'-cyclobutane]-4-yl)-3-(isoquinolin-5-yl)urea $^1$H NMR (DMSO-d$_6$): δ 1.72-1.94 (3H, m); 2.08-2.43 (5H, m); 4.94 (1H, m); 6.39 (1H, s); 6.53 (1H, d, J=9.0 Hz); 6.96 (1H, d, J=7.8 Hz); 7.19 (1H, d, J=8.4 Hz); 7.63 (1H, t, J=7.2 Hz); 7.76 (1H, d, J=8.1 Hz); 7.93 (1H, d, J=6.0 Hz); 8.38 (1H, d, J=7.5 Hz); 8.55 (1H, d, J=5.7 Hz); 8.71 (1H, s); 9.29 (1H, s); IR (KBr) (cm$^{-1}$): 3314, 1631, 1563; MS (M$^+$+1): 390.1

Example 48

1-(6,8-Difluoro-3,4-dihydro-spiro[2H-1-benzopyran-2,1'-cyclobutane]-4-yl)-3-(isoquinolin-5-yl)urea

Step I: 3,4-Dihydro-6,8-difluoro-4-oxo-spiro[2H-1-benzopyran-2,1'-cyclobutane]

$^1$H NMR (DMSO-d$_6$): δ 1.71-1.87 (2H, m); 2.10-2.32 (4H, m); 3.08 (2H, s); 7.30 (1H, m); 7.70 (1H, m).

Step II: 3,4-Dihydro-6,8-difluoro-4-hydroxyimino-spiro[2H-1-benzopyran-2,1'-cyclobutane]

$^1$H NMR (DMSO-d$_6$): δ 1.69-1.86 (2H, m); 1.97-2.25 (4H, m); 2.99 (2H, s); 7.25-7.36 (2H, m); 11.71 (1H, s).

Step III: (±) 4-Amino-3,4-dihydro-6,8-difluorospiro[2H-1-benzopyran-2,1'-cyclobutane]

$^1$H NMR (CDCl$_3$): δ 1.62-2.56 (8H, m); 4.01 (1H, m); 6.73 (2H, m); 6.95 (1H, d).

This compound was resolved by using both R (−) and S (+) mandelic acid in IPA as solvent. To a solution of 6,8-difluoro-3,4-dihydro-spiro[chromene-2,1'-cyclobutan]-4-amine (1 mmol) in isopropyl alcohol at room temperature under stirring, Add a solution of R (−) mandelic acid in IPA slowly within 10 mins under stirring, stir the reaction mass for 1-2 hrs at room temperature and filter it to afford (−) 4-Amino-3,4-dihydro-6,8-difluorospiro[2H-1-benzopyran-2,1'-cyclobutane] in 35-40% yield (w/w). Using S (+) mandelic acid the (+) enantiomer was obtained similarly.

Step IV: (±) 1-(6,8-Difluoro-3,4-Dihydro-spiro[2H-1-benzopyran-2,1'-cyclobutane]-4-yl)-3-(isoquinolin-5-yl)urea $^1$H NMR (DMSO-d$_6$): δ 1.70-1.96 (3H, m); 2.08-2.46 (5H, m); 5.03 (1H, m); 6.94 (1H, d, J=9.0 Hz); 7.11 (1H, d, J=8.7 Hz); 7.21 (1H, t, J=7.8 Hz); 7.60 (1H, t, J=7.5 Hz); 7.94 (1H, d, J 7.2 Hz); 8.33 (1H, d, J=7.8 Hz); 8.56 (1H, d, J=7.8 Hz); 8.79 (1H, s); 9.29 (1H, s); IR (KBr) (cm$^{-1}$): 3313, 2935, 1633, 1568, 1483, 1226; MS (M$^+$+1): 397.1

Example 49

(±) 1-(8-Chloro-3,4-dihydro-spiro[2H-1-benzopyran-2,1'-cyclobutane]-4-yl)-3-(isoquinolin-5-yl)urea

Step 1: 8-Chloro-3,4-Dihydro-4-oxo-spiro[2H-1-benzopyran-2,1'-cyclobutane]

$^1$H NMR (CDCl$_3$): δ 1.64-1.79 (1H, m); 1.90-2.05 (1H, m); 2.15-2.26 (2H, m); 2.34-2.48 (2H, m); 2.94 (2H, s); 6.94 (1H, t, J=8.4 Hz); 7.56 (1H, dd, J=1.5 & 7.8 Hz); 7.79 (1H, dd, J=1.5 & 8.4 Hz).

Step II: 8-Chloro-3,4-Dihydro-4-hydroxyimino-spiro[2H-1-benzopyran-2,1'-cyclobutane]$^1$H NMR (DMSO-d$_6$): δ 1.69-1.86 (2H, m); 2.00-2.20 (4H, m); 2.99 (3H, s), 6.94 (1H, t, J=7.8 Hz), 7.44 (1H, d, J=8.1 Hz); 7.70 (1H, d, J=8.1 Hz); 11.53 (1H, s).

Step III: (±) 4-Amino-8-chloro-3,4-dihydro-spiro[2H-1-benzopyran-2,1'-cyclobutane].HCl $^1$H NMR (DMSO-d$_6$): δ 1.68-2.03 (4H, m); 2.23 (2H, brm); 2.39-2.62 (2H, m), 4.64 (1H, m); 7.00 (1H, t, J=7.5 Hz); 7.44 (1H, d, J=7.5 Hz); 7.55 (1H, d, J=7.5 Hz); 8.72 (3H, b).

Step V: (±) 1-(8-Chloro-3,4-dihydro-spiro[2H-1-benzopyran-2,1'-cyclobutane]-4-yl)-3-(isoquinolin-5-yl)urea H NMR (DMSO-d$_6$): δ 1.75-2.45 (8H, m); 5.06 (1H, m); 6.93 (1H, t, J=7.5 Hz); 7.10 (1H, d, J=8.4 Hz); 7.27 (1H, d, J=7.5 Hz); 7.33 (1H, d, J=7.5 Hz); 7.63 (1H, t, J=8.4 Hz); 7.78 (1H, d, J=7.8 Hz); 7.94 (1H, d, J=6.0 Hz); 8.37 (1H, d, J=7.5 Hz); 8.57 (1H, d, J=6.0 Hz); 8.78 (1H, s); 9.29 (1H, m).

Example 50

(±) 1-(3,4-Dihydro-6-fluoro-spiro[2H-1-benzopyran-2,1'-cyclobutane]-4-yl)-3-(isoquinolin-5-yl)urea

Step I: 3,4-Dihydro-7-fluoro-4-oxo-spiro[2H-1-benzopyran-2,1'-cyclobutane]

$^1$H NMR (CDCl$_3$): δ 1.64-1.80 (1H, m); 1.88-2.01 (1H, m); 2.13-2.23 (2H, m); 2.27-2.40 (2H, m); 2.89 (2H, s); 6.66-6.74 (2H, m); 7.84-7.89 (1H, dd, J=6.9 & 8.7 Hz).

Step II: 3,4-Dihydro-7-fluoro-4-hydroxyimino-spiro[2H-1-benzopyran-2,1'-cyclobutane]

$^1$H NMR (DMSO-d$_6$): δ 1.69-1.86 (2H, m); 1.97-2.19 (4H, m); 2.94 (2H, s); 6.79 (2H, m); 7.75 (1H, t, J=8.8 Hz); 11.31 (1H, s).

Step III: (±) 4-Amino-3,4-dihydro-7-fluoro-spiro[2H-1-benzopyran-2,1'-cyclobutane]

$^1$H NMR (DMSO-d$_6$): δ 1.63-2.06 (4H, m); 2.14-2.20 (2H, m); 2.29-2.39 (1H, m); 2.50-2.59 (1H, m); 4.55 (1H, m); 6.75 (1H, dd, J=8.1 Hz); 6.85 (1H, t, J=8.1 Hz); 7.68 (1H, m); 8.82 (3H, b).

Step IV: (±) 1-(3,4-Dihydro-7-fluoro-spiro[2H-1-benzopyran-2,1'-cyclobutane]-4-yl)-3-(isoquinolin-5-yl)urea $^1$H NMR (DMSO-d$_6$): δ 1.70-1.98 (3H, m); 2.16-2.48 (5H, m); 4.99 (1H, m); 6.68 (1H, dd, J=2.4 & 10.5 Hz); 6.78 (1H, t, J=2.7 & 8.4 Hz); 7.07 (1H, d, J=8.4 Hz); 7.33 (1H, t, J=7.8 Hz); 7.66 (1H, t, J=7.5 Hz); 7.80 (1H, d, J=7.5 Hz); 7.98 (1H, d, J=6.0 Hz); 8.39 (1H, d, J=7.5 Hz); 8.57 (1H, d, J=6.0 Hz); 8.79 (1H, s); 9.33 (1H, s).

The hydrochloride salt was prepared using ethyl acetate saturated with hydrochloric acid.

$^1$H NMR (DMSO-d$_6$) for hydrochloride salt: δ 1.70-1.99 (3H, m); 2.096-2.46 (5H, m); 5.00 (1H, m); 6.67 (1H, dd, J=2.7 & 10.8 Hz); 6.76 (1H, t, J=2.7 & 8.7 Hz); 7.32 (1H, d, J=7.2 Hz); 7.61 (1H, m); 7.94 (1H, t, J=7.8 Hz); 8.10 (1H, d, J=7.8 Hz); 8.73 (3H, m); 9.61 (1H, m); 9.81 (1H, s).

Example 51

(±) 1-(3,4-Dihydro-6-methoxy-spiro[2H-1-benzopyran-2,1'-cyclobutane]-4-yl)-3-(isoquinolin-5-yl)urea

Step I: 6-methoxy-3,4-dihydro-4-oxo-spiro[2H-1-benzopyran-2,1'-cyclobutane]

To a solution of 3,4-Dihydro-6-hydroxy-4-oxo-spiro[2H-1-benzopyran-2,1'-cyclobutane] (Example 12) (10 mmol) in dimethylformamide, iodomethane (12 mmol) and potassium carbonate (12 mmol) was added and the reaction mixture was stirred at rt for 12 h. Solvent was then evaporated and the residue was dissolved in ethyl acetate. Organic layer was washed with water, brine and separated. It was then dried on anhydrous Na$_2$SO$_4$ and concentrated to afford the desired product as oil.

$^1$H NMR (CDCl$_3$): δ1.65-1.78 (1H, m); 1.86-1.99 (1H, m); 2.11-2.19 (2H, m); 2.25-2.36 (2H, m); 2.89 (2H, s); 3.80 (3H, s); 6.92 (1H, d, J=9.3 Hz); 7.09 (1H, dd, J=3.0 & 9.3 Hz); 7.28 (1H, d, J=2.7 Hz).

Step II: 3,4-Dihydro-4-hydroxyimino-6-methoxy-spiro[2H-1-benzopyran-2,1'-cyclobutane]

Step III: (±) 4-Amino-3,4-dihydro-6-methoxy-spiro[2H-1-benzopyran-2,1'-cyclobutane]

$^1$H NMR (DMSO-d$_6$): δ 1.67-1.2.36 (8H, m); 4.57 (1H, m); 6.85 (1H, d, J=8.1 Hz); 6.98 (1H, t, J=8.1 Hz); 7.26 (1H, d, J=8.4 Hz); 7.59 (1H, d, J=7.5 Hz); 8.73 (3H, b).

Step IV: (±) 1-(3,4-Dihydro-6-methoxy-spiro[2H-1-benzopyran-2,1'-cyclobutane]-4-yl)-3-(isoquinolin-5-yl)urea $^1$H NMR (DMSO-d$_6$): δ 1.71-1.94 (3H, m); 2.08-2.43 (5H, m); 4.97 (1H, m); 6.74-6.84 (3H, m); 7.04 (1H, d, J=8.1 Hz); 7.63 (1H, t, J=7.8 Hz); 7.77 (1H, d, J=8.1 Hz); 7.93 (1H, d, J=5.7 Hz); 8.36 (1H, d, J=7.8 Hz); 8.55 (1H, d, J=6.3 Hz); 8.72 (1H, s); 9.29 (1H, s); IR (KBr) (cm$^{-1}$): 3321, 1629, 1561, 1489, 1217; MS (M$^+$+1): 390.1.

Example 52

(±) 1-(6-Cyclopentyloxy-3,4-dihydro-spiro[2H-1-benzopyran-2,1'-cyclobutane]-4-yl)-3-(isoquinolin-5-yl)urea

Step I: 6-Cyclopentyloxy-3,4-dihydro-4-oxo-spiro[2H-1-benzopyran-2,1'-cyclobutane]

To a solution of 3,4-Dihydro-6-hydroxy-4-oxo-spiro[2H-1-benzopyran-2,1'-cyclobutane] (from example 12) (10 mmol) in DMF, cyclopentyl bromide (12 mmol) and K$_2$CO$_3$ (12 mmol) was added and the reaction mixture was heated at 60° C. for 12 h. Solvent was then evaporated and the residue was dissolved in ethyl acetate. Organic layer was washed with water, brine and separated. It was then dried on anhydrous Na$_2$SO$_4$ and concentrated to afford the desired product as oil.

$^1$H NMR (CDCl$_3$): δ 1.56-1.98 (10H, m); 2.1-2.21 (2H, m); 2.24-2.37 (2H, m); 2.87 (2H, s); 4.72 (1H, m); 6.89 (1H, d, J=9.0 Hz); 7.05 (1H, dd J=3.0 & 9.0 Hz); 7.26 (1H, d, J=3.0 Hz).

Step II: 6-cyclopentyloxy-3,4-dihydro-4-hydroxy-imino-spiro[2H-1-benzopyran-2,1'-cyclobutane]

Step III: (±) 4-Amino-6-cyclopentyloxy-3,4-dihydro-spiro[2H-1-benzopyran-2,1'-cyclobutane]

$^1$H NMR CDCl$_3$): δ1.55-2.45 (16H, m); 4.17 (1H, m); 4.66 (1H, m); 6.71 (2H, m); 7.01 (1H, d, J=2.1 Hz).

Step IV: (±) 1-(6-Cyclopentyloxy-3,4-dihydro-spiro[2H-1-benzopyran-2,1'-cyclobutane]-4-yl)-3-(iso-quinolin-5-yl)urea This compound was prepared in the same manner from (±) 4-Amino-6-cyclopentyloxy 3,4-dihydro-spiro[2H-1-benzopyran-2,1'-cyclobutane] as in step 1V of example 1.

$^1$H NMR (DMSO-d$_6$): δ 1.50-1.93 (1H, m); 2.08-2.44 (5H, m); 4.66 (1H, m); 4.97 (1H, m); 6.74-6.79 (3H, m); 7.21 (1H, d, J=8.1 Hz); 7.64 (1H, t, J=8.1 Hz); 7.78 (1H, d, J=8.1 Hz); 7.93 (1H, d, J=6.0 Hz); 8.35 (1H, d, J=7.8 Hz); 8.55 (1H, d, J=6.3 Hz); 8.74 (1H, s); 9.29 (1H, s); IR (KBr) (cm$^{-1}$): 3368, 1641, 1553, 1489, 1169; MS (M$^+$+1):

Example 53

(±) 1-(7-Cyclopentyloxy-3,4-dihydro-spiro[2H-1-benzopyran-2,1'-cyclobutane]-4-yl)-3-(isoquinolin-5-yl)urea Step I: 7-Cyclopentyloxy-3,4-dihydro-4-oxo-spiro [2H-1-benzopyran-2,1'-cyclobutane]

To a solution of 3,4-Dihydro-7-hydroxy-4-oxo-spiro[2H-1-benzopyran-2,1'-cyclobutane] (10 mmol) (from example 18) in DMF, cyclopentyl bromide (12 mmol) and K$_2$CO$_3$ (12 mmol) was added and the reaction mixture was heated at 60° C. for 12 h. Solvent was then evaporated and the residue was dissolved in ethyl acetate. Organic layer was washed with water, brine and separated. It was then dried on anhydrous Na$_2$SO$_4$ and concentrated to afford the desired product as oil.

$^1$H NMR (CDCl$_3$): δ 1.54-2.02 (10H, m); 2.04-2.28 (4H, m); 2.87 (2H, s); 4.90 (1H, m); 6.50 (1H, d, J=2.7 Hz); 6.57 (1H, dd, J=2.4 & 8.7 Hz); 7.63 (1H, d, J=8.7 Hz).

Step II: 7-cyclopentyloxy-3,4-dihydro-4-hydroxy-imino-spiro[2H-1-benzopyran-2,1'-cyclobutane]

Step II: (±) 4-Amino-7-cyclopentyloxy-3,4-dihydro-spiro[2H-1-benzopyran-2,1'-cyclobutane]

$^1$H NMR (DMSO-d$_6$): δ 1.55-2.56 (1H, m); 4.47 (1H, m), 4.78 (1H, m); 6.33 (1H, d, J=2.7 Hz); 6.51 (1H, dd, J=8.7 Hz); 7.50 (1H, d, J=8.7 Hz); 8.73 (3H, b).

Step IV: (±) 1-(7-Cyclopentyloxy-3,4-dihydro-spiro[2H-1-benzopyran-2,1'-cyclobutane]-4-yl)-3-(iso-quinolin-5-yl)urea $^1$H NMR (DMSO-d$_6$): δ 51.50-1.93 (1H, m); 2.08-2.44 (5H, m); 4.77 (1H, m); 4.94 (1H, m); 6.32 (1H, s); 6.48 (1H, d, J=7.8 Hz); 6.96 (1H, d, J=6.9 Hz); 7.16 (1H, d, J=8.4 Hz); 7.62 (1H, t, J=7.8 Hz); 7.75 (1H, d, J=7.8 Hz); 7.92 (1H, d, J=5.1 Hz); 8.38 (1H, d, J=7.2 Hz); 8.55 (1H, d, J=5.7 Hz); 8.69 (1H, s); 9.28 (1H, s); IR (KBr) (cm$^{-1}$): 3318, 2955, 1632, 1563, 1498; MS (M$^+$+1): 445.2

Example 54

(±) 1-(7-Difluoromethoxy-3,4-dihydro-spiro[2H-1-benzopyran-2,1'-cyclobutane]-4-yl)-3-(isoquinolin-5-yl)urea. Hydrochloride Step I: 7-Difluoromethoxy-3,4-dihydro-4-oxo-spiro [2H-1-benzopyran-2,1'-cyclobutane]

To a solution of 3,4-Dihydro-7-hydroxy-4-oxo-spiro[2H-1-benzopyran-2,1'-cyclobutane] (from example 18) (10 mmol) in DMF (2.5 ml), K$_2$CO$_3$ was added and the reaction mixture was heated at 85° C. for 2 h. Chlorodifluoromethane gas was then bubbled in the reaction at the same temperature for 2 h. Reaction mixture was cooled to rt and quenched with cold water. Compound was then extracted in ethyl acetate. Organic layer was then separated, dried over anhydrous Na$_2$SO$_4$ and concentrated under vacuum. Crude compound thus obtained was purified by column chromatography to afford the desired product. $^1$H NMR (DMSO-d$_6$): δ 1.70-1.87 (2H, m); 2.02-2.30 (4H, m); 3.00 (2H, s); 7.13 (1H, d, J=9.3 Hz); 7.20 (1H, t, J=74.1 Hz); 7.40-8.45 (2H, m).

Step II: 7-difluoromethoxy-3,4-Dihydro-4-hydroxy-imino-spiro[2H-1-benzopyran-2,1'-cyclobutane]

Step III: (±) 4-Amino-7-difluoromethoxy-3,4-dihy-dro-spiro[2H-1-benzopyran-2,1'-cyclobutane]

$^1$H NMR (DMSO-d$_6$): δ 1.67-2.56 (8H, m); 4.57 (1H, m); 6.68 (1H, s); 6.83 (1H, d, J=8.1 Hz); 7.27 (1H, t, J=72 Hz); 7.66 (1H, d, J=8.4 Hz); 8.75 (3H, b).

Step IV: (±) 1-(7-Difluoromethoxy-3,4-dihydro-spiro [2H-1-benzopyran-2,1'-cyclobutane]-4-yl)-3-(iso-quinolin-5-yl)urea. hydrochloride $^1$H NMR (DMSO-d$_6$): δ 1.69-2.02 (3H, m); 2.10-2.48 (5H, m); 5.02 (1H, m); 6.62 (1H, d, J=2.4 Hz); 6.74 (1H, dd, J=2.1 & 8.4 Hz); 7.23 (1H, t, J=74.1 Hz); 7.35 (1H, d, J=7.8 Hz); 7.55-7.75 (1H, m); 7.93 (1H, t, J=7.8 Hz); 8.11 (1H, d, J=7.8 Hz); 8.68-8.75 (3H, m); 9.55-9.75 (1H, m); 9.81 (1H, s); IR (KBr) (cm$^{-1}$): 3399, 3041, 2990, 1698, 1544, 1121; MS (M$^+$+1):

Example 55

(±) 1-(3,4-Dihydro-6-methylaminosulfonyl-spiro [2H-1-benzopyran-2,1'-cyclobutane]-4-yl)-3-(iso-quinolin-5-yl)urea Step I: 3,4-Dihydro-6-methylaminosulfonyl-4-oxo-spiro[2H-1-benzopyran-2,1'-cyclobutane]

A mixture of 3,4-Dihydro-4-oxo-spiro[2H-1-benzopyran-2,1'-cyclobutane] (from example 3) (10 mmol) and chlorosulfonic acid was stirred at room temperature for 2 h. It was then quenched with ice followed by water and the chlorosulfonyl derivative was extracted in chloroform. Organic layer was separated, dried over anhydrous Na$_2$SO$_4$ and concentrated under vacuum. The residue was again dissolved in chloroform and treated with aq. solution of methyl amine at −50° C. and stirred for 2 h. The reaction mixture was then diluted with chloroform and washed with water. Organic layer was separated, dried over anhydrous $Na_2SO_4$ and concentrated under vacuum. The crude product was then purified by column chromatography to afford pure 3,4-Dihydro-6-methylaminosulfonyl-4-oxo-spiro[2H-1-benzopyran-2,1'-cyclobutane].

$^1$H NMR (DMSO-$d_6$): δ 1.72-1.92 (2H, m); 2.10-2.34 (4H, m); 2.40 (3H, d, J=5.1 Hz); 3.09 (2H, s); 7.28 (1H, d, J=8.7 Hz); 7.52 (1H, m); 7.91 (1H, dd, J=2.4 & 9.0 Hz); 8.09 (1H, d, J=2.1 Hz).

Step II: 3,4-Dihydro-4-hydroxyimino-6-methylaminosulfonyl-spiro[2H-1-benzopyran-2,1'-cyclobutane]

$^1$H NMR (DMSO-$d_6$): δ 1.71-1.85 (2H, m); 2.00-2.06 (2H, m); 2.12-2.29 (2H, m); 2.38 (3H, d); 3.00 (2H, s); 4.57 (1H, m); 7.08 (1H, d, J=8.7 Hz); 7.40 (1H, m); 7.62 (1H, dd, J=8.4 Hz); 8.13 (1H, d, J=2.4 Hz); 11.59 (1H, s).

Step III: (±) 4-Amino-3,4-dihydro-6-methylaminosulfonyl-spiro[2H-1-benzopyran-2,1'-cyclobutane]

Step IV: (±) 1-(3,4-Dihydro-6-methylaminosulfonyl-spiro-[2H-1-benzopyran-2,1'-cyclobutane]-4-yl)-3-(isoquinolin-5-yl)urea $^1$H NMR (DMSO-$d_6$): δ 1.69-2.02 (3H, m); 2.10-2.30 (3H, m); 2.34-2.48 (5H, m); 5.07 (1H, m); 7.00 (1H, d, J=8.7 Hz); 7.14 (1H, d, J=8.4 Hz); 7.35 (1H, q, J=4.8 Hz); 7.57 (1H, d, J=8.4 Hz); 7.64 (1H, t, J=7.5 Hz); 7.75 (1H, s); 7.79 (1H, d, J=7.8 Hz); 7.93 (1H, d, J=5.7 Hz); 8.32 (1H, d, J=7.5 Hz); 8.56 (1H, d, J=5.7 Hz); 8.83 (1H, s); 9.30 (1H, s).

Example 56

(±) 1-(7-Difluoromethoxy-3,4-dihydro-spiro[2H-1-benzopyran-2,1'-cyclobutane]-4-yl)-3-(3-methylisoquinolin-5-yl)urea $^1$H NMR (DMSO-$d_6$): δ 1.70-1.97 (3H, m); 2.10-2.46 (5H, m); 2.65 (3H, s); 4.99 (1H, m); 6.64 (1H, d, J=2.1 Hz); 6.76 (1H, dd, J=2.1 & 8.4 Hz); 7.02 (1H, d, J=8.1 Hz); 7.23 (1H, t, J=74.1 Hz); 7.34 (1H, d, J=8.4 Hz); 7.50 (1H, d, J=9.0 Hz); 7.55 (1H, d, J=8.1 Hz); 7.72 (1H, d, J=8.1 Hz); 7.75 (1H, s); 8.32 (1H, d, J=7.8 Hz); 8.65 (1H, s); 9.19 (1H, s).

Example 57

(±) 1-(7-Chloro-3,4-dihydro-spiro[2H-1-benzopyran-2,1'-cyclobutane]-4-yl)-3-(3-methylisoquinolin-5-yl)urea $^1$H NMR (DMSO-$d_6$): δ 1.69-1.96 (3H, m); 2.11-2.48 (5H, m); 2.66 (3H, s); 4.99 (1H, m); 6.85 (1H, d, J=9.0 Hz); 7.08 (1H, d, J=8.4 Hz); 7.21 (1H, dd, J=2.7 & 8.7 Hz); 7.30 (1H, d, J=2.4 Hz); 7.54 (1H, t, J=7.8 Hz); 7.73 (3H, m); 8.28 (1H, d, J=7.8 Hz); 8.68 (1H, s); 9.20 (1H, s).

Example 58

(±) 1-(8-Cyano-3,4-dihydro-spiro[2H-1-benzopyran-2,1'-cyclobutane]-4-yl)-3-(isoquinolin-5-yl)urea $^1$H NMR (DMSO-$d_6$): δ1.76-2.08 (3H, m); 2.18-2.48 (5H, m); 5.05 (1H, m); 7.08 (1H, t, J=7.5 Hz); 7.11 (1H, d, J=8.4 Hz); 7.64 (2H, m); 7.78 (1H, d, J=7.8 Hz); 7.94 (1H, d, J=6.3 Hz); 8.34 (1H, d, J=8.1 Hz); 8.56 (1H, d, J=6.3 Hz); 8.81 (1H, s); 9.29 (1H, s).

Example 59

(+) 1-(6,8-Difluoro-3,4-Dihydro-spiro[2H-1-benzopyran-2,1'-cyclobutane]-4-yl)-3-isoquinolin-5-yl)urea This compound was prepared from (−) 4-Amino-3,4-dihydro-6,8-difluorospiro[2H-1-benzopyran-2,1'-cyclobutane] as described in step IV of example 1.

[α]$^{25}$=+61.18 (c=1, methanol)

$^1$H NMR (DMSO-$d_6$): δ 1.74-2.00 (3H, m); 2.16-2.37 (5H, m); 5.02 (1H, m); 6.96 (1H, d, J=8.7 Hz); 7.11 (1H, d, J=7.8 Hz); 7.20 (1H, t, J=9 Hz); 7.63 (1H, t, J=7.2 & 8.1 Hz); 7.78 (1H, d, J=8.1 Hz); 7.94 (1H, d, J=5.7 Hz); 8.33 (1H, d, J=7.5 Hz); 8.51 (1H, d, J=6.3 Hz); 8.79 (1H, s); 9.29 (1H, s); IR (KBr) (cm$^{-1}$): 3313, 2395, 1633, 1483, 1226.

Example 60

(−) 1-(6,8-Difluoro-3,4-Dihydro-spiro[2H-1-benzopyran-2,1'-cyclobutane]-4-yl)-3-(isoquinolin-5-yl)urea This compound was prepared from (+) 4-Amino-3,4-dihydro-6,8-difluorospiro[2H-1-benzopyran-2,1'-cyclobutane] as described in step 1V of example 1.

[α]$^{21}$=−71.37 (c=1, methanol)

$^1$H NMR (DMSO-$d_6$): δ 1.74-2.03 (3H, m); 2.16-2.37 (5H, m); 5.01 (1H, m); 6.97 (1H, d, J=8.7 Hz); 7.12 (1H, d, J=7.8 Hz); 7.21 (1H, t, J=9 Hz); 7.63 (1H, t, J=7.2 & 8.1 Hz); 7.78 (1H, d, J=8.1 Hz); 7.93 (1H, d, J=5.7 Hz); 8.33 (1H, d, J=7.5 Hz); 8.56 (1H, d, J=6.3 Hz); 8.79 (1H, s); 9.29 (1H, s).

Example 61

(±) 1-(3,4-Dihydro-8-hydroxy-spiro[2H-1-benzopyran-2,1'-cyclobutane]-4-yl)-3-(isoquinolin-5-yl)urea Step I: 3,4-Dihydro-8-hydroxy-4-oxo-spiro[2H-1-benzopyran-2,1'-cyclobutane]

$^1$H NMR (CDCl$_3$): δ 1.60-2.40 (8H, m); 5.62 (1H, m); 6.91 (1H, t, J=7.5 Hz); 7.13 (1H, d, J=7.8 Hz); 7.39 (1H, d, J=7.8 Hz); MS (M$^+$−1): 203.34

Step II: 3,4-Dihydro-4-hydroxyimino-8-hydroxy-spiro[2H-1-benzopyran-2,1'-cyclobutane]

$^1$H NMR (CDCl$_3$): δ 1.60-2.40 (8H, m); 3.09 (2H, brs); 6.83 (1H, t, J=8.1 Hz); 6.93 (1H, d, J=6.6 Hz); 7.22-7.38 (1H, m); MS (M$^+$+1): 220.26

Step II: (±) 4-Amino-3,4-dihydro-8-hydroxy-spiro[2H-1-benzopyran-2,1'-cyclobutane]hydrochloride $^1$H NMR (DMSO-$d_6$): δ 1.60-2.40 (8H, m); 4.32 (2H, brs); 6.64-6.80 (2H, m); 7.06 (1H, d, J=6.3 Hz); 9.04 (1H, m); MS (M$^+$+1): 205.69

Step IV: (±) 1-(3,4-Dihydro-8-hydroxy-spiro[2H-1-benzopyran-2,1'-cyclobutane]-4-yl)-3-(isoquinolin-5-yl)urea $^1$H NMR (DMSO-d$_6$): δ 1.70-1.94 (3H, m); 2.10-2.48 (5H, m); 4.95-5.05 (1H, m); 6.66-6.80 (3H, m); 7.00 (1H, d, J=8.1 Hz); 7.60-7.80 (3H, m); 7.94 (1H, d, J=6.0 Hz); 8.39 (1H, d, J=7.5 Hz); 8.56 (1H, d, J=5.7 Hz); 8.72 (1H, s); 8.84 (1H, s); 9.29 (1H, s). IR (KBr) (cm$^{-1}$): 3317, 1627, 1565, 1470, 1224; MS (M$^+$−1): 374.21; M.P. 246-247° C.

Example 62

(±) 1-(3,4-Dihydro-8-difluoromethoxy-spiro[2H-1-benzopyran-2,1'-cyclobutane]-4-yl)-3-(isoquinolin-5-yl)urea

Step I: 3,4-Dihydro-8-difluoromethoxy-4-oxo-spiro[2H-1-benzopyran-2,1'-cyclobutane]

This compound was prepared by difluoromethoxylation of 3,4-Dihydro-8-hydroxy-4-oxo-spiro[2H-1-benzopyran-2,1'-cyclobutane] using chlorodifluoromethane gas in the presence: of potassium carbonate in DMF at 30-80° C.

$^1$H NMR (CDCl$_3$): δ 1.66-2.04 (2H, m); 2.14-2.26 (2H, m); 2.32-2.44 (2H, m); 2.94 (2H, s); 6.22 (1H, t, J=74.4 Hz); 6.97 (1H, t, J=8.1 Hz); 7.38 (1H, d, J=7.2 Hz); 7.75 (1H, dd J=1.5 Hz & J=7.5 Hz); MS (M$^+$−1): 253.36

Step II: 3,4-Dihydro-4-hydroxyimino-8-hydroxy-spiro[2H-1-benzopyran-2,1'-cyclobutane]

$^1$H NMR (CDCl$_3$): δ 1.70-2.38 (8H, m); 3.07 (2H, brs); 6.60 (1H, t, J=74.7 Hz); 6.89 (1H, t, J=8.1 Hz); 7.16 (1H, d, J=8.4 Hz); 7.69 (1H, d, J=6.9 Hz); MS (M$^+$−1): 268.23

Step III: (±) 4-Amino-3,4-dihydro-8-difluoromethoxy-spiro[2H-1-benzopyran-2,1'-cyclobutane] hydrochloride $^1$H NMR (DMSO-d$_6$): δ 1.60-2.64 (8H, m); 4.52-4.66 (1H, m); 6.85 (1H, d, J=7.8 Hz); 6.98 (1H, d, J=6.9 Hz); 7.25 (1H, d, J=7.5 Hz); 7.64 (1H, d, J=6.9 Hz); 8.85 (2H, m). MS (M$^+$+1): 255.72

Step IV: (±) 1-(3,4-Dihydro-8-difluoromethoxy-spiro[2H-1-benzopyran-2,1'-cyclobutane]-4-yl)-3-(isoquinolin-5-yl)urea $^1$H NMR (DMSO-d$_6$): δ 1.70-2.08 (3H, m); 2.10-2.57 (5H, m); 5.03 (1H, m); 6.82 (1H, d, J=7.8 Hz); 6.88-6.98 (1H, m); 7.02-7.10 (1H, m); 7.18 (1H, t, J=7.2 Hz); 7.31 (1H, d, J=7.2 Hz); 7.64 (1H, t, J=7.8 Hz); 7.77 (1H, d, J=7.8 Hz); 7.94 (1H, d, J=6.0 Hz); 8.39 (1H, d, J=7.5 Hz); 8.56 (1H, d, J=5.7 Hz); 8.73 (1H, s); 9.29 (1H, s); IR (KBr) (cm$^{-1}$): 3323, 1630, 1563, 1235, 754; MS (M$^+$+1): 426.25

Example 63

(±) 1-(6-Chloro-3,4-dihydro-spiro[2H-1-benzopyran-2,1'-cyclobutane]-4-yl)-3-(isoquinolin-5-yl)urea

Step I: 6-Chloro-3,4-Dihydro-4-oxo-spiro[2H-1-benzopyran-2,1'-cyclobutane]

This compound was prepared in the same manner from 5'-chloro-2'-hydroxyacetophenone as in step 1 of example 3.

$^1$H NMR (CDCl$_3$): δ 1.64-1.80 (1H, m); 1.86-2.02 (1H, m); 2.10-2.22 (2H, m); 2.26-2.40 (2H, m); 2.90 (2H, s); 6.94 (1H, d, J=9.0 Hz); 7.41 (1H, dd, J=3.0 & 8.7 Hz); 7.81 (1H, d, J=2.7 Hz).

Step II: 6-Chloro-3,4-dihydro-4-hydroxy-spiro[2H-1-benzopyran-2,1'-cyclobutane]

Sodium borohydride (40 mmol) was added to a solution of 6-Chloro-3,4-dihydro-4-oxo-spiro[2H-1-benzopyran-2,1'-cyclobutane] (10 mmol) in methanol (10 ml). at about 0° C. and the reaction mixture was stirred at room temperature for about 2 h and compound was extracted in ethyl acetate. Organic layer was washed with water, brine and separated. It was then dried on anhydrous sodium sulfate and concentrated to afford the desired product as a white solid.

Step III: 4-Acetamido-6-chloro-3,4-dihydro-spiro[2H-1-benzopyran-2,1'-cyclobutane]

A solution of 6-Chloro-3,4-dihydro-4-hydroxy-spiro[2H-1-benzopyran-2,1'-cyclobutane] (10 mmol) in acetonitrile (30-50 ml) was added to a solution of concentrated sulfuric acid (30 mmol) in acetonitrile (10 ml), at 0 to −10° C. The reaction mixture was stirred for about 2 hrs and was allowed to warm up, to room temperature. It was then added on ice. The corresponding acetamido derivative was separated out as a white solid which was filtered, washed with water and dried.

Step IV: (±) 4-Amino-6-chloro-3,4-dihydro-spiro[2H-1-benzopyran-2,1'-cyclobutane]

4-Acetamido-6-chloro-3,4-dihydro-spiro[2H-1-benzopyran-2,1'-cyclobutane] (1.0 gm) was hydrolyzed using refluxing concentrated hydrochloric acid (10 ml). The reaction mixture was cooled, diluted with ethyl acetate and basified with 40% sodium hydroxide. The organic layer was separated, washed with water, dried over anhydrous sodium sulfate and concentrated to get the product as a oil which was converted to its hydrochloride salt.

$^1$H NMR (DMSO-d$_6$): δ 1.63-2.56 (8H, m); 4.58 (1H, m); 6.88 (1H, d, J=8.7 Hz); 7.30 (1H, dd, J=8.7 Hz); 7.71 (1H, d, J=2.1 Hz); 8.69 (3H, b).

To a solution of (±) 4-Amino-6-chloro-3,4-dihydro-spiro [2H-1-benzopyran-2,1'-cyclobutane] (200 mg) in isopropyl alcohol (10 ml) was added a solution of R (−) mandelic acid (131 mg) in isopropyl alcohol (5 ml) at room temperature and the clear solution was stirred for 12-24 h. The precipitated salt was filtered, dried and reneutralized with 2N sodium hydroxide to obtain (+) 4-Amino-6-chloro-3,4-dihydro-spiro[2H-1-benzopyran-2,1'-cyclobutane] (60 mg) with >98% ee.

Step V: (±) 1-(6-Chloro-3,4-dihydro-spiro[2H-1-benzopyran-2,1'-cyclobutane]-4-yl)-3-(isoquinolin-5-yl)urea This compound was prepared by treatment of (±) 4-Amino-6-chloro-3,4-dihydro-spiro[2H-1-benzopyran-2,1'-cyclobutane] with phenyl N-(isoquinolin-5-yl)carbamate as described in step IV of example 1.

$^1$H NMR (DMSO-d$_6$): δ 1.70-1.97 (3H, m); 2.15-2.54 (5H, m); 5.10 (1H, m); 6.86 (1H, d, J=8.4 Hz); 7.10 (1H, d, J=8.1 Hz); 7.23 (1H, dd, J=2.4 & 8.7 Hz); 7.31 (1H, d, J=2.4 Hz); 7.65 (1H, t, J=8.1 Hz); 7.79 (1H, d, J=8.1 Hz); 7.95 (1H, d, J=6.3 Hz); 8.35 (1H, d, J=7.2 Hz); 8.57 (1H, d, J=5.7 Hz); 8.78 (1H, s); 9.30 (1H, s); IR (KBr) (cm$^{-1}$): 3315, 1633, 1567, 1473, 1265; MS (M$^+$+1): 394.2

Example 64

(−) 1-(6-Chloro-3,4-dihydro-spiro[2H-1-benzopyran-2,1'-cyclobutane]-4-yl)-3-(isoquinolin-5-yl)urea This compound was prepared by treatment of (−) 4-Amino-6-chloro-3,4-dihydro-spiro[2H-1-benzopyran-2,1'-cyclobutane] with phenyl N-(isoquinolin-5-yl)carbamate as described in step IV of example 1.

$^1$H NMR (DMSO-d$_6$): δ 1.70-1.97 (3H, m); 2.15-2.54 (5H, m); 5.01 (1H, m); 6.86 (1H, d, J=8.7 Hz); 7.10 (1H, d, J=8.7 Hz); 7.23 (1H, dd, J=2.4 & 8.7 Hz); 7.30 (1H, d, J=2.4 Hz); 7.65 (1H, t, J=8.1 Hz); 7.79 (1H, d, J=8.1 Hz); 7.95 (1H, d, J=6.3 Hz); 8.35 (1H, d, J=7.2 Hz); 8.57 (1H, d, J=5.7 Hz); 8.78 (1H, s); 9.29 (1H, s); IR (KBr) (cm$^{-1}$): 3367, 2934, 1642, 1551, 1474, 1263, 1232; MS (M$^+$+1): 394.2

Examples 65 to 75 were synthesized by following the procedure as described in Example 63

Example 65

(±) 1-(6-Bromo-3,4-dihydro-spiro[2H-1-benzopyran-2,1'-cyclobutane]-4-yl)-3-(isoquinolin-5-yl)urea Step I: 6-Bromo-3,4-Dihydro-4-oxo-spiro[2H-1-benzopyran-2,1'-cyclobutane]

$^1$H NMR (CDCl$_3$): δ 1.67-1.79 (1H, m); 1.88-1.99 (1H, m); 2.10-2.21 (2H, m); 2.27-2.38 (2H, m); 2.89 (2H, s); 6.89 (1H, d, J=8.4 Hz); 7.55 (1H, dd, J=2.4 & 8.7 Hz); 7.96 (1H, d, J=2.4 Hz).

Step II: 6-Bromo-3,4-dihydro-4-hydroxy-spiro[2H-1-benzopyran-2,1'-cyclobutane]

Step III: 4-Acetamido-6-bromo-3,4-dihydro-spiro[2H-1-benzopyran-2,1'-cyclobutane]

$^1$H NMR (DMSO-d$_6$): δ 1.65-1.83 (3H, m); 1.93 (3H, s); 2.05-2.16 (3H, m); 2.25-2.52 (2H, m); 5.05 (1H, m); 6.75 (1H, d, J=8.7 Hz); 7.18 (1H, d, J=2.1 Hz); 7.30 (1H, dd, J=8.4 Hz); 8.37 (1H, d, J=8.4 Hz).

Step IV: (±) 4-Amino-6-bromo-3,4-dihydro-spiro[2H-1-benzopyran-2,1'-cyclobutane]

$^1$H NMR (DMSO-d$_6$): δ 1.65-2.80 (8H, m); 4.60 (1H, m); 6.85 (1H, d, J=8.1 Hz); 7.40 (1H, dd, J=8.1 Hz); 7.83 (1H, brs); 8.73 (3H, b).

Step V: (±) 1-(6-Bromo-3,4-dihydro-spiro[2H-1-benzopyran-2,1'-cyclobutane]-4-yl)-3-(isoquinolin-5-yl)urea $^1$H NMR (DMSO-d$_6$): δ 1.69-1.96 (3H, m); 2.08-2.46 (5H, m); 5.00 (1H, m); 6.80 (1H, d, J=9.0 Hz); 7.09 (1H, d, J=8.1 Hz); 7.33 (1H, dd, J=2.1 & 8.4 Hz); 7.42 (1H, s); 7.64 (1H, t, J=8.1 Hz); 7.79 (1H, d, J=8.1 Hz); 7.94 (1H, d, J=5.7 Hz); 8.34 (1H, d, J=7.2 Hz); 8.56 (1H, d, J=5.7 Hz); 8.77 (1H, s); 9.29 (1H, s); IR (KBr) (cm$^{-1}$): 3307, 2935, 1632, 1562, 1472, 1234.

Example 66

(±) 1-(6,8-Dichloro-3,4-dihydro-spiro[2H-1-benzopyran-2,1'-cyclobutane]-4-yl)-3-(isoquinolin-5-yl)urea Step I: 6,8-Dichloro-3,4-Dihydro-4-oxo-spiro[2H-1-benzopyran-2,1'-cyclobutane]

Step II: 6,8-Dichloro-3,4-dihydro-4-hydroxy-spiro[2H-1-benzopyran-2,1'-cyclobutane]

Step III: 4-Acetamido-6,8-dichloro-3,4-dihydro-spiro[2H-1-benzopyran-2,1'-cyclobutane]

$^1$H NMR (DMSO-d$_6$): δ 1.77-2.36 (1H, m); 5.05 (1H, m); 7.06 (1H, s); 7.49 (1H, s); 8.39 (1H, d, J=8.4 Hz).

Step IV: (±) 4-Amino-6,8-dichloro-3,4-dihydro-spiro[2H-1-benzopyran-2,1'-cyclobutane]

$^1$H NMR (DMSO-d$_6$): δ 1.62-2.66 (8H, m); 4.62 (1H, m); 7.58 (1H, s); 7.90 (1H, s); 9.16 (3H, b).

Step V: (±) 1-(6,8-Dichloro-3,4-dihydro-spiro[2H-1-benzopyran-2,1'-cyclobutane]-4-yl)-3-(isoquinolin-5-yl)urea $^1$H NMR (DMSO-d$_6$): , 1.72-2.46 (8H, m); 5.08 (1H, m); 7.18 (1H, d, J=8.7 Hz); 7.35 (1H, d, J=2.7 Hz); 7.57 (1H, d, J=2.4 Hz); 7.71 (1H, t, J=7.8 Hz); 7.86 (1H, d, J=7.8 Hz); 8.00 (1H, d, J=6.0 Hz); 8.38 (1H, d, J=7.8 Hz); 8.63 (1H, d, J=5.7 Hz); 8.89 (1H, s); 9.36 (1H, s).

Example 67

(±) 1-(6-Bromo-3,4-dihydro-7-methylspiro[2H-1-benzopyran-2,1'-cyclobutane]-4-yl)-3-(isoquinolin-5-yl)urea Step II: 6-Bromo-3,4-dihydro-7-methyl-4-oxo-spiro[2H-1-benzopyran-2,1'-cyclobutane]

$^1$H NMR (CDCl$_3$): δ 1.64-1.79 (1H, m); 1.84-1.99 (1H, m); 2.10-2.22 (2H, m); 2.24-2.36 (2H, m); 2.37 (3H, s); 2.87 (2H, s); 6.88 (1H, s); 7.98 (1H, s).

Step III: 6-Bromo-3,4-dihydro-4-hydroxy-7-methylspiro[2H-1-benzopyran-2,1'-cyclobutane]

Step III: 4-Acetamido-6-bromo-3,4-dihydro-7-methyl-spiro[2H-1-benzopyran-2,1'-cyclobutane]

Step IV: (±) 4-Amino-6-bromo-3,4-dihydro-7-methyl-spiro[2H-1-benzopyran-2,1'-cyclobutane]

$^1$H NMR (DMSO-d$_6$): δ 1.67-2.56 (1H, m); 4.55 (1H, m); 6.88 (1H, s); 7.83 (1H, d); 8.73 (3H, b).

Step V: (±) 1-(6-Bromo-3,4-dihydro-7-methyl-spiro[2H-1-benzopyran-2,1'-cyclobutane]-4-yl)-3-(isoquinolin-5-yl)urea $^1$H NMR (DMSO-d$_6$): δ 1.69-2.00 (3H, m); 2.10-2.50 (8H, m); 4.97 (1H, m); 6.85 (1H, s); 7.05 (1H, d, J=8.1 Hz); 7.42 (1H, s); 7.63 (1H, t, J=7.8 Hz); 7.78 (1H, d, J=8.1 Hz); 7.93 (1H, d, J=5.7 Hz); 8.33 (1H, d, J=7.8 Hz); 8.56 (1H, d, J=5 Hz); 8.76 (1H, s); 9.29 (1H, s).

Example 68

(±) 1-(6,7-Dichloro-3,4-dihydro-spiro[2H-1-benzopyran-2,1'-cyclobutane]-4-yl)-3-(isoquinolin-5-yl) urea

Step I: 6,7-Dichloro-3,4-Dihydro-4-oxo-spiro[2H-1-benzopyran-2,1'-cyclobutane]

$^1$H NMR (CDCl$_3$): δ1.64-1.80 (1H, m); 1.88-2.03 (1H, m); 2.10-2.22 (2H, m); 2.26-2.40 (2H, m); 2.89 (2H, s); 7.14 (1H, s); 7.90 (1H, s).

Step II: 6,7-Dichloro-3,4-dihydro-4-hydroxy-spiro[2H-1-benzopyran-2,1'-cyclobutane]

Step III: 4-Acetamido-6,7-Dichloro-3,4-dihydro-spiro[2H-1-benzopyran-2,1'-cyclobutane]

Step IV: (±) 4-Amino-6,7-Dichloro-3,4-dihydro-spiro[2H-1-benzopyran-2,1'-cyclobutane]

$^1$H NMR (DMSO-d$_6$): δ 1.67-2.36 (8H, m); 4.60 (1H, m); 7.2 (1H, s); 7.9 (1H, s); 8.73 (3H, b).

Step V: (#) 1-(6,7-Dichloro-3,4-dihydro-spiro[2H-1-benzopyran-2,1'-cyclobutane]-4-yl)-3-(isoquinolin-5-yl)urea $^1$H NMR (DMSO-d$_6$): δ 1.69-2.00 (3H, m); 2.10-2.50 (5H, m); 4.98 (1H, m); 7.11 (1H, d, J=8.4 Hz); 7.13 (1H, s); 7.48 (1H, s); 7.64 (1H, t, J=7.8 Hz); 7.79 (1H, d, J=8.1 Hz); 7.94 (1H, d, J=6.0 Hz); 8.33 (1H, d, J=7.2 Hz); 8.57 (1H, d, J=6.3 Hz); 8.81 (1H, s); 9.30 (1H, s).

Example 69

(±) 1-(6-Chloro-3,4-dihydro-7-methyl-spiro[2H-1-benzopyran-2,1'-cyclobutane]-4-yl)-3-(isoquinolin-5-yl)urea

Step I: 6-Chloro-3,4-dihydro-7-methyl-4-oxo-spiro[2H-1-benzopyran-2,1'-cyclobutane]

$^1$H NMR (CDCl$_3$): δ 1.66-1.79 (1H, m); 1.84-1.99 (1H, m); 2.10-2.21 (2H, m); 2.24-2.40 (2H, m); 2.37 (3H, s); 2.87 (2H, s); 6.87 (1H, s); 7.80 (1H, s).

Step II: 6-Chloro-3,4-dihydro-4-hydroxy-7-methyl-spiro[2H-1-benzopyran-2,1'-cyclobutane]

Step III: 4-Acetamido-6-chloro-3,4-dihydro-7-methyl-spiro[2H-1-benzopyran-2,1'-cyclobutane]

Step IV: (±) 4-Amino-6-chloro-3,4-dihydro-7-methyl-spiro[2H-1-benzopyran-2,1'-cyclobutane]

$^1$H NMR (DMSO-d$_6$): δ 1.57-2.56 (1H, m); 4.48 (1H, m); 6.89 (1H, s); 7.63 (1H, s); 8.58 (3H, b).

Step V: (±) 1-(6-Chloro-3,4-dihydro-7-methylspiro[2H-1-benzopyran-2,1'-cyclobutane]-4-yl)-3-(isoquinolin-5-yl)urea $^1$H NMR (DMSO-d$_6$): δ 1.72-1.93 (3H, m); 2.09-2.46 (5H, m); 2.25 (3H, s); 4.99 (1H, m); 6.84 (1H, s); 7.05 (1H, d, J=8.1 Hz); 7.27 (1H, s); 7.64 (1H, t, J=7.8 Hz); 7.78 (1H, d, J=7.8 Hz); 7.94 (1H, d, J=5.7 Hz); 8.35 (1H, d, J=7.2 Hz); 8.56 (1H, d, J=6.0 Hz); 8.76 (1H, s); 9.30 (1H, s); IR (KBr) (cm$^{-1}$); MS (M+1):

Example 70

(±) 1-(6-Chloro-3,4-dihydro-spiro[2H-1-benzopyran-2,1'-cyclobutane]-4-yl)-3-(8-chloroisoquinolin-5-yl) urea $^1$H NMR (DMSO-d$_6$): , 1.70-1.99 (3H, m); 2.096-2.46 (5H, m); 4.98 (1H, m); 6.85 (1H, d, J=8.4 Hz); 7.14 (1H, d, J=8.1 Hz); 7.22 (1H, d, J=8.4 Hz); 7.29 (1H, s); 7.79 (1H, d, J=8.4 Hz); 8.02 (1H, d, J=5.7 Hz); 8.36 (1H, d, J=8.4 Hz); 8.71 (1H, d, J=6.0 Hz); 8.89 (1H, s); 9.53 (1H, s); IR (KBr) (cm$^{-1}$): 3304, 3069, 2983, 2938, 1634, 1567, 1475, 1372, 1312, 1265, 1233, 830; MS (M$^+$+1): 428.3

Example 71

(±) 1-(6-Fluoro-3,4-dihydro-spiro[2H-1-benzopyran-2,1'-cyclobutane]-4-yl)-3-(8-chloroisoquinolin-5-yl) urea $^1$H NMR (DMSO-d$_6$): δ 1.65-1.99 (3H, m); 2.10-2.46 (5H, m); 4.98 (1H, m); 6.84 (1H, m); 7.14 (3H, m); 7.89 (1H, d); 8.02 (1H, d); 8.33 (1H, d); 8.70 (1H, d); 8.87 (1H, s); 9.53 (1H, s); IR (KBr) (cm$^{-1}$): 3330, 2990, 2935, 1643, 1567, 1486, 1370, 1311, 1256, 1211, 827, 814; MS (M$^+$+1): 412.1

Example 72

(±) 1-(3,4-Dihydro-6-fluoro-spiro[2H-1-benzopyran-2,1'-cyclobutane]-4-yl)-3-(3-methylisoquinolin-5-yl) urea $^1$H NMR (DMSO-d$_6$): δ 1.69-1.94 (3H, m); 2.10-2.48 (5H, m); 2.68 (3H, s); 5.03 (1H, m); 6.83 (1H, dd, J=4.8 & 8.7 Hz); 6.99-7.12 (3H, m); 7.54 (1H, t, J=8.1 Hz); 7.2-7.75 (2H, m); 8.27 (1H, d, J=7.8 Hz); 8.68 (1H, s); 9.19 (1H, s).
IR (KBr) (cm$^{-1}$); MS (M$^+$+1): 392.2

Example 73

(±) 1-(6-Chloro-3,4-dihydro-spiro[2H-1-benzopyran-2,1'-cyclobutane]-4-yl)-3-(3-methylisoquinolin-5-yl) urea $^1$H NMR (DMSO-d$_6$): δ 1.69-1.95 (3H, m); 2.13-2.46 (5H, m); 2.66 (3H, s); 4.99 (1H, m); 6.85 (1H, d, J=8.7 Hz); 7.08 (1H, d, J=8.4 Hz); 7.21 (1H, dd, J=2.4 & 8.7 Hz); 7.30 (1H, d, J=2.4 Hz); 7.54 (1H, t, J=7.5 Hz); 7.73 (2H, m); 8.29 (1H, d, J=7.5 Hz); 8.68 (1H, s); 9.19 (1H, s); IR (KBr) (cm$^{-1}$): 3305, 1634, 1563, 1474, 1234; MS (M$^+$+1): 408.2

Example 74

(±) 1-(6-Chloro-3,4-dihydro-spiro[2H-1-benzopyran-2,1'-cyclobutane]-4-yl-3-(1-methylisoquinolin-5-yl) urea $^1$H NMR (DMSO-d$_6$): δ 1.72-1.95 (3H, m); 2.13-2.46 (5H, m); 2.89 (3H, s); 4.99 (1H, m); 6.85 (1H, d, J=9.0 Hz); 7.09 (1H, d, J=8.4 Hz); 7.21 (1H, dd, J=2.4 & 9.0 Hz); 7.29 (1H, d, J=2.4 Hz); 7.62 (1H, t, J=8.1 Hz); 7.79 (1H, d, J=6.0 Hz); 7.87 (1H, d, J=8.7 Hz); 8.31 (1H, d, J=7.8 Hz); 8.39 (1H, d, J=6.6 Hz); 8.72 (1H, s).

IR (KBr) (cm$^{-1}$): 3427, 3306, 1633, 1546, 1473, 1264, 1236; MS (M$^+$+1): 408.2

Example 75

(±) 1-(3,4-Dihydro-6-fluoro-spiro[2H-1-benzopyran-2,1'-cyclobutane]-4-yl)-3-(1-methylisoquinolin-5-yl)urea $^1$H NMR (DMSO-d$_6$): , 1.72-1.94 (3H, m); 2.10-2.48 (5H, m); 2.88 (3H, s); 5.00 (1H, m); 6.83 (1H, dd, J=4.8 & 7.8 Hz); 7.00-7.12 (3H, m); 7.61 (1H, t, J=7.5 Hz); 7.81 (1H, d, J=5.7 Hz); 7.86 (1H, d, J=8.1 Hz); 8.32 (1H, d, J=7.8 Hz); 8.38 (1H, d, J=5.7 Hz); 8.73 (1H, s); IR (KBr) (cm$^{-1}$); MS (M$^+$+1): 392.2

Example 76

(−) 1-(7-Chloro-3,4-dihydro-spiro[2H-1-benzopyran-2,1'-cyclobutane]-4-yl)-3-(isoquinolin-5-yl)urea Step I: 7-Chloro-3,4-Dihydro-4-oxo-spiro[2H-1-benzopyran-2,1'-cyclobutane]

$^1$H NMR (CDCl$_3$): δ 1.59-1.76 (1H, m); 1.86-1.99 (1H, m); 2.13-2.21 (2H, m); 2.23-2.40 (2H, m); 2.89 (2H, s); 6.95-7.01 (2H, m); 7.79 (1H, d, J=8.4 Hz).

Step II: 7-Chloro-3,4-dihydro-4-hydroxy-spiro[2H-1-benzopyran-2,1'-cyclobutane]

This compound was prepared in the same manner from 7-Chloro-3,4-dihydro-4-oxo-spiro[2H-1-benzopyran-2,1'-cyclobutane] as in step II of example 8.

Step III: 4-Acetamido-7-chloro-3,4-dihydro-spiro[2H-1-benzopyran-2,1'-cyclobutane]

This compound was prepared in the same manner from 7-Chloro-3,4-dihydro-4-hydroxy-spiro[2H-1-benzopyran-2,1'-cyclobutane] as in step III of example 6.
$^1$H NMR (CDCl$_3$): δ 1.67-2.45 (1H, m); 5.25 (1H, m); 5.63 (1H, m); 6.84 (2H, m); 7.10 (1H, d, J=8.4 Hz).

Step IV: (±) 4-Amino-7-chloro-3,4-dihydro-spiro[2H-1-benzopyran-2,1'-cyclobutane]

This compound was prepared in the same manner from 4-Acetamido-7-chloro-3,4-dihydro-spiro[2H-1-benzopyran-2,1'-cyclobutane] as in step 1V of example 8. Isolated as hydrochloride salt.
$^1$H NMR (DMSO-d$_6$): δ 1.60-2.62 (8H, m); 4.51 (1H, m); 6.90 (1H, d, J=2.1 Hz); 7.02 (1H, dd, J=8.1 Hz); 7.77 (1H, d, J=8.4 Hz); 9.05 (3H, b).

Step V: (±) 1-(7-Chloro-3,4-dihydro-spiro[2H-1-benzopyran-2,1'-cyclobutane]-4-yl)-3-(isoquinolin-5-yl)urea This compound was prepared by treatment of (A) 4-Amino-7-chloro-3,4-dihydro-spiro[2H-1-benzopyran-2,1'-cyclobutane] with phenyl N-(isoquinolin-5-yl)carbamate as described in step 1V of example 1.
$^1$H NMR (DMSO-d$_6$): δ 1.73-1.99 (3H, m); 2.15-2.54 (5H, m); 4.99 (1H, m); 6.89 (1H, d, J=2.1 Hz); 6.98 (1H, dd, J=8.1 & 2.1 Hz); 7.05 (1H, d, J=8.1 Hz); 7.31 (1H, d, J=8.1 Hz); 7.63 (1H, t, J=8.1 Hz); 7.77 (1H, d, J=8.1 Hz); 7.93 (1H, d, J=6.3 Hz); 8.35 (1H, d, J=7.8 Hz); 8.56 (1H, d, J=6.3 Hz); 8.77 (1H, s); 9.29 (1H, s); IR (KBr) (cm$^{-1}$): 3327, 1622, 1564, 1236;
MS (M$^+$+1): 394.2

Example 77

(±) 1-(3,4-Dihydro-6-nitro-spiro[2H-1-benzopyran-2,1'-cyclobutane]-4-yl)-3-(isoquinolin-5-yl)urea Step I: 3,4-Dihydro-6-nitro-4-oxo-spiro[2H-1-benzopyran-2,1'-cyclobutane]

To a solution of 3,4-Dihydro-4-oxo-spiro[2H-1-benzopyran-2,1'-cyclobutane] (Example 3) (10 mmol) in glacial acetic acid (2 ml), conc. H$_2$SO$_4$ (10 mmol) was added at 0° C. and the mixture was stirred for 10 min. A chilled nitrating mixture [prepared from HNO3 (9 mmol) and Conc. H$_2$SO$_4$ (10 mmol)] was then added very slowly and the reaction mixture was allowed to warm up to room temperature and stirred for 5 h. reaction mixture was then quenched with water and the compound was extracted in dichloromethane. Organic layer was separated, dried on anhydrous MgSO4 and concentrated under vacuum. The crude product was then purified by column chromatography to afford the desired compound as a yellow solid.
$^1$H NMR (CDCl$_3$): δ 1.70-1.85 (1H, m); 1.92-2.06 (1H, m); 2.17-2.28 (2H, m); 2.33-2.48 (2H, m); 2.99 (2H, s); 7.12 (1H, d, J=9.0 Hz); 8.34 (1H, dd, J=3.0 & 9.0 Hz); 8.75 (1H, d, J=2.7 Hz).

Step II: 3,4-Dihydro-4-hydroxy-6-nitro-spiro[2H-1-benzopyran-2,1'-cyclobutane]

This compound was prepared in the same manner from 3,4-Dihydro-6-nitro-4-oxo-spiro[2H-1-benzopyran-2,1'-cyclobutane] as in the step II of example 6.

Step III: 4-Acetamido-3,4-Dihydro-6-nitro-spiro[2H-1-benzopyran-2,1'-cyclobutane]

This compound was prepared in the same manner from 6-nitro-3,4-dihydro-4-hydroxy-spiro[2H-1-benzopyran-2,1'-cyclobutane] as in step III of example 6.

Step IV: (±) 4-Amino-3,4-Dihydro-6-nitro-spiro[2H-1-benzopyran-2,1'-cyclobutane]

This compound was prepared in the same manner from 6-nitro-3,4-dihydro-4-hydroxy-spiro[2H-1-benzopyran-2,1'-cyclobutane] as in step III of example 6. Isolated as hydrochloride
$^1$H NMR (DMSO-d$_6$): δ 1.65-1.74 (1H, m), 1.80-2.34 (5H, m); 2.37-2.66 (2H, m); 4.71 (1H, m); 7.10 (1H, d, J=9.0 Hz); 8.16 (1H, dd, J=9.0 Hz); 8.63 (1H, d, J=2.4 Hz); 8.85 (3H, b).

Step V: (±) 1-(3,4-Dihydro-6-nitro-spiro[2H-1-benzopyran-2,1'-cyclobutane]-4-yl)-3-(isoquinolin-5-yl)urea This compound was prepared in the same manner from (±) 4-Amino-3,4-Dihydro-6-nitro-spiro[2H-1-benzopyran-2,1'-cyclobutane] as in step 1V of example 1.
$^1$H NMR (DMSO-d$_6$): δ 1.76-2.08 (3H, m); 2.08-2.48 (5H, m); 5.08 (1H, m); 7.05 (1H, d, J=8.7 Hz); 7.19 (1H, d, J=8.4 Hz); 7.66 (1H, t, J=7.5 Hz); 7.82 (1H, d, J=7.5 Hz); 7.96 (1H, d, J=6.0 Hz); 8.09 (1H, dd, J=2.7 & 6.0 Hz); 8.21 (1H, d, J=2.7

Hz); 8.30 (1H, d, J=7.5 Hz); 8.57 (1H, d, J=6.3 Hz); 8.89 (1H, s); 9.31 (1H, s); IR (KBr) (cm$^{-1}$): 3300, 1638, 1580, 1514, 1338, 1321, 1260, 1242, 1101, 751; MS (M$^+$+1):

Example 78

(±) 1-(6-Acetamido-3,4-dihydro-spiro[2H-1-benzopyran-2,1'-cyclobutane]-4-yl)-3-(isoquinolin-5-yl)urea This compound was synthesized by acetylation of 1-(6-Amino-3,4-dihydro-spiro[2H-1-benzopyran-2,1'-cyclobutane]-4-yl)-3-(isoquinolin-5-yl)urea (example 39) using acetyl chloride in presence of triethylamine in THF.

$^1$H NMR (DMSO-d$_6$): δ 1.72-1.89 (3H, m); 1.96 (1H, s); 2.00-2.45 (5H, m); 5.01 (1H, s); 6.73 (1H, d, J=8.4 Hz); 6.99 (1H, d, J=8.4 Hz); 7.43 (2H, m); 7.65 (1H, d, J=7.5 Hz); 7.78 (1H, d, J=8.4 Hz); 7.97 (1H, d, J=6.0 Hz); 8.42 (1H, d, J=7.2 Hz); 8.57 (1H, d, J=6.0 Hz); 8.76 (1H, s); 9.31 (1H, s); 9.80 (1H, s); IR (KBr) (cm$^{-1}$): 3293, 1657, 1548, 1492, 1221; MS (M$^+$+1): 417.1

Example 79

(±) 1-(6-Amino-3,4-dihydro-spiro[2H-1-benzopyran-2,1'-cyclobutane]-4-yl)-3-(isoquinolin-5-yl)urea This compound was synthesized by reduction of (±) 1-(3,4-Dihydro-6-nitro-spiro[2H-1-benzopyran-2,1'-cyclobutane]-4-yl)-3-(isoquinolin-5-yl)urea (example 22) using 10% Pd/C at a hydrogen pressure of 40 psi in methanol.

$^1$H NMR (DMSO-d$_6$): δ 1.68-1.87 (3H, m); 2.00-2.40 (5H, m); 4.67 (2H, b s); 4.91 (1H, m); 6.42 (1H, m); 6.52 (2H, m); 6.99 (1H, d, J=8.1 Hz); 7.63 (1H, m); 7.75 (1H, d, J=7.8 Hz); 7.94 (1H, d, J=5.7 Hz); 8.42 (1H, d, J=7.8 Hz); 8.55 (1H, m); 8.71 (1H, s); 9.28 (1H, s); IR (KBr) (cm$^{-1}$): 3348, 3277, 1645, 1548, 1218; MS (M$^+$+1): 375.1

Example 80

N'-isoquinolin-5-yl-N-3,3',4,4'-tetrahydro-2'H-spiro[chromene-2,1'-cyclobutan]-4-ylthiourea(N'-isoquinolin-5-yl-N-3,4-dihydro-2H-spiro[chromene-2,1'-cyclobutan]-4-ylthiourea)

A solution of 5-amino isoquinoline (1 mmol), 1,1-thiocarbonyldiimidazole (1.25 mmol) and triethyl amine (1.0 mmol) in THF was stirred at room temperature for 45 minutes and was added 4-amino-3,4-dihydrospiro[2H-1-benzopyran-2,1'-cyclobutane] (1 mmol). Few drops of water were added in the reaction mixture. Product precipitated out, was filtered and washed with water. It was then purified by column chromatography to afford the desired thiourea as white solid, m.p. 187-188° C.

$^1$H NMR (DMSO-d$_6$): δ 1.70-1.94 (3H, m); 2.02-2.46 (5H, m); 5.84 (1H, m); 6.75 (1H, d, J=8.1 Hz); 6.88 (1H, m); 7.12 (1H, m); 7.23 (1H, m); 7.69 (1H, t, J=7.8 Hz); 7.78 (1H, d, J=5.4 Hz); 7.84 (1H, d, J=6.9 Hz); 8.05 (1H, d, J=8.1 Hz); 8.17 (1H, d, J=8.4 Hz); 8.58 (1H, d, J=5.4 Hz); 9.34 (1H, s) 9.81 (1H, s); IR (KBr) (cm$^{-1}$): 3212, 1547, 1231, 757; MS (M$^+$+1): 376.24

Example 81

(±) 1-(3,4-dihydro-spiro[2H-1-benzothiopyran-2,1'-cyclobutan]-4-yl)-3-(isoquinolin-5-yl)urea Step I: 1-Phenylthiocyclobutane-1-acetic acid A solution of thiophenol (70 mmol) in THF (10 ml) was refluxed for 1 h in the presence of K$_2$CO$_3$ (70 mmol) as a base. A solution of Cyclobutylidene acetic acid (intermediate 1) (35 mmol) in DMF (1.0 ml) was added to the above reaction. The reaction was monitored by TLC for completion. After 3 days the reaction was cooled and filtered. It was then neutralized with ethyl acetate saturated with hydrochloric acid and the compound was extracted with ethyl acetate. Organic layer was then separated, dried over anhydrous Na$_2$SO$_4$ and concentrated under vacuum. The residue was column purified to give the compound as a yellow solid.

Step II: 3,4-Dihydro-4-oxo-spiro[2H-1-benzothiopyran-2,1'-cyclobutane]

A solution of 1-Phenylthiocyclobutane-1-acetic acid (10 mmol) in benzene was treated with excess of PCl$_5$ at room temperature for 15 h. The reaction mixture was concentrated under vacuum and the residue was again dissolved in benzene. AlCl$_3$ was then added to the solution and it was stirred for 24 h at room temperature. The reaction mixture was diluted with excess of ethyl acetate and washed with water and brine. Organic layer was then separated, dried over anhydrous Na$_2$SO$_4$ and concentrated under vacuum. The residue was purified by column chromatography to afford the desired compound as oil.

$^1$H NMR (CDCl$_3$): δ2.00-2.30 (6H, m); 3.11 (2H, s); 7.16 (1H, t, J=7.8 Hz); 7.24 (1H, d, J=8.4 Hz); 7.41 (1H, d, J=8.4 Hz); 8.06 (1H, d, J=8.1 Hz).

Step III: (±) 4-amino-3,4-dihydro-spiro[2H-1-benzothiopyran-2,1'-cyclobutane]

To a solution of 3,4-Dihydro-4-oxo-spiro[2H-1-benzothiopyran-2,1'-cyclobutane] (4.8 mmol, 100 mg) in methanol (10 ml) was added ammonium acetate (4.8 mmol, 377 mg) and sodiumcyanoborohydride (3.4 mmol, 215 mg) and the reaction was refluxed for 10-12 h. Reaction was cooled and acidified with 6N HCl and stirred for 3-6 h. Reaction was quenched with 2N sodium hydroxide, extracted with ethyl acetate. The organic extract was concentrated and the residue was treated with ethyl acetate saturated with hydrochloric acid to obtain the amine hydrochloride (60 mg).

Step IV: (±) 1-(3,4-dihydro-spiro[2H-1-benzothiopyran-2,1'-cyclobutan]-4-yl)-3-(isoquinolin-5-yl)urea This compound was prepared from (i) 4-amino-3,4-dihydro-spiro[2H-1-benzothiopyran-2,1'-cyclobutane] as in step 1V of example 1.

$^1$H NMR (DMSO-d$_6$): δ 1.96-2.46 (8H, m); 4.94 (1H, m); 7.07-(1H, dd, J=2.7 & 10.8 Hz); 6.76 (1H, dt, J=2.7 & 8.7 Hz); 7.32 (1H, d, J=7.2 Hz); 7.61 (1H, m); 7.94 (1H, t, J=7.8 Hz); 8.10 (1H, d, J=7.8 Hz); 8.73 (3H, m); 9.61 (1H, m); 9.81 (1H, s).

The compounds in example 26 to example 35 were synthesized by the process described in step IV of example 1 using the appropriately substituted (±) 4-Amino-3,4-dihydro spiro [2H-1-benzopyran-2,1'-cyclobutane] and the phenyl carbamate of appropriately substituted 5-aminoisoquinoline.

Example 82

(±) 1-(1,1-dioxo-3,4-dihydro-spiro[2H-1-benzothiopyran-2,1'cyclobutane]-4-yl)-3-(isoquinolin-5-yl)urea

Step I: 3,4-Dihydro-1,1,4-trioxo-spiro[2H-1-benzothiopyran-2,1'-cyclobutane]

3,4-Dihydro-4-oxo-spiro[2H-1-benzothiopyran-2,1'-cyclobutane] (from step II of example 25) was oxidized to the sulfoxide using m-CPBA (2.0 eq) in acetonitrile. Quenching with excess water and extraction with ethyl acetate provided the product which was purified by column chromatography using 7% ethyl acetate in petroleum ether to give the sulfoxide as white solid.

$^1$H NMR (CDCl$_3$): δ2.02-2.25 (4H, m); 2.86 (2H, m); 3.55 (2H, bs); 7.72 (1H, m); 7.82 (1H, m); 8.01 (2H, m); IR (KBr) (cm$^{-1}$): 3348, 3277, 1645, 1548, 1218; MS (M$^+$+1): 375.1

Step II: (±) 4-Amino-3,4-dihydro-1,1-dioxo-spiro[2H-1-benzothiopyran-2,1'-cyclobutane]hydrochloride This compound was synthesized from above 3,4-Dihydro-1,1,4-trioxo-spiro[2H-1-benzothiopyran-2,1'-cyclobutane] by the process described in step III of example 25. Isolated as a hydrochloride.

$^1$H NMR (DMSO-d$_6$): δ 2.03-2.14 (3H, m); 2.35-2.42 (2H, m); 2.60-2.73 (2H, m); 2.94-3.00 (1H, m); 4.88 (1H, m); 7.67 (1H, t, J=8.1 Hz); 7.70 (1H, t, J=7.2 Hz); 7.95 (1H, d, J=7.5 Hz); 9.06 (3H, bs).

Step 3: (±) 1-(1) 1-dioxo-3,4-dihydro-spiro[2H-1-benzothiopyran-2,1'cyclobutane]-4-yl)-3-(isoquinolin-5-yl)urea This compound was prepared in the same manner from above (±) 4-Amino-3,4-dihydro-1,1-dioxo-spiro[2H-1-benzothiopyran-2,1'-cyclobutane] and phenyl carbamate of 5-aminoisoquinoline as in step 1V of example 1.

$^1$H NMR (DMSO-d$_6$): δ 2.08-2.42 (4H, m); 2.58-2.85 (4H, m); 5.25 (1H, m); 7.33 (1H, d, J=8.1 Hz); 7.56-7.69 (4H, m); 7.81 (1H, d, J=7.5 Hz); 7.87-7.94 (2H, m); 8.33 (1H, d, J=6.9 Hz); 8.56 (1H, d, J=5.8 Hz); 8.76 (1H, s); 9.32 (1H, s).

Example 83

N'-isoquinolin-8-yl-N-3,3',4,4'-tetrahydro-2'H-spiro[chromene-2,1'-cyclobutane]-4-ylthiourea (N'-isoquinolin-8-yl-N-3,4-dihydro-2H-spiro[chromene-2,1'-cyclobutan]-4-ylthiourea)

This compound was prepared by the same method as described in the example III from 8-amino isoquinoline, 1,1-thiocarbonyldiimidazole and 4-amino-3,4-dihydrospiro[2H-1-benzopyran-2,1'-cyclobutan], m.p. 187-188° C.

$^1$H NMR (DMSO-d$_6$): δ 1.70-1.94 (3H, m); 2.02-2.50 (5H, m); 5.85 (1H, m); 6.76 (1H, d, J=7.8 Hz); 6.88 (1H, m); 7.10-7.18 (1H, m); 7.20-7.28 (1H, m); 7.67 (1H, t, J=6.6 Hz); 7.78 (1H, t, J=7.8 Hz); 7.82-7.95 (2H, m); 8.29 (1H, d, J=8.1 Hz); 8.53 (1H, d, J=5.1 Hz); 9.33 (1H, s) 9.95 (1H, s); IR (KBr) (cm$^{-1}$): 3437, 3191, 2931, 1625, 1547, 1231

MS (M$^+$+1): 376.29

Example 84

Screening for TRPV1 Antagonist using the $^{45}$Calcium Uptake Assay

The inhibition of TRPV1 receptor activation was followed as inhibition of capsaicin induced cellular uptake of radioactive calcium which represents calcium influx exclusively through the plasma membrane associated TRPV1 receptor.

Materials:

Stock solution of capsaicin was made in ethanol and test compounds in 100% DMSO. Stock solutions were diluted to appropriate final concentrations in assay buffer keeping the final DMSO concentration between 0.1% and 0.55%.

$^{45}$Ca was used at a final concentration of 2.5 μCi/ml ($^{45}$Ca, ICN).

Assay buffer was composed of F-12 DMEM medium supplemented with 1.8 mM CaCl$_2$ (final conc.) and 0.1% Bovine serum albumin. (BSA from SIGMA)

Wash buffer was tyrodes solution supplemented with 0.1% BSA and 1.8 mM calcium. Lysis buffer contained 50 mM Tris-HCl, pH7.5, 150 mM NaCl, 1% Triton X-100, 0.5% deoxycholate and 0.1% Sodium dodicyl sulphate (SDS, SIGMA)

Method:

Assay was carried out with some modifications the of procedure as described by Toth et. al. (See Toth A et. al., *Life Sciences* 73 p 487-498, 2003). Human TRPV1 expressing CHO cells were grown in F-12 DMEM (Dulbecco's modified Eagle's medium—GIBCO) medium with 10% FBS (fetal bovine serum Hyclone), 1% penicillin-streptomycin solution, 400 μg/ml of G-418. Cells were seeded 48 h prior to the assay in 96 well plates so as to get ~50,000 cells per well on the day of experiment. Plates were incubated at 37° C. in the presence of 5% CO$_2$. Cells were then washed twice with 200 μl of assay buffer and re-suspended in 144 μl of the same. Assay was carried out at 30° C. in total volume of 200 μl. Test compounds were added to the cells fifteen minutes before addition of capsaicin, Final concentration of capsaicin in the assay was 250 nM. After 5 minutes of agonist treatment, drug was washed out and wells rinsed with 300 μl of ice cold wash buffer 3×. The cells were lysed in 50 μl lysis buffer for 20 min. 40 μl of cell lysate was mixed with 150 μl of Microscint PS, left overnight for equilibration. Radioactivity in samples was measured as counts per minute (cpm) using Packard Biosciences Top Count. The drug/vehicle/capsaicin treated $^{45}$Ca uptake values were normalized over basal $^{45}$Ca value. Data was expressed as % inhibition of $^{45}$Ca uptake by test compound with respect to maximum $^{45}$Ca uptake induced by capsaicin alone. IC$_{50}$ value was calculated from dose response curve by nonlinear regression analysis using GraphPadPRISM software.

Compounds described herein exhibited IC$_{50}$ in the calcium uptake assay method in low nM to high nM. For example, compounds described herein exhibited IC$_{50}$ between about 797 nM to about 2.89 nM, or between about 304 nM to about 2.89 nM, or even between about 103 nM to about 2.89 nM. Compounds described herein exhibited IC$_{50}$ between about 585 nM to about 0.2 nM, between about 123 nM to about 0.21 nM, or even between about 29.93 nM to about 0.21 nM. Further, compounds described herein exhibited IC$_{50}$ between about 1259 nM to about 5.2 nM, between about 307 nM to about 5.2 nM, or even between about 23 nM to about 5.2 nM.

The results of these experiments are shown in the table below.

| Example No. | % inhibition of $^{45}$Ca uptake at 1 μM | IC$_{50}$ nM |
|---|---|---|
| 1 | 142.29 | — |
| 2 | 96.12 | 170.8 |
| 3 | 100 | 2.89 |
| 4 | >50% | 7.8 |
| 5 | >50% | 304 |
| 6 | >50% | 339 |
| 7 | >50% | 183 |
| 8 | >50% | 551 |
| 9 | >50% | 103 |
| 10 | >50% | 104 |
| 11 | <50% | — |
| 12 | <50% | — |
| 13 | >50% | 147 |
| 14 | <50% | — |
| 15 | <50% | — |
| 16 | >50% | 797 |
| 17 | <50% | — |
| 18 | <50% | — |
| 19 | <50% | — |
| 20 | <50% | — |
| 21 | <50% | — |
| 22 | <50% | — |
| 23 | <50% | — |
| 24 | <50% | — |
| 25 | <50% | — |
| 26 | 19.84 | — |
| 27 | 46.89 | — |
| 28 | <50% | — |
| 29 | <50% | — |
| 30 | <50% | — |
| 31 | <50% | — |
| 32 | <50% | — |
| 33 | 10.53 | — |
| 34 | 15.62 | — |
| 35 | 8.82 | — |
| 36 | 4.04 | — |
| 37 | 0.00 | — |
| 38 | 10.88 | — |
| 39 | 0.00 | — |
| 40 | >50% | 123 |
| 41 | >50% | 0.48 |
| 42 | >50% | 11.95 |
| 43 | >50% | 5.2 |
| 44 | <50% | — |
| 45 | <50% | — |
| 46 | <50% | — |
| 47 | >50% | 0.21 |
| 48 | >50% | 16.1 |
| 49 | >50% | 29.93 |
| 50 | >50% | 7.8 |
| 51 | >50% | 585 |
| 52 | <50% | — |
| 53 | >50% | 15.8 |
| 54 | >50% | 2.23 |
| 55 | <50% | — |
| 56 | >50% | 14.4 |
| 57 | >50% | 442 |
| 58 | <50% | — |
| 59 | >50% | 7.59 |
| 60 | <50% | — |
| 61 | >50% | 775 |
| 62 | <50% | — |
| 63 | >50% | 307 |
| 64 | <50% | — |
| 65 | >50% | 404 |
| 66 | >50% | 462 |
| 67 | >50% | 447 |
| 68 | >50% | 222 |
| 69 | >50% | 45 |
| 70 | <50% | — |
| 71 | >50% | 591 |
| 72 | >50% | 469 |
| 73 | >50% | 1259 |
| 74 | >50% | 917 |
| 75 | >50% | 23 |
| 76 | <50% | — |
| 77 | >50% | 463 |
| 78 | <50% | — |
| 79 | <50% | — |
| 80 | >50% | 49 |
| 81 | >50% | 5.2 |
| 82 | >50% | 224 |
| 83 | <50% | — |

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above.

All publications, patents, and patent applications cited in this application are herein incorporated by reference to the same extent as if each individual publication, patent, or patent application was specifically and individually indicated to be incorporated herein by reference.

We claim:

1. The compound (±) 1-(3,4-dihydro-spiro-[2H-1-benzopyran-2,1'-cyclobutane]-4-yl)-3-(isoquinolin-5-yl)urea, or a pharmaceutically acceptable salt thereof.

2. The compound (+) 1-(3,4-dihydro-spiro-[2H-1-benzopyran-2,1'-cyclobutane]-4-yl)-3-(isoquinolin-5-yl)urea, or a pharmaceutically acceptable salt thereof.

3. The compound (+) 1-(3,4-dihydro-spiro-[2H-1-benzopyran-2,1'-cyclobutane]-4-yl)-3-(isoquinolin-5-yl)urea hydrochloride.

4. The compound (+) 1-(3,4-dihydro-spiro-[2H-1-benzopyran-2,1'-cyclobutane]-4-yl)-3-(isoquinolin-5-yl)urea sulfate.

5. A pharmaceutical composition comprising (±) 1-(3,4-dihydro-spiro-[2H-1-benzopyran-2,1'-cyclobutane]-4-yl)-3-(isoquinolin-5-yl)urea, or a pharmaceutically acceptable salt thereof, and a pharmaceutically acceptable excipient.

6. A pharmaceutical composition comprising (+) 1-(3,4-dihydro-spiro-[2H-1-benzopyran-2,1'-cyclobutane]-(isoquinolin-5-yl)urea, or a pharmaceutically acceptable salt thereof, and a pharmaceutically acceptable excipient.

7. The pharmaceutical composition of claim 6, wherein the pharmaceutical composition comprises (+) 1-(3,4-dihydro-spiro-[2H-1-benzopyran-2,1'-cyclobutane]-4-yl)-3-(isoquinolin-5-yl)urea hydrochloride.

8. The pharmaceutical composition of claim 6, wherein the pharmaceutical composition comprises (+) 1-(3,4-dihydro-spiro-[2H-1-benzopyran-2,1'-cyclobutane]-4-yl)-3-(isoquinolin-5-yl)urea sulfate.

9. A method of treating pain in a subject in need thereof comprising administering to the subject a therapeutically effective amount of a compound according to claim 1.

10. A method of treating pain in a subject in need thereof comprising administering to the subject a therapeutically effective amount of a compound according to claim 2.

11. A method of treating pain in a subject in need thereof comprising administering to the subject a therapeutically effective amount of a compound according to claim 3.

12. A method of treating pain in a subject in need thereof comprising administering to the subject a therapeutically effective amount of a compound according to claim 4.

13. The method of claim 9, wherein the pain is osteoarthritic pain.

14. The method of claim 10, wherein the pain is osteoarthritic pain.

15. The method of claim 11, wherein the pain is osteoarthritic pain.

16. The method of claim 12, wherein the pain is osteoarthritic pain.

17. The compound 1-(3,4-dihydro-spiro-[2H-1-benzopyran-2,1'-cyclobutane]-4-yl)-3-(isoquinolin-5-yl)urea, or a pharmaceutically acceptable salt thereof.

18. A pharmaceutical composition comprising 1-(3,4-dihydro-spiro-[2H-1-benzopyran-2,1'-cyclobutane]-4-yl)-3-(isoquinolin-5-yl)urea, or a pharmaceutically acceptable salt thereof, and a pharmaceutically acceptable excipient.

19. A method of treating a vanilloid receptor mediated disease, disorder or syndrome in a subject in need thereof comprising administering to the subject a therapeutically effective amount of a compound according to claim 1,
wherein the vanilloid receptor mediated disease, disorder or syndrome is gastro-esophageal reflux disease, cystitis, inflammatory pain, urinary incontinence, irritable bowel syndrome, cough, anxiety or non-allergic rhinitis.

20. A method of treating gastro-esophageal reflux disease in a subject in need thereof comprising administering to the subject a therapeutically effective amount of a compound according to claim 2.

21. A method of treating cystitis in a subject in need thereof comprising administering to the subject a therapeutically effective amount of a compound according to claim 2.

22. A method of treating inflammatory pain in a subject in need thereof comprising administering to the subject a therapeutically effective amount of a compound according to claim 2.

23. A method of treating urinary incontinence in a subject in need thereof comprising administering to the subject a therapeutically effective amount of a compound according to claim 2.

24. A method of treating irritable bowel syndrome in a subject in need thereof comprising administering to the subject a therapeutically effective amount of a compound according to claim 2.

25. A method of treating a cough in a subject in need thereof comprising administering to the subject a therapeutically effective amount of a compound according to claim 2.

26. A method of treating anxiety in a subject in need thereof comprising administering to the subject a therapeutically effective amount of a compound according to claim 2.

27. A method of treating non-allergic rhinitis in a subject in need thereof comprising administering to the subject a therapeutically effective amount of a compound according to claim 2.

28. The compound (±) 1-(3,4-dihydro-spiro-[2H-1-benzopyran-2,1'-cyclobutane]-4-yl)-3-(2-oxoisoquinolin-5-yl)urea, or a pharmaceutically acceptable salt thereof.

29. The compound (+) 1-(3,4-dihydro-spiro-[2H-1-benzopyran-2,1'-cyclobutane]-4-yl)-3-(2-oxoisoquinolin-5-yl)urea, or a pharmaceutically acceptable salt thereof.

30. A pharmaceutical composition comprising (±) 1-(3,4-dihydro-spiro-[2H-1-benzopyran-2,1'-cyclobutane]-4-yl)-3-(2-oxoisoquinolin-5-yl)urea, or a pharmaceutically acceptable salt thereof, and a pharmaceutically acceptable excipient.

31. A pharmaceutical composition comprising (+) 1-(3,4-dihydro-spiro-[2H-1-benzopyran-2,1'-cyclobutane]-4-yl)-3-(2-oxoisoquinolin-5-yl)urea, or a pharmaceutically acceptable salt thereof, and a pharmaceutically acceptable excipient.

32. A method of treating a vanilloid receptor mediated disease, disorder or syndrome in a subject in need thereof comprising administering to the subject a therapeutically effective amount of a compound according to claim 28,
wherein the vanilloid receptor mediated disease, disorder or syndrome is gastro-esophageal reflux disease, cystitis, inflammatory pain, urinary incontinence, irritable bowel syndrome, cough, anxiety or non-allergic rhinitis.

33. A method of treating gastro-esophageal reflux disease in a subject in need thereof comprising administering to the subject a therapeutically effective amount of a compound according to claim 29.

34. A method of treating cystitis in a subject in need thereof comprising administering to the subject a therapeutically effective amount of a compound according to claim 29.

35. A method of treating inflammatory pain in a subject in need thereof comprising administering to the subject a therapeutically effective amount of a compound according to claim 29.

36. A method of treating urinary incontinence in a subject in need thereof comprising administering to the subject a therapeutically effective amount of a compound according to claim 29.

37. A method of treating irritable bowel syndrome in a subject in need thereof comprising administering to the subject a therapeutically effective amount of a compound according to claim 29.

38. A method of treating a cough in a subject in need thereof comprising administering to the subject a therapeutically effective amount of a compound according to claim 29.

39. A method of treating anxiety in a subject in need thereof comprising administering to the subject a therapeutically effective amount of a compound according to claim 29.

40. A method of treating non-allergic rhinitis in a subject in need thereof comprising administering to the subject a therapeutically effective amount of a compound according to claim 29.

* * * * *